(12) United States Patent
Lewis et al.

(10) Patent No.: US 7,122,152 B2
(45) Date of Patent: Oct. 17, 2006

(54) SPATIOTEMPORAL AND GEOMETRIC OPTIMIZATION OF SENSOR ARRAYS FOR DETECTING ANALYTES FLUIDS

(75) Inventors: Nathan S. Lewis, La Canada, CA (US); Michael S. Freund, Altadena, CA (US); Shawn M. Briglin, Pasadena, CA (US); Phil Tokumaru, Moorpark, CA (US); Charles R. Martin, Gainesville, FL (US); David T. Mitchell, Gainesville, FL (US)

(73) Assignees: University of Florida, Gainesville, FL (US); The California Institute of Technology, Pasadena, CA (US); Aerovironment, Inc., Monrovia, CA (US)

(*) Notice: Subject to any disclaimer, the term of this patent is extended or adjusted under 35 U.S.C. 154(b) by 688 days.

(21) Appl. No.: 09/842,204

(22) Filed: Apr. 24, 2001

(65) Prior Publication Data
US 2002/0142477 A1 Oct. 3, 2002

Related U.S. Application Data

(63) Continuation-in-part of application No. 09/568,784, filed on May 10, 2000, now Pat. No. 6,455,319.

(60) Provisional application No. 60/235,385, filed on Sep. 25, 2000, provisional application No. 60/199,221, filed on Apr. 24, 2000, provisional application No. 60/140,027, filed on Jun. 16, 1999, provisional application No. 60/133,318, filed on May 10, 1999.

(51) Int. Cl.
C12Q 1/68 (2006.01)
B01N 15/06 (2006.01)
B01N 33/00 (2006.01)
B01N 33/48 (2006.01)
B32B 5/02 (2006.01)

(52) U.S. Cl. .......... 422/50; 422/68.1; 422/81; 422/82; 422/82.01; 422/82.02; 422/83; 422/98; 422/100; 422/101; 73/1.01; 73/1.02; 73/23.2; 73/53.01; 436/43; 436/149; 29/592; 29/592.1

(58) Field of Classification Search .......... 73/1.01, 73/1.02, 23.2, 53.01; 422/50, 56, 57, 58, 422/60, 68.1, 81, 82, 82.01, 83, 98, 82.02, 422/100, 101; 436/43, 149; 29/592, 592.1
See application file for complete search history.

(56) References Cited

U.S. PATENT DOCUMENTS

| | | |
|---|---|---|
| 3,677,071 A | 7/1972 | Martin et al. |
| 4,172,721 A | 10/1979 | Byrne |
| 4,225,410 A | 9/1980 | Pace et al. |
| 4,349,664 A | 9/1982 | Matsumura et al. |
| 4,424,487 A | 1/1984 | Lauffer et al. |
| 4,644,154 A | 2/1987 | Brogardh et al. |
| 4,674,320 A | 6/1987 | Hirschfeld |
| 4,719,423 A | 1/1988 | Vinegar et al. |
| 4,772,559 A | 9/1988 | Preti et al. |
| 4,911,801 A | 3/1990 | Pons et al. |
| 4,914,608 A | 4/1990 | LeBihan et al. |
| 4,927,502 A | 5/1990 | Reading et al. |
| 4,946,562 A | 8/1990 | Guruswamy |
| 5,159,829 A | 11/1992 | Mayer et al. |
| 5,212,447 A | 5/1993 | Paltiel |
| 5,215,820 A | 6/1993 | Hosokawa et al. |
| 5,217,692 A | 6/1993 | Rump et al. |
| 5,225,110 A | 7/1993 | Kathirgamanathan |
| 5,246,846 A | 9/1993 | Pittner et al. |
| 5,250,264 A | 10/1993 | Walt et al. |
| 5,253,329 A | 10/1993 | Villareal et al. |
| 5,278,501 A | 1/1994 | Guilfoyle |
| 5,286,414 A | 2/1994 | Kampf et al. |
| 5,302,274 A | 4/1994 | Tomantachger et al. |
| 5,335,555 A | 8/1994 | Guizot et al. |
| 5,352,574 A | 10/1994 | Guiseppi-Elie |
| 5,407,699 A | 4/1995 | Myers |
| 5,415,893 A | 5/1995 | Wiersma et al. |
| 5,417,100 A | 5/1995 | Miller et al. |
| 5,425,869 A | 6/1995 | Noding et al. |
| 5,466,348 A | 11/1995 | Holm-Kennedy |
| 5,469,369 A | 11/1995 | Rose-Pehrsson et al. |
| 5,498,372 A | 3/1996 | Hedges |

Analyte Flow: Normal vs. Composite Sensors

| | | |
|---|---|---|
| 5,505,093 A | 4/1996 | Giedd et al. |
| 5,519,147 A | 5/1996 | Swager et al. |
| 5,536,473 A | 7/1996 | Monkman et al. |
| 5,571,401 A | 11/1996 | Lewis et al. |
| 5,591,898 A | 1/1997 | Mayer |
| 5,627,329 A | 5/1997 | Krishnan et al. |
| 5,653,939 A | 8/1997 | Hollis et al. |
| 5,674,752 A | 10/1997 | Buckley et al. |
| 5,698,089 A | 12/1997 | Lewis et al. |
| 5,705,265 A | 1/1998 | Clough et al. |
| 5,756,879 A | 5/1998 | Yamagishi et al. |
| 5,766,934 A | 6/1998 | Guiseppi-Elie |
| 5,777,483 A * | 7/1998 | Bailey ................. 324/686 |
| 5,788,833 A | 8/1998 | Lewis et al. |
| 5,801,297 A | 9/1998 | Mifsud et al. |
| 5,804,100 A | 9/1998 | Angelopoulos et al. |
| 5,807,701 A | 9/1998 | Payne et al. |
| 5,832,411 A | 11/1998 | Schatzmann et al. |
| 5,841,021 A | 11/1998 | De Castro et al. |
| 5,846,744 A | 12/1998 | Athey et al. |
| 5,876,577 A | 3/1999 | McAleer et al. |
| 5,879,827 A | 3/1999 | Debe et al. |
| 5,891,398 A | 4/1999 | Lewis et al. |
| 5,911,872 A | 6/1999 | Lewis et al. |
| 5,913,235 A | 6/1999 | Silenius et al. |
| 5,948,684 A | 9/1999 | Weigl et al. |
| 5,951,846 A | 9/1999 | Lewis et al. |
| 5,958,787 A | 9/1999 | Schonfeld et al. |
| 5,959,191 A | 9/1999 | Lewis et al. |
| 5,980,723 A | 11/1999 | Runge-Marchese et al. |
| 6,007,775 A | 12/1999 | Yager |
| 6,010,616 A | 1/2000 | Lewis et al. |
| 6,013,229 A | 1/2000 | Lewis et al. |
| 6,017,440 A | 1/2000 | Lewis et al. |
| 6,023,163 A | 2/2000 | Flaum et al. |
| 6,028,608 A | 2/2000 | Jenkins |
| 6,040,189 A | 3/2000 | Buehler |
| 6,085,576 A | 7/2000 | Sunshine et al. |
| 6,093,308 A | 7/2000 | Lewis et al. |
| 6,103,033 A | 8/2000 | Say et al. |
| 6,134,461 A | 10/2000 | Say et al. |
| 6,134,950 A | 10/2000 | Forster et al. |
| 6,170,318 B1 | 1/2001 | Lewis |
| 6,200,814 B1 | 3/2001 | Malmqvist et al. |
| 6,234,004 B1 | 5/2001 | Revsbech et al. |
| 6,290,911 B1 | 9/2001 | Lewis et al. |
| 6,305,214 B1 | 10/2001 | Schattke et al. |
| 6,315,956 B1 | 11/2001 | Foulger |
| 6,350,369 B1 | 2/2002 | Lewis et al. |
| 6,752,964 B1 * | 6/2004 | Grubbs et al. ............ 422/98 |
| 6,759,010 B1 * | 7/2004 | Lewis et al. .......... 422/82.02 |
| 6,908,770 B1 * | 6/2005 | McDevitt et al. ......... 436/518 |

FOREIGN PATENT DOCUMENTS

| | | |
|---|---|---|
| EP | 0 717 418 A2 | 6/1996 |
| EP | 0 878 711 A1 | 11/1998 |
| JP | 62-257968 | 11/1987 |
| JP | 63-120733 | 5/1988 |
| JP | 63-308807 | 12/1988 |
| JP | 11-94784 | 4/1999 |
| WO | WO 86/01599 | 3/1986 |
| WO | WO 90/09027 | 8/1990 |
| WO | WO 94/24561 | 10/1994 |
| WO | WO 95/08113 | 3/1995 |
| WO | WO 96/07901 | 3/1996 |
| WO | WO 99/00663 | 1/1999 |
| WO | WO 99/08105 | 2/1999 |
| WO | WO 99/40423 | 8/1999 |
| WO | WO 99/47905 | 9/1999 |
| WO | WO 99/53287 | 10/1999 |
| WO | WO 99/53300 | 10/1999 |
| WO | WO 99/61902 | 12/1999 |
| WO | WO 99/66304 | 12/1999 |
| WO | WO 99/67627 | 12/1999 |
| WO | WO 00/00808 | 1/2000 |
| WO | WO 00/04372 | 1/2000 |
| WO | WO 00/26638 | 5/2000 |
| WO | WO 00/33062 | 6/2000 |
| WO | WO 00/68675 | 11/2000 |
| WO | WO 01/23883 | 4/2001 |

OTHER PUBLICATIONS

Baldacci, et al., "Discrimination of Wine Using Taste and Smell Sensors", Sensors and Materials, vol. 10, No. 3, pp. 185-200 (1998).

Bodenhofer, et al., "Chiral Discrimination By Simple Gas Sensors", Transducers, 1997 International Conference on Solid-State Sensors and Actuators, Digest of Technical Papers, Transducers 97, chicago, IL, Jun. 16-19, 1997, vol. 2, pp. 1391-1394IEEE.

Bodenhofer et al., "Performances of Mass-Sensitive Devices for Gas Sensing: Thickness Shear Mode and Surface Acoustic Wave Transducers", Anal. Chem., vol. 68, No. 13, pp. 2210-2218 (Jul. 1, 1996).

Breheret et al., "On-line differentiation of mushrooms aromas by combined Headspace/multi-odour gas sensors devices", Bioflavour 95, Dijon, France (Les Colloques, No. 75), pp. 103-107, (Feb. 14-17, 1995).

Bruschi et al., "Gas sensing with conducting polymer thin film resistors obtained from commercial photoresist patterns", Proceedings of the First Italian Conference, (1996), pp. 69-73.

Butterworth, et al., "Zeta Potential measurements on Conducting Polymer-Inorganic Oxide Nanocomposite Particles", Journal of Colloid and Interface Science, vol. 174, pp. 510-517, (1995).

Casella, et al., "Copper dispersed into polyaniline films as an amperometric sensor in alkaline solutions of amino acids and polyhydric compounds", Analytica Chimica Acta, vol. 335, pp. 217-225, (1996).

Chandiok et al., "Screening for bacterial vaginosis: a novel application of artificial nose technology", J. Clin. Pathol., vol. 50, pp. 790-791 (1997).

Costello, et al., "Novel composite organic-inorganic semiconductor sensors for the quantitative detection of target organic vapours", J. Mater. Chem., vol. 6, No. 3, pp. 289-294 (1996).

Dickinson, et al., "Generating Sensor Diversity through Combinatorial Polymer Synthesis", Anal. Chem. vol. 69, pp. 3413-3418, 1997.

Doleman, et al., "Quantitative Study of the Resolving Power of Arrays of Carbon Black-Polymer composites in Various Vapor-Sensing Tasks", Anal. Chem, vol. 70, pp. 4177-4190, 1998.

Domansky, et al., "Development and Calibration of Field-Effect Transistor-Based Sensor Array for Measurement of Hydrogen and Ammonia Gas Mixtures in Humid Air", Anal. Chem., vol. 70, No. 3, pp. 473-481 (Feb. 1, 1998).

Forsyth, et al., "Dielectric properties of conductive composites at microwave frequencies", New Horizons for Materials, 2995, pp. 279-285 (1995).

Jiang, et al., "Preparation and Properties of Organic Polymer Sub-Micrometer Function Films", Electrets, 1996, 9th International Symposium on Shanghai, China, Sep. 25-30, 1996, NY, pp. 678-683.

Laranjeira et al., "A conductimetric system based on polyaniline for determination of ammonia in fertilizers", Analytical Letters, vol. 30, No. 12, pp. 2189-2209 (1997).

Lefebvre, et al., "Chemical Synthesis, Characterization, and Electrochemical Studies of Poly(3,4,-ethylenedioxythiophene)/Poly(styrene-4-sulfonate) Composites", Chem. Mater., vol. 11, No. 2, pp. 262-268 (1999).

Lipman, "E-noses nose out tradiitonal odor-detection equipment", EDN, pp. 59-66, Dec. 17, 1998.

Luinge, et al., "Trace-level identity confirmation from infrared spectra by library searching and artificial neural networks", Analytica Chimica Acta, vol. 345, pp. 173,-184, 1997.

Meister et al., "Polymer-Oxide-Silicon-Field-Effect-Transistor (POSFET) as sensor for gases and vapors", Electrochemical Society Proceedings, vol. 97-9, pp. 16-22.

Moy et al., "Transient signal modelling for fast odour classification", *Bioflavour 95*, Dijon, France, (Les Colloques, No. 75), pp. 55-58, (Feb. 14-17, 1995).

Neaves et al., "A new generation of integrated electronic noses", *Sensors and Actuators*, B 26-27, pp. 223-231 (1995).

Partch, et al., "Conducting Polymer Composites", American Chemical Society, pp. 368-386 (1992).

Paulsson, et al., "Breath alcohol, multi sensor arrays and electronic noses", *SPIE*, vol. 2932, pp. 84-90 (Mar. 1997).

Preti, "Analysis of lung air from patients with bronchogenic carcinoma and controls using gas chromatography-mas spectrometry", *Journal of Chromatography*, vol. 432, pp. 1-11 (1988).

Rajeshwar, et al., "Polypyrrole composits containing platinum or carbon black: from synthesis to novel applications", *Polymer Preprints, American Chemical Society*, vol. 35, No. 1, pp. 234-235, Mar. 1994).

Simenhoff, et al. "Biochemical profile of uremic breath", *The New England Journal of Medicine*, vol. 297, No. 3, pp. 132-135 (Jul. 21, 1977).

Stussi, et al., "Chemoresistive conducting polymer-based odour sensors: influence of thickness changes on their sensing properties", *Sensors and Actuators*, vol. B43, pp. 180-185, (1997).

Thackeray, et al., "Chemically Responsive Microelectrochemical Devices Based on Platinized Poly(3-methylthiophene): Variation in conductivity with Variation in Hydrogen, Oxygen, or pH in Aqueous solution", Feb. 14-17, 1995,*J. Phys. Chem.* Feb. 14-17, 1995, vol. 90, No. 25, pp. 6674-6679 (Nov. 25, 1986).

Tourillon, et al., "Dispersive X-Ray Spectroscopy for Time-Resolved In Situ Observatin of Electrochemical Inclusion of Metallic Clusters within a conducting polymer", *Physical Review Letters*, vol. 57, No. 5, pp. 603-606 (Aug. 4, 1986).

Udrea et al., "Design of a silicon microsensor array device for gas analysis", *Microelectronics Journal*, vol. 27, No. 6, pp. 449-457 (1996).

Wampler, "Composites of Polypyrrole and Carbon Black. 2. Electrosynthesis, Characterization, and Influence of Carbon Black Characteristics", *Chem. Mater.* vol. 7, No. 3, pp. 585-592 (1995).

Veciana-Nogues, et al., "Biogenic Amines as Hygienic Quality Indicators of Tuna, Relationships with Microbial Counts, ATP-Related Compounds, Volatile Amines and Organoleptic Changes", *J. Agric. Food Chemi.*, vol. 45, No. 6, pp. 2036-2041 (1997).

Yamoto et al., "A new method for dispersing palladium icroparticles in conducting polymer films and its application to biosensors", *Synthetic Metals*, vol. 87, pp. 231-236, (1997).

Slater, et al., "Multi-layer Conducting Polymer Gas Sensor Arrays for Olfactory Sensing", *Analyst*, vol. 118, pp. 379-384 (Apr. 1993).

Pearce, et al., "Electronic Nose for Monitoring the Flavour of Beers", *Analyst*, vol. 118, pp. 371-377 (Apr. 1993).

Lonergan, et al., "Array-Based Vapor Sensing Using chemically Sensitive, Carbon Black-Polymer, Resistors", *Chem. Mater.*, vol. 8, No. 9, pp. 2298-2312, (Nov. 9, 1996).

Freund, et al., "A chemically diverse conducting polymer-based 'electronic nose'", *Proc. Natl. Acad. Sci.*, vol. 92, pp. 2652-2656 (Mar. 1995).

Wehrens, et al., "Calibration of an array of voltammetric microelectrodes", *Analytica chimica Acta.*, No. 334, pp. 93-101, 1996.

Williams, et al., "Resolving combustible gas mixtures using gas sensitive resistors with arrays of electrodes", *J. Chem. Soc., Faraday Trans.*, vol. 92, No. 22, pp. 4497-4504, 1996.

\* cited by examiner

*Primary Examiner*—Jill Warden
*Assistant Examiner*—Brian Sines
(74) *Attorney, Agent, or Firm*—Buchanan Ingersoll & Rooney, LLP

(57) ABSTRACT

Sensor arrays and sensor array systems for detecting analytes in fluids. Sensors configured to generate a response upon introduction of a fluid containing one or more analytes can be located on one or more surfaces relative to one or more fluid channels in an array. Fluid channels can take the form of pores or holes in a substrate material. Fluid channels can be formed between one or more substrate plates. Sensor can be fabricated with substantially optimized sensor volumes to generate a response having a substantially maximized signal to noise ratio upon introduction of a fluid containing one or more target analytes. Methods of fabricating and using such sensor arrays and systems are also disclosed.

62 Claims, 22 Drawing Sheets

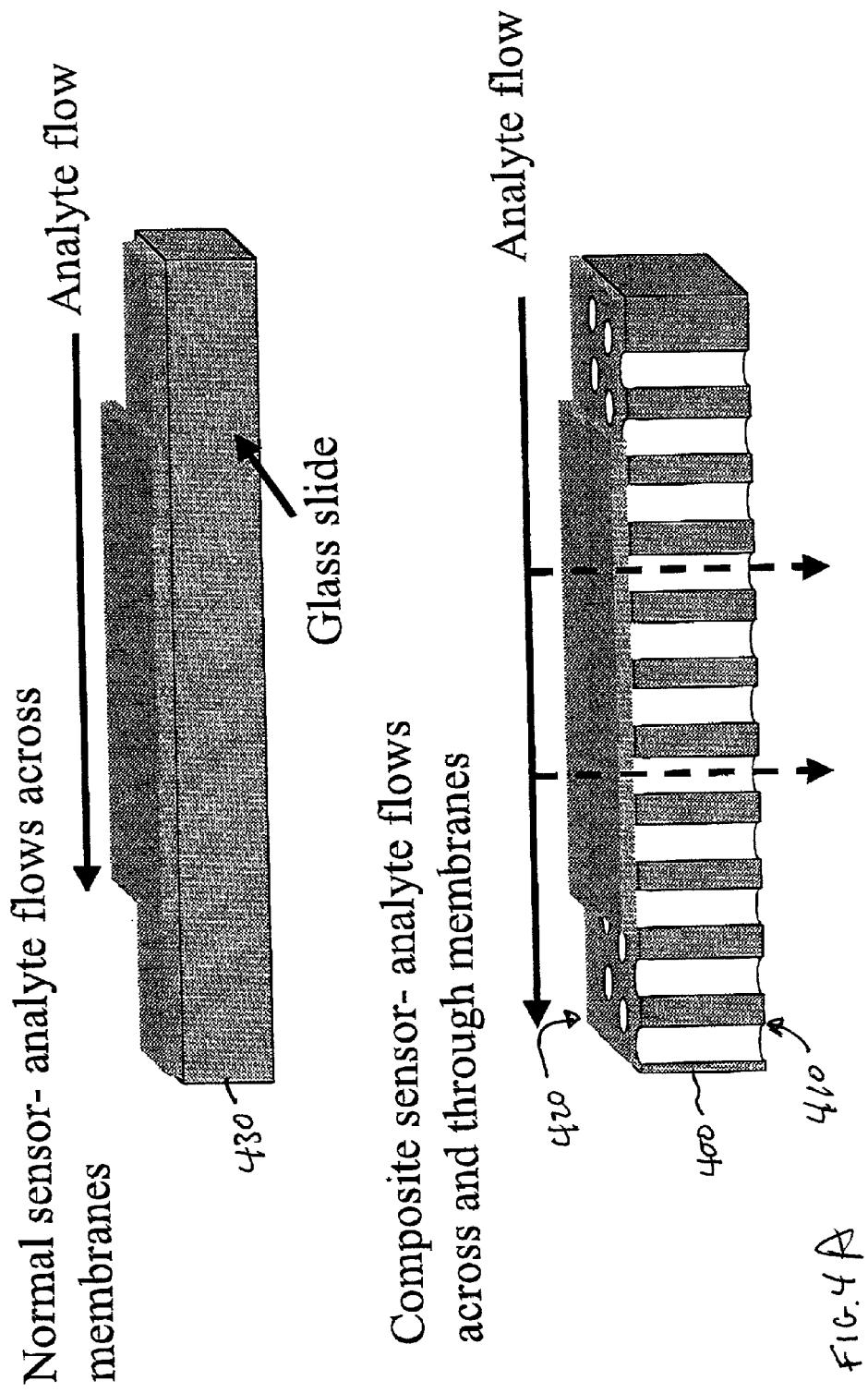

a) face-view of substrate b) leading edge-view of 2 substrates

Responses, Noise, and S/N for two Types of Polymer-Carbon Black Composite Detectors in the Configuration of FIGS. 5A and 5B.[a]

| Analyte | Vapor Pressure of Pure Analyte | | log Partition Coefficient (log k)[b] | | Stack Assembly | ΔR/R$_b$ × 100 | | | | | | $N_{rms}$ | | | | S/N | | | |
|---|---|---|---|---|---|---|---|---|---|---|---|---|---|---|---|---|---|---|---|
| | | | | | | PCL | | PEVA | | | PCL | | PEVA | | PCL | | PEVA | |
| | P° (Torr) | PPM[c] | PCL | PEVA | | edge[d] | face | edge | face | | edge | face | edge | face | edge | face | edge | face |
| hexane | 1.28*10² | 1.71*10⁵ | 1.65 | 2.23 | A | 1.4±0.2 | 1.07±0.03 | 3.3±0.1 | 3.5±0.6 | | (1.5±0.7)*10⁻³ | (1.9±0.5)*10⁻⁴ | (5±1)*10⁻⁴ | (8±2)*10⁻⁵ | 13±7 | 60±14 | 73±20 | 460±200 |
| | | | | | B | 1.1±0.4 | 0.77±0.04 | 3.6±0.3 | 2.5±0.1 | | (2±1)*10⁻³ | (3.2±0.8)*10⁻⁴ | (9±2)*10⁻⁴ | (1.3±0.3)*10⁻⁴ | 5±2 | 26±9 | 44±12 | 200±45 |
| | | | | | C | 1.3±0.2 | 1.17±0.08 | 2.8±0.3 | 2.4±0.1 | | (1.2±0.6)*10⁻³ | (1.8±0.2)*10⁻⁴ | (4±2)*10⁻⁴ | (2.7±0.9)*10⁻⁴ | 23±23 | 100±60 | 77±25 | 100±37 |
| | | | | | mean | 1.3 | 1.0 | 3.2 | 2.8 | | 2*10⁻³ | 2.3*10⁻⁴ | 6*10⁻⁴ | 1.6*10⁻⁴ | 14 | 64 | 65 | 260 |
| methanol | 1.02*10² | 1.36*10⁵ | 2.26 | 1.98 | A | 2.4±0.2 | 2.7±0.1 | 2.0±0.4 | 2.1±0.5 | | (1.4±0.8)*10⁻³ | (2.0±0.5)*10⁻⁴ | (5±1)*10⁻⁴ | (9±2)*10⁻⁵ | 23±12 | 140±42 | 42±10 | 270±120 |
| | | | | | B | 3.3±0.5 | 2.4±0.2 | 1.8±0.3 | 1.61±0.08 | | (3±1)*10⁻³ | (3.0±0.6)*10⁻⁴ | (9±2)*10⁻⁴ | (1.5±0.3)*10⁻⁴ | 14±5 | 80±16 | 21±5 | 120±25 |
| | | | | | C | 2.6±0.8 | 2.8±0.2 | 1.1±0.2 | 1.2±0.1 | | (1.2±0.8)*10⁻³ | (1.3±0.7)*10⁻⁴ | (4±2)*10⁻⁴ | (2.6±0.9)*10⁻⁴ | 33±22 | 260±110 | 28±11 | 50±17 |
| | | | | | mean | 2.8 | 2.6 | 1.6 | 1.6 | | 2*10⁻³ | 2.1*10⁻⁴ | 6*10⁻⁴ | 1.6*10⁻⁴ | 23 | 160 | 30 | 140 |
| dodecane | 9.71*10⁻² | 1.29*10² | 4.77[e] | 5.35[e] | A | 1.6±0.2 | 1.16±0.03 | 3.7±0.1 | 3.6±0.6 | | (1.3±0.6)*10⁻³ | (2.0±0.4)*10⁻⁴ | (5±1)*10⁻⁴ | (9±0.3)*10⁻⁵ | 15±7 | 60±13 | 76±21 | 440±170 |
| | | | | | B | 1.2±0.4 | 0.88±0.07 | 3.8±0.3 | 2.6±0.1 | | (3±1)*10⁻³ | (3.2±0.9)*10⁻⁴ | (9±2)*10⁻⁴ | (1.4±0.2)*10⁻⁴ | 5±2 | 30±10 | 45±14 | 190±35 |
| | | | | | C | 1.6±0.2 | 1.25±0.04 | 3.4±0.1 | 1.3±0.2 | | (1.2±0.8)*10⁻³ | (9±5)*10⁻⁵ | (4±2)*10⁻⁴ | (2.5±0.7)*10⁻⁴ | 32±32 | 150±64 | 100±41 | 54±21 |
| | | | | | mean | 1.5 | 1.1 | 3.6 | 2.5 | | 2*10⁻³ | 2.1*10⁻⁴ | 6*10⁻⁴ | 1.6*10⁻⁴ | 17 | 81 | 73 | 230 |
| hexadecan | 9.11*10⁻⁴ | 1.21 | 6.70[e] | 7.35[e] | A | 0.3±0.2 | 0.01±0.01 | 0.26±0.09 | 0.01±0.01 | | (1.4±0.9)*10⁻³ | (1.9±0.3)*10⁻⁴ | (5±1)*10⁻⁴ | (8±3)*10⁻⁵ | 3±2 | 1±1 | 6±2 | 2±2 |
| | | | | | B | 0.3±0.3 | 0.02±0.03 | 0.4±0.1 | 0.02±0.04 | | (2±2)*10⁻³ | (3.1±0.9)*10⁻⁴ | (9±2)*10⁻⁴ | (1.4±0.3)*10⁻⁴ | 2±1 | 1±1 | 5±2 | 1±3 |
| | | | | | C | 0.3±0.2 | 0.03±0.03 | 0.3±0.1 | 0.04±0.07 | | (1.1±0.7)*10⁻³ | (1.2±0.6)*10⁻⁴ | (4±2)*10⁻⁴ | (2.3±0.7)*10⁻⁴ | 5±4 | 4±4 | 8±3 | 2±3 |
| | | | | | mean | 0.3 | 0.02 | 0.3 | 0.03 | | 2*10⁻³ | 2.1*10⁻⁴ | 6*10⁻⁴ | 1.5*10⁻⁴ | 3 | 2 | 6 | 2 | a) Data were averages of 10 randomized presentations of the 4 analytes each at P/P° =0.050, across 3 copies of each of the 2 detector types, with each value representing 30 vapor/polymer interactions. The experiment was repeated for 3 independently prepared stack assemblies (A,B,&C). The data represent responses after 200 s of exposure to analyte. b) Determined from quartz crystal microbalance measurements on unfilled polymers.
c) Vapor pressure of analyte expressed in ppm of air at 294 K. d) Edge refers to the leading edge sensors and face refers to the face sensors depicted in FIGS. 5A and 5B. The uncertainties are expressed as 95% confidence intervals. e) Values were estimated based on measurements of K for hexane and correction for the differences in vapor pressure between hexane and the alkane of interest assuming constant activity coefficients for the sorption of the alkanes into a given polymeric phase.

FIG. 10

SPATIOTEMPORAL AND GEOMETRIC OPTIMIZATION OF SENSOR ARRAYS FOR DETECTING ANALYTES FLUIDS

CROSS-REFERENCE TO RELATED APPLICATIONS

This application is a continuation-in-part of U.S. application Ser. No. 09/568,784, filed on May 10, 2000 now U.S. Pat. No. 6,455,319, which claims the benefit of U.S. Provisional Application No. 60/133,318, filed on May 10, 1999, U.S. Provisional Application No. 60/140,027, filed on Jun. 16, 1999. This application also claims the benefit of U.S. Provisional Application No. 60/199,221, filed on Apr. 24, 2000, and U.S. Provisional Application No. 60/235,385, filed on Sep. 25, 2000. All of these prior applications and provisional applications are incorporated by reference herein.

STATEMENT REGARDING FEDERALLY SPONSORED RESEARCH

The U.S. Government has certain rights in this invention pursuant to Grant Nos. DAAK-60-97-K-9503 administered by the Defense Advanced Research Projects Agency, DAAG55-97-1-0187 and DAAG55-98-1-0266, both administered by the United States Army, DE-FG03-98NV13367 administered by the Department of Energy, and NAS-1407 administered by the National Aeronautics and Space Administration.

FIELD OF THE INVENTION

This invention relates generally to sensors and sensor systems for detecting analytes in fluids and, more particularly, to sensor systems that incorporate sensors having electrical properties that vary according to the presence and concentration of analytes, and to methods of using such sensor systems.

BACKGROUND

There is considerable interest in developing sensors that act as analogs of the mammalian olfactory system (Lundstrom et al. (1991) Nature 352:47–50; Shurmer and Gardner (1992) Sens. Act. B 8:1–11; Shurmer and Gardner (1993) Sens. Actuators B 15:32). Prior attempts to produce broadly responsive sensor arrays have exploited heated metal oxide thin film resistors (Gardner et al. (1991) Sens. Act. B4:117–121; Gardner et al. (1991) Sens. Act. B 6:71–75); polymer sorption layers on the surfaces of acoustic wave (SAW) resonators (Grate and Abraham (1991) Sens. Act. B 3:85–111; Grate et al. (1993) Anal. Chem. 65:1868–1881), arrays of electrochemical detectors (Stetter et al. (1986) Anal. Chem. 58:860–866; Stetter et al. (1990) Sens. Act. B 1:43–47; Stetter et al. (1993) Anal. Chem. Acta 284:1–11), conductive polymers or composites that consist of regions of conductors and regions of insulating organic materials (Pearce et al. (1993) Analyst 118:371–377; Shurmer et al. (1991) Sens. Act. B 4:29–33; Doleman et al. (1998) Anal. Chem. 70:2560–2654; Lonergan et al. Chem. Mater. 1996, 8:2298). Arrays of metal oxide thin film resistors, typically based on tin oxide ($SnO_2$) films that have been coated with various catalysts, yield distinct, diagnostic responses for several vapors (Corcoran et al. (1993) Sens. Act. B 15:32–37). Surface acoustic wave resonators are extremely sensitive to both mass and acoustic impedance changes of the coatings in array elements, but the signal transduction mechanism involves somewhat complicated electronics, requiring frequency measurement to 1 Hz while sustaining a 100 MHZ Rayleigh wave in the crystal. Attempts have also been made to construct arrays of sensors with conducting organic polymer elements that have been grown electrochemically through use of nominally identical polymer films and coatings. Moreover, Pearce et al., (1993) Analyst 118: 371–377, and Gardner et al., (1994) Sensors and Actuators B 18–19:240–243 describe, polypyrrole based sensor arrays for monitoring beer flavor. U.S. Pat. No. 4,907,441, describes general sensor arrays with particular electrical circuitry. U.S. Pat. No. 4,674,320 describes a single chemoresistive sensor having a semi-conductive material selected from the group consisting of phthalocyanine, halogenated phthalocyanine and sulfonated phthalocyanine, which was used to detect a gas contaminant. Other gas sensors have been described by Dogan et al., Synth. Met. 60, 27–30 (1993) and Kukla, et al. Films. Sens. Act. B., Chemical 37, 135–140 (1996).

Typically, the detectors in such an array are placed in nominally spatially equivalent positions relative to the analyte flow path. In such a configuration, any spatiotemporal differences between detectors are minimized, and the array response pattern is determined by the differing physicochemical responses of the various detectors towards the analyte of interest. The variations in analyte sorption amongst various detectors thus determines the resolving power of the detector array and determines the other performance parameters of such systems.

Additionally, the form factor of the individual detectors in such arrays is typically constrained by factors related to the mode of signal transduction. For example, most film-coated quartz-crystal microbalance (QCM) devices must have specified dimensions so that a resonant bulk acoustic wave can be maintained in the quartz crystal transducer element. Similarly, the geometry of SAW devices is constrained by the need to sustain a Rayleigh wave of the appropriate resonant frequency at the surface of the transducer crystal. Each detector in a QCM or SAW array typically has an identical area and form factor; consequently, the array response is based solely on the different polymer/analyte sorption properties of the differing detector films.

In practice, most chemical sensors suffer from problems associated with mass transport of the analyte to be detected to the sensor regardless of the type of detector or sensor.

SUMMARY OF THE INVENTION

The invention provides apparatus, systems and methods for detecting the presence of analytes in fluids. Sensor arrays incorporate multiple sensors or detectors. To optimize transport of gaseous analytes to these sensors, sensor arrays can incorporate multiple holes, pores or channels, thus increasing analyte flux.

The geometry and spatiotemporal location of individual detectors can be optimized based on analyte characteristics, such as polymer/gas partition coefficients. For analytes with moderate polymer/gas partition coefficients, detector signal-to-noise can optimized for detectors of very large area. For analytes with high polymer/gas partition coefficients, detectors of small area will exhibit optimum vapor detection sensitivity. Manipulation of the geometric form factor of detectors can provide a convenient method for optimizing the S/N performance for a particular detector/analyte combination of interest. An array of nominally identical sorption detectors arranged linearly relative to the analyte flow path can produce different spatiotemporal response patterns for analytes having different polymer/gas partition coefficients. Analytes with moderate polymer/gas partition coefficients can produce the same signals on all detectors over a range of flow rates, whereas analytes with very large polymer/gas partition coefficients can produce signals that are highly dependent on the analyte flow rate and the spatial position of the detector in the array. Such a configuration can produce useful information on the composition of binary analyte mixtures and adds classification information to an array of compositionally different vapor detectors.

In general, in one aspect, the invention features flow-through systems for detecting an analyte in a fluid flow. The systems include a sensor array having a first face and a second face, a fluid flow system for introducing a fluid flow containing an analyte to the sensor array, such that upon introduction of a fluid flow to the sensor array a pressure differential is created between the first and second faces of the sensor array, and a processor configured to receive the response generated by the one or more first sensors and to process the response to detect at least one analyte in a fluid flow. The sensor array includes one or more first sensors and one or more fluid channels extending from the first face to the second face. At least one of the first sensors is located at a first position in the sensor array in contact with the first face of the sensor array. The sensors are configured to generate a response upon exposure of the sensor array to at least one analyte in a fluid flow.

Particular implementations of the invention can include one or more of the following features. The sensor array can include a substrate having a first surface and a second surface. The fluid channels can extend from the first surface to the second surface. The fluid channels can include a plurality of pores in a microporous substrate material, or a plurality of holes introduced into an impermeable substrate material. The fluid flow system can include a predetermined sampling volume, with the sensor array located within the sampling volume. The first sensor can have a sensor volume substantially optimized to cause the first sensor to generate a response having a maximum signal to noise ratio for at least one target analyte. The sensor volume can be substantially optimized as a function of a partition coefficient K of at least one target analyte. The predetermined sampling volume can include a headspace proximate to the first sensor, the headspace having a headspace volume $V_f$. The sensor volume $V_p$ can be substantially optimized based on the function $V_p=V_f/K$. The first sensors can include one, or multiple, vapor sensors for detecting an analyte in a gas. The first sensors can include one, or multiple, liquid sensors for detecting an analyte in a liquid.

The sensor array can include at least one second sensor located at a second position in the sensor array. The second position can be different from the first position relative to the fluid flow. The first and second sensors can each generate a response upon exposure of the sensor array to at least one analyte in a fluid flow, such that the responses generated upon exposure of the sensor array to at least one analyte in a fluid flow include a spatio-temporal difference between the responses for the first and second sensors. The processor can be configured to resolve a plurality of analytes in a fluid flow upon exposure of the sensor array to a fluid flow containing the plurality of analytes. The sensor array can include a plurality of second sensors. Each of the first sensor and a plurality of the second sensors can be located at a different position in the sensor array relative to the fluid flow. The first and second sensors can each generate a response upon exposure of the sensor array to at least one analyte in a fluid flow, such that the responses generated upon exposure of the sensor array to at least one analyte in a fluid flow include a spatio-temporal difference between the responses for the first and second sensors.

The sensor array can include a first substrate forming a plate having a length, a width, and a depth, such that the length and the width in combination define a pair of substrate faces and the width and the depth in combination define a pair of substrate edges. The first substrate can be oriented in the sampling volume such that the substrate faces extend in a direction parallel to a direction of the fluid flow and the substrate edges are situated normal to the fluid flow. The first sensors can be located on one of the pair of substrate edges. The sensor array can include one or more second sensors located on one of the pair of substrate faces.

The processor can be configured to resolve a plurality of analytes in a fluid flow upon exposure of the sensor array to a fluid flow containing the plurality of analytes. The sensor array can include a plurality of second sensors located at different positions along one of the pair of substrate faces, such that the responses generated upon exposure of the sensor array to at least one analyte in a fluid flow include a spatio-temporal difference between responses generated by each of the first and the plurality of the second sensors. The sensor array can include a plurality of substrates, each substrate forming a plate having a length, a width, and a depth, such that for each of the substrates the length and the width in combination define a pair of substrate faces and the width and the depth in combination define a pair of substrate edges. The substrates can be oriented in the sampling volume such that the substrate faces extend in a direction parallel to a direction of the fluid flow and the substrate edges are situated normal to the fluid flow. For each of the plurality of substrates, the sensor array can include one or more first sensors located on one of the pair of substrate edges and one or more second sensors located on at least one of the pair of substrate faces. At least one of the first sensor or the second sensors can have a sensor volume substantially optimized to achieve a maximum signal to noise ratio for at least one target analyte. The sensor volume can be substantially optimized as a function of a partition coefficient K of at least one target analyte. The predetermined sampling volume can include a headspace proximate to the first sensor, the headspace having a headspace volume $V_f$. The sensor volume $V_p$ can be substantially optimized based on the function $V_p=V_f/K$. The first sensors can include one, or multiple, vapor sensors for detecting an analyte in a gas. The first sensors can include one, or multiple, liquid sensors for detecting an analyte in a liquid.

In general, in another aspect, the invention features methods for detecting an analyte in a fluid flow. The methods include providing a sensor array having a first face and a second face and including one or more first sensors, exposing the sensor array to a fluid flow including an analyte under conditions sufficient to create a pressure differential between the first and second faces of the sensor array, measuring a response for the first sensors, and detecting the presence of the analyte in the fluid based on the measured response. The sensor array includes one or more fluid channels extending from the first face to the second face. At least one of the first sensors is located at a first position in the sensor array in contact with the first face of the sensor array. The first sensors are configured to generate a response upon exposure of the sensor array to at least one analyte in a fluid flow.

Particular implementations of the invention can include one or more of the following features. The sensor array can include a substrate having a first surface and a second surface. The fluid channels can extend from the first surface to the second surface. The fluid channels can include a plurality of pores in a microporous substrate material, or a plurality of holes introduced into an impermeable substrate material. The fluid flow system can include a predetermined sampling volume, with the sensor array located within the sampling volume. The first sensor can have a sensor volume substantially optimized to cause the first sensor to generate a response having a maximum signal to noise ratio for at least one target analyte. The sensor volume can be substantially optimized as a function of a partition coefficient K of at least one target analyte. The predetermined sampling volume can include a headspace proximate to the first sensor, the headspace having a headspace volume $V_l$. The sensor volume $V_p$ can be substantially optimized based on the function $V_p=V_l/K$. The first sensors can include one, or multiple, vapor sensors for detecting an analyte in a gas. The first sensors can include one, or multiple, liquid sensors for detecting an analyte in a liquid.

The sensor array can include at least one second sensor located at a second position in the sensor array. The second position can be different from the first position relative to the fluid flow. The first and second sensors can each generate a response upon exposure of the sensor array to at least one analyte in a fluid flow, such that the responses generated upon exposure of the sensor array to at least one analyte in a fluid flow include a spatio-temporal difference between the responses for the first and second sensors. Detecting the presence of the analyte in the fluid can include resolving a plurality of analytes in the fluid based on the measured response. The sensor array can include a plurality of second sensors. Each of the first sensor and a plurality of the second sensors can be located at a different position in the sensor array relative to the fluid flow. The first and second sensors can each generate a response upon exposure of the sensor array to at least one analyte in a fluid flow, such that the responses generated upon exposure of the sensor array to at least one analyte in a fluid flow include a spatio-temporal difference between the responses for the first and second sensors.

The sensor array can include a first substrate forming a plate having a length, a width, and a depth, such that the length and the width in combination define a pair of substrate faces and the width and the depth in combination define a pair of substrate edges. The first substrate can be oriented in the sampling volume such that the substrate faces extend in a direction parallel to a direction of the fluid flow and the substrate edges are situated normal to the fluid flow. The first sensors can be located on one of the pair of substrate edges. The sensor array can include one or more second sensors located on one of the pair of substrate faces. Detecting the presence of the analyte in the fluid includes resolving a plurality of analytes in the fluid based on the measured response. The sensor array can include a plurality of second sensors located at different positions along one of the pair of substrate faces, such that the responses generated upon exposure of the sensor array to at least one analyte in a fluid flow include a spatio-temporal difference between responses generated by each of the first and the plurality of the second sensors. The sensor array can include a plurality of substrates, each substrate forming a plate having a length, a width, and a depth, such that for each of the substrates the length and the width in combination define a pair of substrate faces and the width and the depth in combination define a pair of substrate edges. The substrates can be oriented in the sampling volume such that the substrate faces extend in a direction parallel to a direction of the fluid flow and the substrate edges are situated normal to the fluid flow. For each of the plurality of substrates, the sensor array can include one or more first sensors located on one of the pair of substrate edges and one or more second sensors located on at least one of the pair of substrate faces. At least one of the first sensor or the second sensors can have a sensor volume substantially optimized to achieve a maximum signal to noise ratio for at least one target analyte. The sensor volume can be substantially optimized as a function of a partition coefficient K of at least one target analyte. The predetermined sampling volume can include a headspace proximate to the first sensor, the headspace having a headspace volume $V_l$. The sensor volume $V_p$ can be substantially optimized based on the function $V_p=V_l/K$. The first sensors can include one, or multiple, vapor sensors for detecting an analyte in a gas. The first sensors can include one, or multiple, liquid sensors for detecting an analyte in a liquid.

In general, in another aspect, the invention features sensor arrays for detecting an analyte in a fluid. The sensor arrays include one or more substrates and one or more sensors in contact with the substrates. Each substrate has a first surface. The sensors are configured to generate a response upon exposure of the sensor array to at least one analyte in a fluid. Each sensor has a sensor volume. The sensor volume for at least one of the sensors is substantially optimized to cause the first sensor to generate an optimized response upon exposure of the sensor array to at least one target analyte.

Particular implementations of the invention can include one or more of the following features. The sensor volume can be substantially optimized as a function of a sampling headspace volume $V_l$ and a partition coefficient K of at least one target analyte. The sensor volume $V_p$ can be substantially optimized based on the function $V_p=V_l/K$. The sensors can include two or more optimized sensors. Each of the optimized sensors can be substantially optimized to generate an optimized response upon exposure of the sensor array to a different target analyte. The optimized response can have a substantially maximized signal to noise ratio.

In general, in another aspect, the invention features sensor arrays for detecting an analyte in a fluid flow. The sensor arrays include a substrate having a first surface and a second surface, one or more sensors in contact with the first surface, and one or more fluid channels extending from the first surface to the second surface. The sensors are configured to generate a response upon exposure of the sensor array to at least one analyte in a fluid flow.

Particular implementations of the invention feature one or more of the following features. The fluid channels can be configured such that upon introduction of a fluid flow to the sensor array a pressure differential is created between the first and second surfaces of the substrate. The substrate can include a microporous material or an impermeable material. The fluid channels can include a plurality of pores in the substrate, or a plurality of holes introduced into the substrate. The sensors can include one, or multiple, vapor sensors for detecting an analyte in a gas. The sensors can include one, or multiple, liquid sensors for detecting an analyte in a liquid.

In general, in still another aspect, the invention features sensor arrays having a first face and a second face for detecting an analyte in a fluid flow. The sensor arrays include one or more substrates, each substrate forming a plate having a length, a width, and a depth, such that the length and the width in combination define a pair of substrate faces and the width and the depth in combination define a first substrate edge and a second substrate edge; a plurality of sensors configured to generate a response upon exposure of the sensor array to at least one analyte in a fluid flow; and one or more fluid channels extending along one or more of the substrate faces from the first face of the array to the second face of the array. The first substrate edge for each of the substrates is aligned with the first face of the array. The sensors include one or more first sensors sensors and one or more second sensors. Each of the first sensors is located along one of the first substrate edges. Each of the second sensors is located along one of the substrate faces.

Particular implementations can include one or more of the following features. The sensors include a plurality of second sensors located at different positions along at least one of the pair of substrate faces, such that the responses generated upon exposure of the sensor array to at least one analyte in a fluid flow include a spatio-temporal difference between responses generated by each of the first and the plurality of the second sensors. The sensors include one, or multiple, vapor sensors for detecting an analyte in a gas. The sensors include one, or multiple, liquid sensors for detecting an analyte in a liquid.

In general, in still another aspect, the invention features methods of fabricating a sensor array for detecting an analyte in a fluid. The methods include providing a substrate having a surface and a sampling headspace proximate to the surface; identifying a sampling headspace volume $V_t$ for at least a portion of the sampling headspace, and a partition coefficient K of at least one target analyte in a sensing material; calculating a sensor volume based on the sampling headspace volume and the partition coefficient; and fabricating a sensor on the surface proximate to the at least a portion of the sampling headspace, the sensor including an amount of the sensing material derived from the calculated sensor volume. In particular implementations, the sensor volume $V_p$ can be calculated based on the function $V_p=V_t/K$.

BRIEF DESCRIPTION OF THE DRAWINGS

FIGS. 4A and 4B illustrate a flow-through sensor system incorporating the perforated array such as is shown in FIG. 3.

FIG. 10 is a table showing responses, noise, and S/N for two types of polymer-carbon black composite detectors in the configuration of FIG. 5A.

DETAILED DESCRIPTION OF THE INVENTION

Figure 1A:
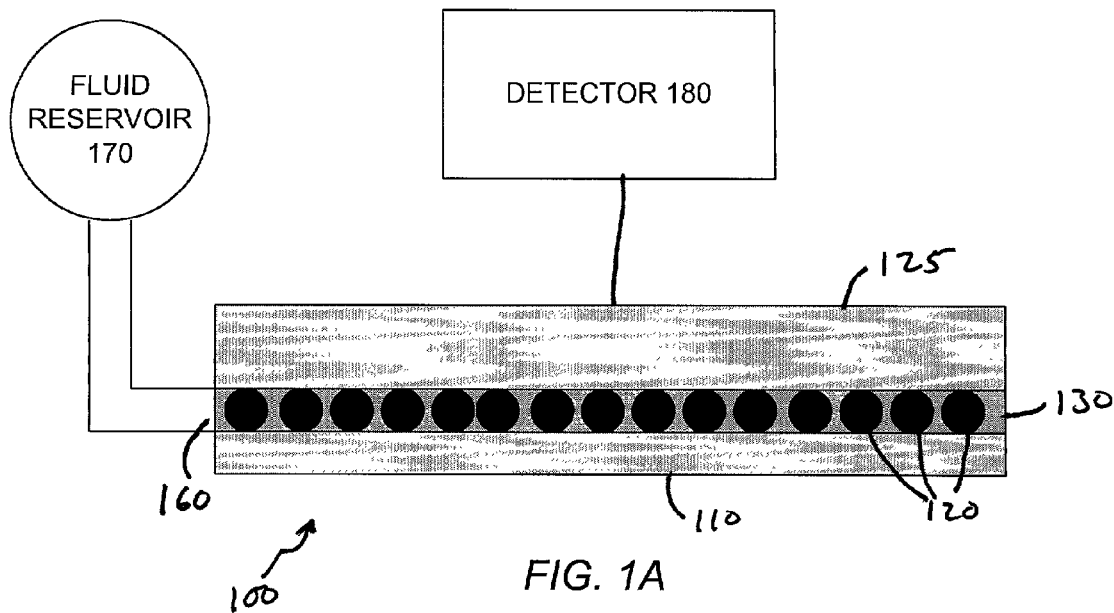
FIG. 1 illustrates one implementation of a system involving a linear sensor array for detecting an analyte in a fluid.
Figure 1B:
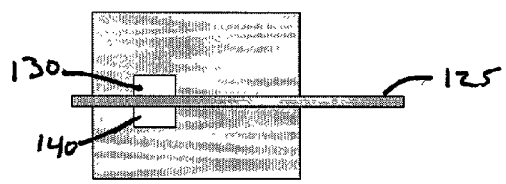
Figure 1C:
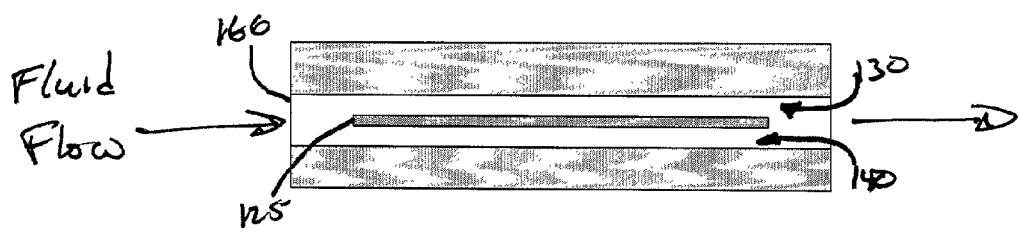

FIGS. 1A, 1B and 1C illustrate one example of a system 100 for detecting an analyte in a fluid. System 100 includes a sensor array 110, including a plurality of sensors 120 arranged on a substrate 125 along a fluid channel 130. In some implementations, sensor array 110 may be configured to include one or more fluid channels in addition to fluid channel 130, such as fluid channel 140 including additional sensors arranged along the same or a different substrate. A fluid to be analyzed, which may be in gaseous or liquid form, is introduced to sensor array 110 through fluid inlet 160, for example from fluid reservoir 170. Response signals from the sensors 120 in sensor array 110 resulting from exposure of the fluid to the sensor array are received and processed in detector 180, which may include, for example, signal-processing electronics, a general-purpose programmable digital computer system of conventional construction, or the like.

Sensors 120 can include sensors of any of a variety of known types, including, for example, surface acoustic wave sensors, quartz crystal resonators, metal oxide sensors, dye-coated fiber optic sensors, dye-impregnated bead arrays, micromachined cantilever arrays, vapochromic metalloporphyrins, composites having regions of conducting material and regions of insulating organic material, composites having regions of conducting material and regions of conducting or semiconducting organic material, chemically-sensitive resistor or capacitor films, metal-oxide-semiconductor field effect transistors, bulk organic conducting polymeric sensors, and other known sensor types. Techniques for constructing arrays of such sensors are known, as disclosed in Harsanyi, G., Polymer Films in Sensor Applications (Technomic Publishing Co., Basel, Switzerland, 1995), and U.S. Pat. Nos. 6,017,440, 6,013,229 and 5,911,872 and co-pending U.S. patent application Ser. No. 09/409,644, filed Oct. 1, 1999, which are incorporated by reference herein. Techniques for fabricating particular sensor types are disclosed in Ballantine, et al., Anal. Chem. 1986, 58, 3058; Grate, et al., Sens. Actuators B 1991, 3, 85; Grate, et al., Anal. Chem. 1993, 65, 1868; Nakamoto, et al., Sens. Actuators B 1993, 10, 85 (surface acoustic wave (SAW) devices), Gardner, et al., Sens. Actuators B 1991, 4, 117; Gardner, et al., Sens. Actuators B 1992, 6, 71; Corcoran, et al., Sens. Actuators B 1993, 15, 32 (tin oxide sensors), Shurmer, et al., Sens. Actuators B 1991, 4, 29; Pearce, et al., Analyst 1993, 118, 371 (conducting organic polymers), Freund, et al., Proc. Natl. Acad. Sci. 1995, 92, 2652 (materials having regions of conductors and regions of insulating organic material), White, et al., Anal. Chem. 1996, 68, 2191 (dye-impregnated polymer films on fiber optic sensors), Butler, et al., Electrochem. Soc. 1990, 137, 1325; Hughes, et al., Biochem. and Biotechnol. 1993, 41, 77 (polymer-coated micromirrors), Slater, et al., Analyst 1994, 119, 191; Slater, et al., Analyst 1991, 116, 1125 (quartz crystal microbalances (QCMs)), Keyvani, et al., Sens. Actuators B 1991, 5, 199 (electrochemical gas sensors), Zubkans, et al., Thin Solid Films 1995, 268, 140 (chemically sensitive field-effect transistors) and Lonergan, et al., Chem. Mater. 1996, 8, 2298 carbon black-polymer composite chemiresistors). Additional sensor array fabrication techniques are disclosed in Albert, K. J., et al., Chem. Rev., 2000, 100, 2595–2626 and the references cited therein.

In one implementation, sensor array 110 incorporates multiple sensing modalities, for example comprising a spatial arrangement of cross-reactive sensors 120 selected from known sensor types, such as those listed above, such that a given analyte elicits a response from multiple sensors in the array and each sensor responds to many analytes. Preferably, the sensors in the array 110 are broadly cross-reactive, meaning each sensor in the array responds to multiple analytes, and, in turn, each analyte elicits a response from multiple sensors.

Sensor arrays allow expanded utility because the signal for an imperfect "key" in one channel can be recognized through information gathered on another, chemically or physically dissimilar channel in the array. A distinct pattern of responses produced over the collection of sensors in the array can provide a fingerprint that allows classification and identification of the analyte, whereas such information would not have been obtainable by relying on the signals arising solely from a single sensor or sensing material. By developing an empirical catalogue of information on chemically diverse sensors—made, for example, with varying ratios of semiconducting, conducting, and insulating components and by differing fabrication routes—sensors can be chosen that are appropriate for the analytes expected in a particular application, their concentrations, and the desired response times. Further optimization can then be performed in an iterative fashion as feedback on the performance of an array under particular conditions becomes available.

In some implementations, the sensor arrays of system 100 incorporate spatiotemporal response information that is used by detector 180 to aid in analyte detection and identification. The incorporation of data derived from spatio-temporal properties of a sensor array can impart useful information on analyte detection and identification relative to arrays where no spatiotemporal information is available because all sensors are nominally in identical positions with respect to the fluid flow characteristics and are exposed to the analyte at nominally identical times during the fluid sampling experiment. Electronics can be implemented in detector 180 to record a time delay between sensor responses and to use this information to characterize the analyte of interest in the fluid. This mode can also be advantageous because it can allow automatic nulling of any sensor drift, environmental variations (such as temperature, humidity, etc.) and the like. Also, a complex analyte mixture can be better resolved into its components based on the spatiotemporal characteristics of the array response relative only to the differences in fingerprints on the various sensors types in the array. Additionally, the method can be used in conjunction with differential types of measurements to selectively detect only certain classes or types of analytes, because the detection can be gated to only focus on signals that exhibit a desired correlation time between their responses on the sensors that are in different exposure times relative to the sensor response on the first sensor that detects an analyte.

Thus, for example, sensor arrays 110 can be configured such that low vapor pressure analytes in the gas phase will have a high affinity towards the sensors and will sorb strongly to them. This strong sorption produces a strong response at the first downstream sensor that the analyte encounters, a weaker response at the second downstream sensor, and a still weaker response at other downstream sensors. Different analytes will produce a detectable and useful time delay between the response of the first sensor and the response of the other downstream sensors. As a result, detector 180 can use the differences in response time and amplitude to detect and characterize analytes in a carrier fluid, analogous to the use of gas chromatography retention times, which are well known in the gas chromatography literature and art.

Spatio-temporal information can be obtained from an array of two or more sensors by varying the sensors' exposure to the fluid containing the analyte across the array (e.g., by generating a spatial and/or temporal gradient across the array), thereby allowing responses to be measured simultaneously at various different exposure levels and for various different sensor compositions. For example, an array can be constructed in two dimensions with sensors arranged at the vertices of a grid or matrix. Such arrays can be configured to vary the composition of the sensors in the horizontal direction across the array, such that sensor composition in the vertical direction across the array remains constant. One may then create a spatio-temporal gradient in the vertical direction across the array—for example, by introducing the fluid from the top of the array and providing for fluid flow vertically down the array, thereby allowing the simultaneous analysis of chemical analytes at different sensor compositions and different exposure levels. Similarly, in an array 110 including a plurality of different sensors 120 (i.e., an array in which each sensor is of a different type or composition), spatio-temporal variation can be introduced by systematically varying the flow rate at which the analyte-containing fluid is exposed to the sensors in the array. Again, in this implementation, measuring the response of each of the sensors 120 at a variety of different flow rates allows the simultaneous analysis of analytes at different sensor compositions and different exposure levels.

Thus, in one implementation, the sensors defining each fluid channel are nominally identical—that is, the sensors within a given fluid channel are identical—while the array incorporates a predetermined inter-sensor variation in the chemistry, structure or composition of the sensors between different fluid channels. The variation can be quantitative and/or qualitative. For example, different channels can be constructed to incorporate sensors of different types, such as incorporating a plurality of nominally identical metal oxide gas sensors in a first fluid channel, a plurality of conducting polymer sensors in an adjacent fluid channel, and so on across the array. Alternatively, compositional variation can be introduced by varying the concentration of a conductive or semiconductive organic material in a composite sensor across fluid channels. In still another variation, a variety of different organic materials may be used in sensors in different channels. Similar patterns of introducing compositional variation into sensor arrays will be readily apparent to those skilled in the art.

Figure 2:
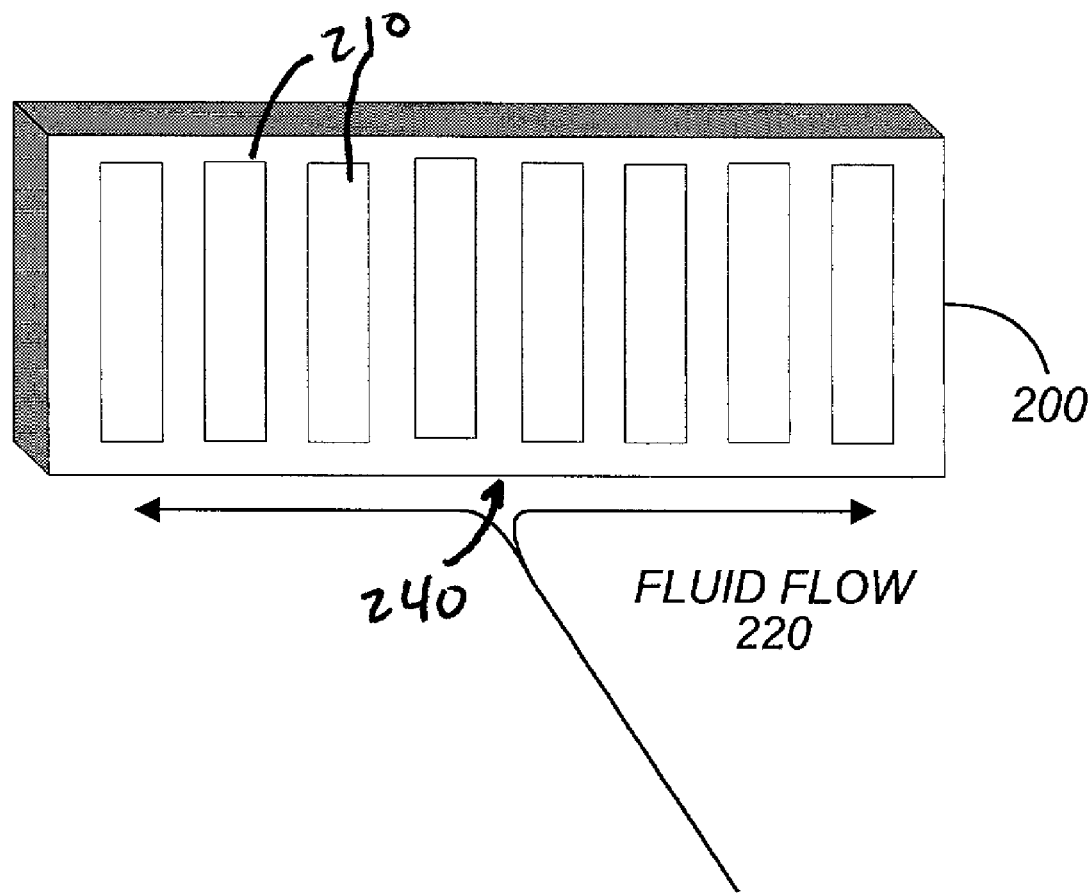
FIG. 2 illustrates a two-dimensional implementation of a sensor array for detecting an analyte in a fluid.

Although FIG. 1A depicts the fluid channels as linear channels extending in just one direction, sensor arrays can be configured to provide similar fluid channels having different geometries—for example, arrays with sensors arranged in two or more directions relative to the fluid flow, such as a circular array having a radial arrangement of sensors around a fluid introduction point. FIG. 2 illustrates a simply sensor array of this type—an array 200 of eight sensors 210. A stream 220 of fluid containing an analyte or analytes of interest is directed at surface 230, such that the stream contacts surface 230 at point 240, and then flows radially in both directions across the array.

While sensor array 110 has been described as incorporating one or more fluid channels each comprising a plurality of nominally identical sensors, those skilled in the art will recognize that the techniques described herein can be used to generate useful spafio-temporal information from arrays including a plurality of sensors all of different chemistry, structure or composition, with the fluid path being defined by the introduction of the fluid onto the array. In this implementation, spatio-temporal response data can be generated by introducing the fluid onto the array at varying flow rates, for example, by using a flow controller of known construction to systematically vary the rate at which the fluid is introduced over time. Alternatively, flow rate variation can be introduced by simply exposing the array to a naturally varying fluid flow, such as a flow of air.

In some implementations, system 100 provides that an analyte (e.g., a gas analyte) can be directed through or to substrate 125 by including gaps or pores into the substrate or by using a substrate that itself is porous and highly permeable to the analyte of interest. Application of a pressure differential between the top and bottom of the substrate allows the gas to be effectively sampled by the detectors (e.g., a sensor film deposited on substrate 125), enhancing the detection sensitivity of the entire sensor device and system.

Figure 3:
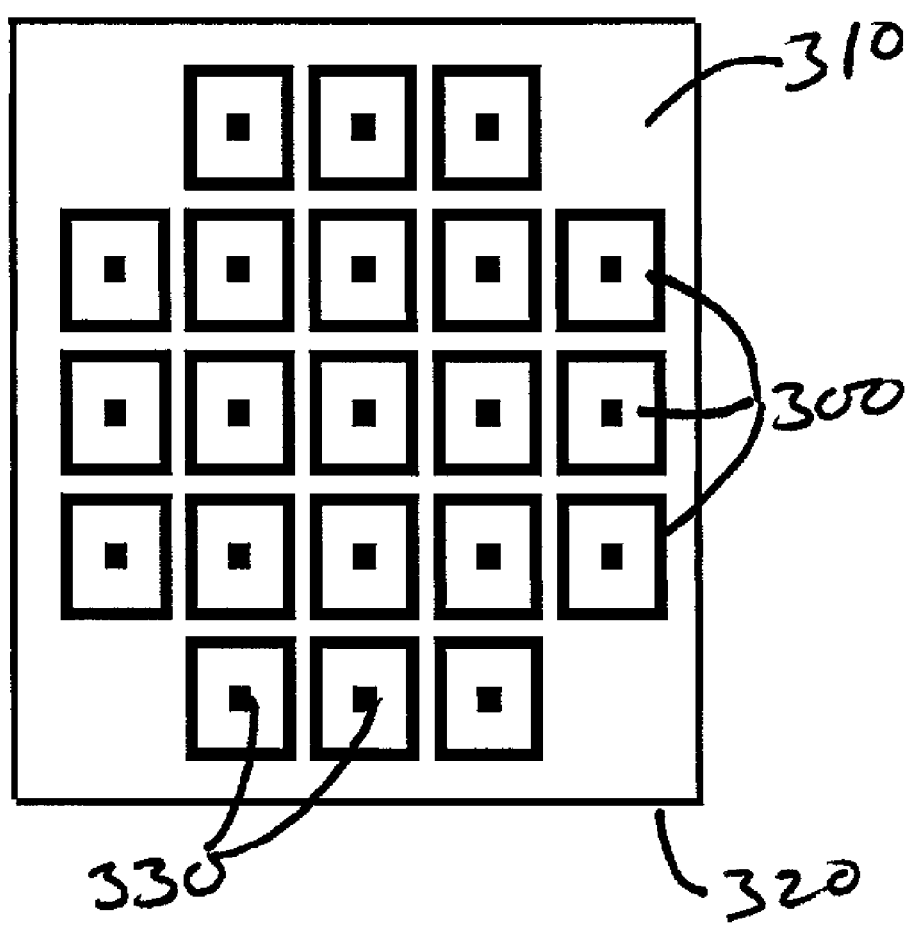
FIG. 3 illustrates one implementation of a perforated two-dimensional sensor array.
Figure 4B:
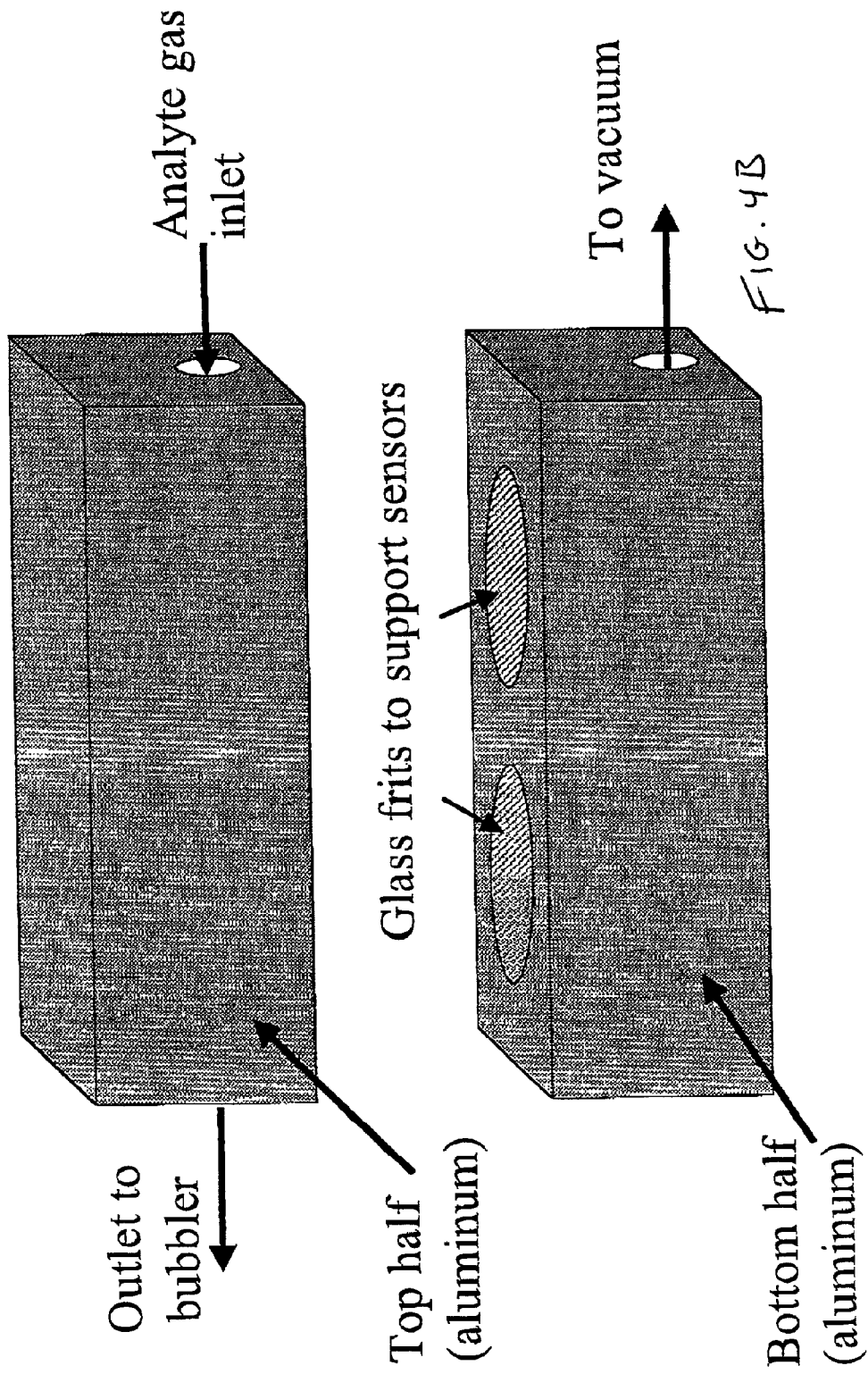

In one implementation, illustrated in FIG. 3, sensors 300 are arranged on a surface 310 of porous substrate 320 such that a fluid containing the analyte or analytes of interest strikes surface 310, interacts with sensors 300, and flows through pores 330. Sensors 300 can be fabricated as a sensor film deposited on top of substrate 320. As illustrated in FIG. 4A, a pressure differential can be established between the two sides 410 and 420 of a perforated or porous substrate 400 in order to direct the analyte to flow through the sensor film, optimizing analyte sorption and detection performance, as opposed to merely flowing nearby or parallel to the surface of a solid substrate 430. One example of a flow-through apparatus incorporating such a perforated substrate is illustrated in FIG. 4B. A variety of different substrates, with a variety of different porosities can be used.

Substrate 320 can be fabricated from a material that is not highly permeable by the analyte gas of concern, such as printed circuit board, ceramic, or a silicon wafer. In this embodiment, pores 330 can take the form of a series of holes introduced into the substrate at well-defined positions and spacings. Hole density, hole diameter and/or sensor size can be optimized for a given analyte flow rate, analyte gas/solid partition coefficient, and analyte permeability into the sensor film, in order to allow the maximum amount of analyte to be captured by the sensor film during its flow by the sensor and sensor substrate.

For analytes having low vapor pressure (and high partition coefficients), larger detector areas will produce a dilution of the available analyte into larger detector volumes, thereby producing less resistance change in such detector films. Because the sensor response scales linearly with the concentration of sorbed analyte, whereas the noise scales as the square root of the detector film area (for constant film thickness), this favors smaller detector areas.

Thus, for low vapor pressure analytes, a preferred a flow-through detector configuration incorporates roughly 2–25% open area (98%–75% solidity, with the exact value depending on the analyte's partition coefficient into the polymer film) for analyte detection. Simulations of detectors having 1% open area suggest that the capture effectiveness of the perforated plate arrangement scales with the flow Reynolds number. However, the capture effectiveness can be bounded from below by 50% for Reynolds numbers up to 100, which can correspond to the limiting case of a detector with one or two holes and an open area of 1–2%. It may be sufficient to have enough holes to ensure even flow into the detector. Significant improvements over this design (up to ~90% analyte capture) can be expected when the Reynolds number is on the order of 1 (very many small holes, e.g., approximately 1 µm in diameter spaced at, e.g., 12 µm intervals). Micro-machining methods may be required to satisfy these dimensions.

Alternatively, substrate 320 can be fabricated from a material that is porous to analyte flow. The porosity can be introduced through physical or chemical processes. Two such examples are Anopore alumina membranes and Nucleopore polymer membranes. As described above, optimum pore structure and pore distribution can be computed for certain specific conditions of analyte flow velocity, gas/polymer sorption coefficient, and other sensor and sensor parameters.

In a preferred implementation, the porous substrate is a microporous, branched-pore Anopore membrane having 200 nm diameter pores extending from one face through most of the membrane thickness, branching to 20 nm diameter pores in a narrow layer (e.g., 500 nm in a 60 micron membrane) at the opposite face. Sensors are deposited as thin films on this face (on top of conductive contacts deposited on the surface) using techniques such as those described below. The branched-pore membrane structure ensures that the detector face presents pores of a sufficiently small diameter to limit seepage of the sensor media into the membrane (e.g., excluding carbon black particles in a polymer-carbon black composite film as described below having particle sizes ranging from about 20 nm to about 50 nm), while also providing for a high fluid flux to the sensor film.

Figure 5A:
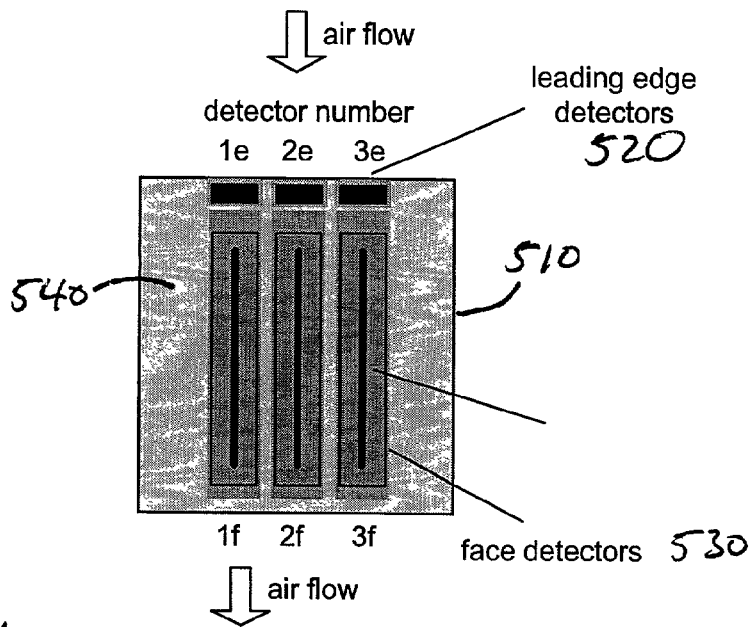
FIGS. 5A and 5B illustrate an implementation of a system for detecting an analyte in a fluid involving a stacked sensor array.
Figure 5B:
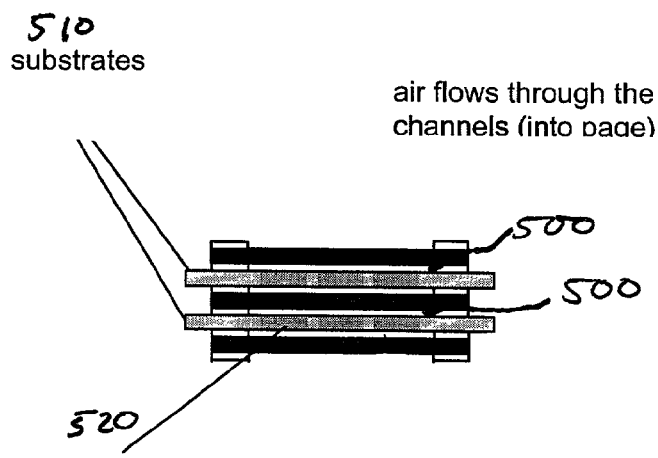

In another implementation, illustrated in FIGS. 5A and 5B, the holes/pores can be replaced by their one-dimensional analog—linear or non-linear channels or gaps 500 in spacing through plates 510 that contain sensors on their edges 520. The performance of this type of system can also be computed using well-known equations for specific sensor/substrate conditions. In some instances, this type of structure can be easier to manufacture than one with holes in the substrate. In addition, this type of structure offers the opportunity to introduce additional sensors 530 on the faces 540 of the stacked substrates, offering an opportunity to make measurements on sensor films placed both on the edges of the substrates as well as at various positions and in various geometries on the faces of the substrates. Measurement of the response at various positions on the substrate in this type of geometry permits the parallel analysis of vapors that possess different optimal sorption and/or detection regions on the sensor material in the presence of the flow onto and around the stacked substrates.

The incorporation of different form factors of a given detector film in conjunction with specific types of analyte flow paths can provide very different detection performance for different types of analyte vapors. Accordingly, as will be described in more detail below, the use of an array of detectors that are nominally identical chemically, but which have different form factors relative to the analyte flow path, can provide useful information on the composition and identity of an analyte vapor. In addition, the arrangement of FIGS. 5A and 5B offers a simple means to differentiate between target analytes and background contaminants, even where the contaminants are present at significantly higher concentration than the target analyte, as will be described in more detail below.

In some implementations, the form factor of the sensors in the array can be manipulated to optimize the signal to noise output of the system, yielding one or more sensors having optimal, or near-optimal, sensor volumes for one or more target analytes. At open circuit, resistors exhibit voltage fluctuations—known as Johnson noise—whose power spectrum is constant as the frequency is varied. The root mean squared (rms) noise voltage density of the Johnson noise, $V_{JN}$, is related to the resistance, R, of a resistive detector as follows:

$$V_{JN} = (4kTRB)^{1/2} \quad (1)$$

where k is Boltzmann's constant, T is the temperature in degrees K, and B is the bandwidth (Wilmshurst, T. H., *Signal Recovery from Noise in Electronic Instrumentation*; Adam Hilger Ltd: Boston, 1985). This Johnson noise is the fundamental lower limit on the noise of any device of resistance R, and its magnitude is independent of the volume or of other fabrication-dependent properties of the resistor. However, when current flows through most types of resistive materials, a voltage fluctuation is observed with a power spectral density that displays an inverse dependence on frequency. This additional noise, which is typically of the form $1/f^\gamma$ where $\gamma = 1 \pm 0.1$, is designated 1/f noise (Larry, et al., *IEEE Trans. Comp. Hybrids, Manufact. Technol.* 1980, CHMT-3, 211–225; Weissman, M. B. *Rev. Mod. Phys.* 1988, 60, 537–571).

Even for a series of resistors that are fabricated by an identical process, the magnitude of the 1/f noise depends on the volume, V, of the resistor. When the correlation length of the resistive particle network is small compared to the physical length scale of interest, the 1/f noise of a resistance-based detector is expected to be proportional to $V^{-1/2}$ (Dziedzic, et al., *J. Phys. D-Appl. Phys.* 1998, 31, 2091–2097). For a given film thickness, this implies that the total noise of a resistive detector scales as $A^{-1/2}$, where A is the total area of the detector film between the electrical contact leads. This dependence requires that the magnitude of the 1/f noise, in the frequency window of the measurement, is much greater than the magnitude of the Johnson noise, so that the total noise is dominated by the 1/f contribution.

As a consequence of Ohm's law, the power spectral density, $S_n(V)$, of the 1/f resistance noise scales with the square of the bias voltage, $V_b$, applied to the resistor. The quantity of fundamental interest in characterizing the noise of a resistive detector element is thus:

$$S_n = S_n(V_b)/V_b^2 \quad (2)$$

where $S_n$ is the relative noise power spectral density and $V_b$ is the biasing voltage (Dziedzic, et al., J. Phys. D-Appl. Phys. 1998, 31, 2091–2097; Scofield, et al., Phys. Rev. B 1981, 24, 7450–7453). In contrast to the Johnson noise, the level of the 1/f noise in carbon black polymer composite resistors varies with many factors, including the structure of the carbon black, its volume fraction in the composite, the type of insulator, the resistivity of the composite, and the method of resistor preparation (Dziedzic, et al., J. Phys. D-Appl. Phys. 1998, 31, 2091–2097; Fu, et al., IEEE Trans. Comp. Hybrids Manufact. Technol. 1981, 4, 283–288).

Figure 6:
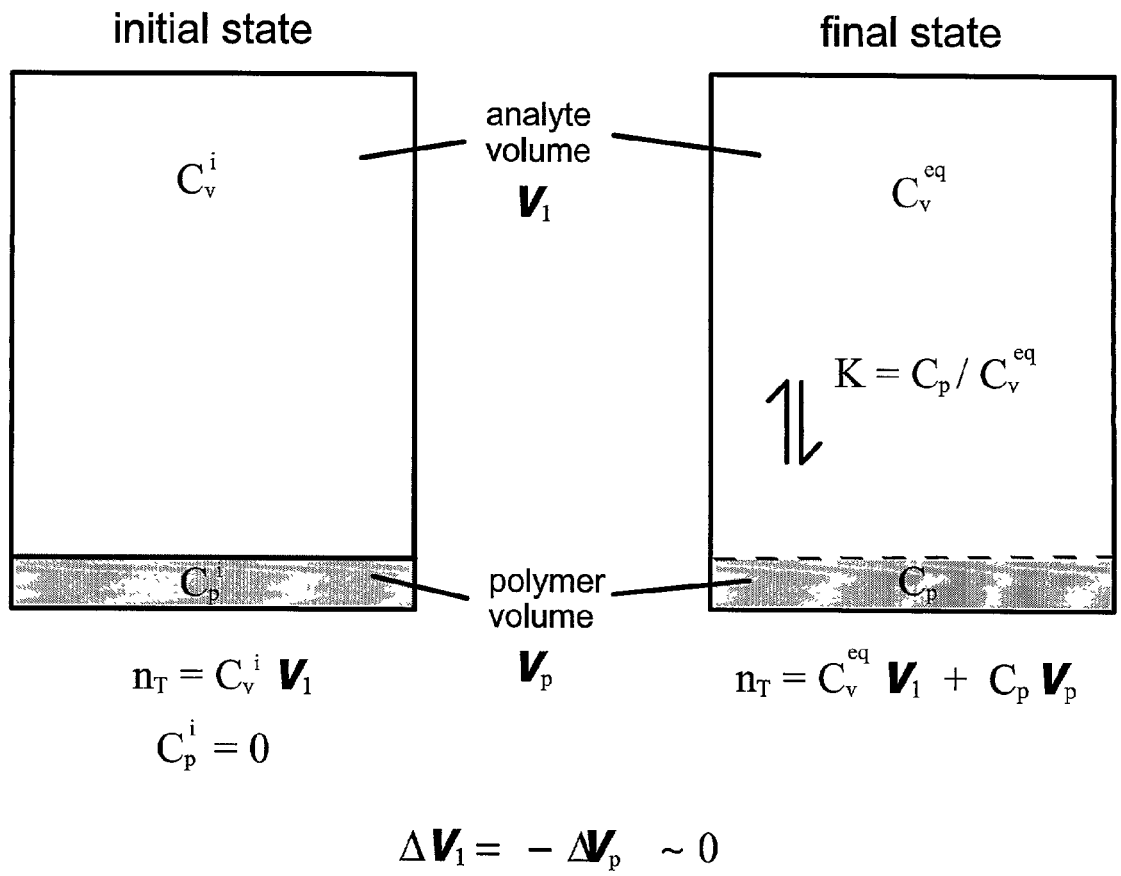
FIG. 6 is a diagram illustrating the equilibration between a finite volume of sampled analyte and a finite volume of sorption-based vapor detection film in a sensor array according to the invention.

The dependence of the signal produced by sorption of an analyte on the volume of the detector film can be determined as follows. Consider introducing a fixed quantity of an analyte into a sample chamber of total volume $V_I$ to produce an initial analyte concentration $C_v^i$ in the vapor phase, as illustrated in FIG. 6. The analyte can either be introduced as a pulse of concentrated analyte into the volume $V_I$ or by introducing a sampled volume of analyte in conjunction with a dead volume of carrier gas in the sampling path such that initially after the sampling process has been completed, an analyte concentration $C_v^i$ is present in a total headspace volume $V_I$. Assuming that no analyte is present initially in either the background gas or the polymer, the total number of moles of analyte available for sorption into the polymer is therefore $n_T = C_v^i V_I$. Sorption of the analyte into a polymer of volume $V_p$ will proceed with a polymer/gas partition coefficient, $K = C_p/C_v^{eq}$, where $C_p$ is the concentration of analyte in the polymer phase, $C_v^{eq}$ is the concentration of the analyte in the vapor phase, and both concentrations refer to the situation after equilibrium has been reached.

For typical detector film thicknesses of 0.2–1.0 μm, and for typical headspace thicknesses of greater than 0.1 cm, even 100% increases in film thickness due to sorption-induced film swelling will produce a negligible change in the headspace volume. Assuming that the change in volume of the polymer phase due to analyte sorption, $\Delta V_p$, is generally small compared to the value of the initial headspace volume $V_I$ implies that $V_I$ also equals the headspace volume after equilibrium has been reached. Under these conditions, conservation of mass of analyte implies that:

$$n_T = V_I C_v^i = V_p C_p + V_I C_v^{eq} \quad (3)$$

Hence $$n_T = V_p C_p + V_I C_p / K \quad (4)$$

or $$C_p n_T / (V_p + V_I / K) \quad (5)$$

It can be further assumed (Albert, et al., Chem. Rev. 2000, 100, 2595–2626) that the signal, S, obtained due to sorption of analyte into the polymer is linearly related to the sorbed analyte concentration through a sensitivity factor, $X_1$, for each analyte/polymer combination:

$$S = X_1 C_p \quad (6)$$

In the limit where the 1/f noise dominates the total noise of a chemically sensitive resistor, this measurement noise, N, scales as $V^{-1/2}$ (vide supra). It follows that:

$$N = X_2 V_p^{-1/2} \quad (7)$$

where $X_2$ is a constant that is independent of the film volume.

The signal/noise is therefore:

$$S/N = X_1 C_p / X_2 V_p^{-1/2} \quad (8)$$

Substituting for $C_p$ from Equation 5, above, produces:

$$S/N = (X_1/X_2) n_T [V_p^{1/2} + (V_f/K) V_p^{-1/2}]^{-1} \quad (9)$$

Multiplying both the numerator and denominator of the right hand side of Equation 9 by $(K/V_f)^{1/2}$ yields:

$$S/N = (X_1/X_2) n_T (K/V_f)^{1/2} [(V_f/K)^{-1/2} V_p^{1/2} + (V_f/K)^{1/2} V_p^{-1/2}]^{-1} \quad (10)$$

With the substitution $x = V_p K/V_f$, Equation 10 becomes:

$$S/N = (X_1/X_2) n_T (K/V_f)^{1/2} [x^{1/2} + x^{-1/2}]^{-1} \quad (11)$$

This function is maximized when x=1, i.e., when $K V_p/V_f = 1$, which implies that:

$$V_p = V_f/K \quad (12)$$

at maximal S/N ratio.

When $V_p = V_f/K$, Equations 3 and 4 yield $C_v^{eq} V_f = (\frac{1}{2}) n_T$ and $C_p V_p = (\frac{1}{2}) n_T$. In other words, for a finite quantity of sampled analyte, the maximal S/N ratio is obtained when the detector volume equals the headspace volume $V_f$ divided by the polymer/gas partition coefficient. This produces a situation in which equal numbers of moles of analyte are present in the polymer and vapor phases after equilibrium has been attained.

In practice, the film thickness of the detector is typically as small as possible to minimize the time constant for sorbtion/desorbtion of analyte. Hence, at constant, minimized film thickness, Equations 9 and 12 imply that there is an optimum detector film area for a given headspace volume and a given initial headspace analyte concentration. Smaller detector areas than this optimum value fail to exhibit optimally low noise, while larger detector areas result in the sorption of the fixed number of moles of analyte into too large of a polymer volume and therefore produce a reduced magnitude of signal after equilibrium has been reached. Another consequence of this analysis is that the different response properties of a set of detectors having a common polymer sorbent layer, but having different form factors, can provide information on the value of K, if $V_f$ is known and/or is held constant during the experiment. The validity of these predictions has been confirmed for sorption-based detectors fabricated using carbon black-filled chemiresistors as exemplary systems, as will be described in more detail below.

In implementations employing sensors comprised of carbon black-polymer composite chemiresistors, sensor performance, measured as the baseline normalized differential resistance change ($\Delta R/R_b$) is linearly dependent on analyte concentration over a range of analyte/detector combinations and analyte concentrations (Severin, et al., Anal. Chem. 2000, 72, 658–668). Detection limits for such sensors can be estimated based on noise measurements, in conjunction with the dependence of $\Delta R/R_b$ on the partial pressure of the analyte (Doleman, et al., Proc. Natl. Acad. Sci. U.S.A. 1998, 95, 5442–5447), and the analyte/polymer sensitivity factors that can be deduced from such plots. Two limiting cases are illustrative: a) high vapor pressure analytes, which have relatively small partition coefficients for sorption into the carbon black composite detectors, and b) low vapor pressure analytes, which generally sorb strongly and exhibit very large polymer/gas partition coefficients into the polymers of concern.

When the polymer/gas partition coefficient is relatively small, sufficient analyte will, in general, be present in the sampled volume to produce the equilibrium volume swelling of the entire available detector area. In this situation, too little detector volume is generally present to satisfy the optimum detector volume as given by Equation 12. At constant film thickness, the steady-state $\Delta R/R_b$ value of a given carbon black/polymer composite is directly related to the swelling change of the film. Thus, a given analyte concentration should produce the same steady-state $\Delta R/R_b$ signal in the film regardless of the area of such a detector.

Under these conditions, the scaling of the S/N (in a given measurement bandwidth) with detector area is determined by the dependence of the noise on detector area. As discussed above, the background noise of the carbon black composite chemiresistors at low measurement frequencies scales as $A^{-1/2}$. The S/N, and thus the detection limits of a particular carbon black polymer composite detector towards a given analyte, therefore scale as $A^{1/2}$. The use of a detector film having the largest practical volume possible (up to the limit of optimum volume indicated by Equation 12, or the volume at which the 1/f noise, for the measurement bandwidth, falls below the Johnson noise and the total noise no longer exhibits a dependence on volume) is thus the optimum detector design under such conditions.

S/N values and deduced limits of detection for representative carbon black/polymer composite detectors with various vapor analytes, for 1 $cm^2$ of detector area are illustrated in Table 1, in which limits of detection are calculated from the slopes of $\Delta R/R_b$ vs. $P/P^o$ at 294 K as described in Severin, et al., Anal. Chem. 2000, 72, 658–668, using $3\sigma$ noise values for 1 $cm^2$ of the same film type at average experimental film thickness values of 230 nm for PEVA and 80 nm for PCL.

TABLE 1

Limits of Detection for Carbon Black Polymer Composite Detectors and Polymer Film SAW Detectors

| | polymer | LOD (µg/L) | | | |
|---|---|---|---|---|---|
| | | benzene | cyclohexanone | hexane | nonane |
| Carbon Black Composite | PEVA | $1.8 \times 10^1$ | 1.5 | $4.0 \times 10^1$ | 1.3 |
| | PCL | $5.2 \times 10^2$ | $4.5 \times 10^1$ | $1.3 \times 10^3$ | $4.8 \times 10^1$ |
| SAW | poly[bis(cyanoallyl)siloxane] | $4.0 \times 10^2$ | $1.5 \times 10^1$ | $5.3 \times 10^3$ | $5.7 \times 10^2$ |
| | poly(methylphenylsiloxane) | $3.0 \times 10^2$ | $1.4 \times 10^1$ | $1.5 \times 10^3$ | $1.1 \times 10^2$ |

TABLE 1-continued

Limits of Detection for Carbon Black Polymer Composite Detectors and Polymer Film SAW Detectors

| | LOD (µg/L) | | | |
|---|---|---|---|---|
| polymer | benzene | cyclohexanone | hexane | nonane |
| poly(phenyl ether) | $2.2 \times 10^2$ | $1.3 \times 10^1$ | $9.9 \times 10^2$ | $7.9 \times 10^1$ |
| poly(isobutylene) | $2.6 \times 10^2$ | $3.2 \times 10^1$ | $3.5 \times 10^2$ | $1.9 \times 10^1$ |

Table 1 also reports representative values taken from the literature for selected polymer-coated SAW vapor detectors for 158-MHz SAW oscillators at 298 K (Patrash, et al., Anal. Chem. 1993, 65, 2055–2066). For the given area, the detection limits are comparable for both types of signal transduction, although the carbon black composites exhibit somewhat higher sensitivity than the SAW devices for the analyte/polymer combinations chosen for comparison. Table 1 reports only limits of detection as opposed to limits of classification; the former quantity depends only on the properties of the analyte/detector combination, while the latter quantity also depends on the test set of analytes presented to the array as well as on the algorithms used to perform the classification. As reported by Zellers, et al., Anal. Chem. 1998, 70, 4191–4201, in at least one instance, the limit of classification of an analyte has been shown to be within a factor of three of the limit of detection of that same analyte, indicating that the limit of classification is likely to be on the same order of magnitude as the limit of detection, at least for some tasks.

In the limit where the analyte exhibits a very strong sorption into the polymer film of the carbon black composite detector, a different S/N optimization methodology applies. As given by Equation 5, the sorption process under such conditions will be limited by the amount of analyte in the sampled volume. The $\Delta R/R_b$ signal of the detector is proportional to the swelling change of the detector film (Severin, et al., Anal. Chem. 2000, 72, 2008–2015), so increasing the detector area will reduce the signal (by diluting the fixed amount of sorbed analyte into a correspondingly larger volume of polymer). As long as the swelling is linearly dependent on the concentration of analyte sorbed into the polymer, this dilution will produce a linear decrease in the $\Delta R/R_b$ signal with increased detector volume. Because the noise scales as $A^{-1/2}$ (at constant film thickness), the S/N under such conditions scales as $A^{-1/2}$ and small detector areas are favored. The design goal under such conditions is to insure that the most analyte is sorbed into the least area of detector film, and signals should only be acquired from the limited, highly analyte-swollen, portion of the detector. This principle is exemplified in the detector arrangement of FIGS. 5A and 5B.

This relationship also has implications for sample chamber design of vapor detector arrays. Assuming, for example, that the analyte headspace is comprised of a vertical column equal in area to the area of the detector film, and that the detector film thickness is $1.0 \times 10^{-4}$ cm, for analytes having a partition coefficient $K=1.0 \times 10^2$, the sorbed analyte will come to equilibrium with the vapor phase analyte that is contained in a headspace thickness of $1.0 \times 10^{-2}$. In this instance, increasing the thickness of the headspace provides more analyte than is needed to attain the optimal S/N ratio for the detector response and requires introduction of more sample into the headspace chamber. Alternatively, under these circumstances larger detector areas can be used advantageously to obtain improved S/N ratios from the increased number of analyte molecules available in a thicker headspace chamber. In contrast, for $K=1.0 \times 10^7$, a $1.0 \times 10^{-4}$ cm thick detector film will sorb essentially all of the analyte from a 1000 cm thick headspace. A 2.6 cm² area of such a detector film could sorb essentially all of the analyte in a $3.0 \times 10^{-2}$ cm thick headspace that is supplied at a continuous volumetric flow rate of 10 cm³ min⁻¹ for a period of 260 min. For shorter analyte injection times (at constant analyte flow rate), smaller detector areas are optimal because otherwise the fixed amount of analyte is distributed into too large a detector area, thereby diminishing the magnitude of the signal and deleteriously affecting the S/N ratio of the detector.

Given the reported relationships between the mass loading of analyte and the $\Delta R/R_b$ values for carbon black composite vapor detectors (Severin, et al., Anal. Chem. 2000, 72, 2008–2015), in conjunction with the background noise levels reported herein, detection limits can be evaluated in the high sorption/low analyte vapor pressure regime. At a noise level of ≈10 ppm, and with a $\Delta R/R_b=0.10$ produced at a mass loading of 5.0 µg of analyte sorbed into 1 cm² of polymer, the computed 3σ detection limit of a PCL-carbon black composite is 1.5 ng cm⁻². This value can only be reached in practice if an efficient sampling and delivery system is available, such that the full amount of the sampled analyte can be delivered effectively to the 1 cm² area of the detector film. Of note is that the detection limit scales inversely with the film area and linearly with the efficiency of delivering analyte to the sampled film area.

In the intermediate sorption/partition coefficient regime, an optimum detector volume exists for which the S/N, and therefore the detection limit performance, of a particular analyte/polymer combination is maximized. This detector volume, and consequently the optimum film area, depends only on the analyte/polymer partition coefficient and the sampled analyte volume, and can be calculated from Equation 12. The S/N can therefore be optimized for different vapor pressure analytes through control over the form factor of the detector film. Those skilled in the art will recognize that the use of these techniques to prepare sensors, sensor arrays, and sampling systems having substantially optimal, or near-optimal, form factors does not depart from the invention.

The dependence of optimum detector area on the analyte/polymer partition coefficient can also be used advantageously in the classification of analytes and analyte mixtures. In such a system, analytes with a high polymer/gas partition coefficient (generally analytes with low vapor pressures) would be sorbed into the smallest detector area possible, producing the largest signal and therefore the largest S/N ratio for that particular analyte/polymer/sampler combination. Higher vapor pressure analytes are, in turn, detected with higher S/N performance at detectors having larger film areas. Thus, an array of contacts spaced exponentially along a polymer film can be used advantageously to gain information on the sorption coefficients of analytes into polymers, and therefore can provide additional classification information on analytes and analyte mixtures relative only to equilibrium $\Delta R/R_b$ values on a detector film having a single, fixed form factor for all analytes. Additional information is available if the analyte flow rate is also varied over the detector array. Variation in the geometric form factor of detectors can also provide practical advantages in the implementation of instruments based on arrays of vapor detectors. Although information similar to that produced by a collection of spatiotemporally arrayed detectors could in principle be obtained from an analysis of the time response of a collection of detectors that are equivalent both geometrically and with respect to the point of analyte injection, the spatiotemporal implementation discussed above has the advantage that analytes are detected on films that have nearly optimal S/N for the analyte of interest. In addition, electronically referencing the response of a face detector to that of an edge detector, for example, allows nulling of the response to a high vapor pressure analyte and subsequent amplification of only those signals arising from low vapor pressure analytes. Finally, deliberate variation in the analyte flow rate can be used to encode the analyte signal at higher frequencies, and use of a lock-in amplifier centered at this higher frequency (where the magnitude of the 1/f noise is lower than at dc) would enhance the S/N of these detectors.

The sensors and sensor arrays disclosed herein can act as "electronic noses" to offer ease of use, speed, and identification of analytes and/or analyte regions all in a portable, relatively inexpensive implementation. Thus, a wide variety of analytes and fluids may be analyzed by the disclosed sensors, arrays and noses so long as the subject analyte is capable generating a differential response across a plurality of sensors of the array. Analyte applications include broad ranges of chemical classes such as organics including, for example, alkanes, alkenes, alkynes, dienes, alicyclic hydrocarbons, arenes, alcohols, ethers, ketones, aldehydes, carbonyls, carbanions, biogenic amines, thiols, polynuclear aromatics and derivatives of such organics, e.g., halide derivatives, etc., biomolecules such as sugars, isoprenes and isoprenoids, fatty acids and derivatives, etc. Accordingly, commercial applications of the sensors, arrays and noses include environmental toxicology and remediation, biomedicine, materials quality control, food and agricultural products monitoring, anaesthetic detection, automobile oil or radiator fluid monitoring, breath alcohol analyzers, hazardous spill identification, explosives detection, fugitive emission identification, medical diagnostics, fish freshness, detection and classification of bacteria and microorganisms both in vitro and in vivo for biomedical uses and medical diagnostic uses, monitoring heavy industrial manufacturing, ambient air monitoring, worker protection, emissions control, product quality testing, leak detection and identification, oil/gas petrochemical applications, combustible gas detection, $H_2S$ monitoring, hazardous leak detection and identification, emergency response and law enforcement applications, illegal substance detection and identification, arson investigation, enclosed space surveying, utility and power applications, emissions monitoring, transformer fault detection, food/beverage/agriculture applications, freshness detection, fruit ripening control, fermentation process monitoring and control applications, flavor composition and identification, product quality and identification, refrigerant and fumigant detection, cosmetic/perfume/fragrance formulation, product quality testing, personal identification, chemical/plastics/pharmaceutical applications, leak detection, solvent recovery effectiveness, perimeter monitoring, product quality testing, hazardous waste site applications, fugitive emission detection and identification, leak detection and identification, perimeter monitoring, transportation, hazardous spill monitoring, refueling operations, shipping container inspection, diesel/gasoline/aviation fuel identification, building/residential natural gas detection, formaldehyde detection, smoke detection, fire detection, automatic ventilation control applications (cooking, smoking, etc.), air intake monitoring, hospital/medical anesthesia & sterilization gas detection, infectious disease detection and breath applications, body fluids analysis, pharmaceutical applications, drug discovery, telesurgery, and the like. Another application for the sensor-based fluid detection device in engine fluids is an oil/antifreeze monitor, engine diagnostics for air/fuel optimization, diesel fuel quality, volatile organic carbon measurement (VOC), fugitive gases in refineries, food quality, halitosis, soil and water contaminants, air quality monitoring, leak detection, fire safety, chemical weapons identification, use by hazardous material teams, explosive detection, breathalyzers, ethylene oxide detectors and anaesthetics.

Biogenic amines such as putrescine, cadaverine, and spermine are formed and degraded as a result of normal metabolic activity in plants, animals and microorganisms, and have been identified and quantified using analytical techniques such as gas chromatography-mass spectrometry (GC-MS), high performance liquid chromatography (HPLC) or array based vapor sensing in order to assess the freshness of foodstuffs such as meats (Veciananogues, 1997, J. Agr. Food Chem., 45:2036–2041), cheeses, alcoholic beverages, and other fermented foods. Additionally, aniline and o-toluidine have been reported to be biomarkers for subjects having lung cancer (Preti et al., 1988, J. Chromat. Biomed. Appl. 432:1–11), while dimethylamine and trimethylamine have been reported to be the cause of the "fishy" uremic breath odor experienced by patients with renal failure.(Simenhoff, 1977, New England J. Med., 297:132–135) Thus, in general biogenic amines and thiols are biomarkers of bacteria, disease states, food freshness, and other odor-based conditions. Thus, the electronic nose sensor elements and arrays discussed herein can be used to monitor the components in the headspace of urine, blood, sweat, and saliva of human patients, as well as breath, to diagnose various states of health and disease. In addition, they can be used for food quality monitoring, such as fish freshness (which involves volatile amine signatures), for environmental and industrial applications (oil quality, water quality, air quality and contamination and leak detection), for other biomedical applications, for law enforcement applications (breathalyzers), for confined space monitoring (indoor air quality, filter breakthrough, etc) and for other applications delineated above to add functionality and performance to sensor arrays through improvement in analyte detection by use in arrays that combine sensor modalities. For example, surface acoustic wave (SAW) arrays, quartz crystal microbalance arrays, composites consisting of regions of conductors and regions of insulators, bulk semiconducting organic polymers, and other array types exhibit improved performance towards vapor discrimination and quantification when designed according to the invention by directing the analyte through, towards or increase contact of the analyte with a sensor (e.g., wherein the array of sensors comprises a member selected from the group consisting of a metal oxide gas sensor, a conducting polymer sensor, a dye-impregnated polymer film on fiber optic detector, a polymer-coated micromirror, an electrochemical gas detector, a chemically sensitive field-effect transistor, a carbon black-polymer composite, a micro-electro-mechanical system device and a micro-opto-electro-mechanical system device).

Breath testing has long been recognized as a nonintrusive medical technique that might allow for the diagnosis of disease by linking specific volatile organic vapor metabolites in exhaled breath to medical conditions (see Table 2). In addition to breath analysis being nonintrusive, it offers several other potential advantages in certain instances, such as 1) breath samples are easy to obtain, 2) breath is in general a much less complicated mixture of components than either serum or urine samples, 3) direct information can be obtained on the respiratory function that is not readily obtainable by other means, and 4) breath analysis offers the potential for direct real time monitoring of the decay of toxic volatile substances in the body. Table 2 lists some of the volatile organic compounds that have been identified as targets for specific diseases using gas chromatography/mass spectrometry (GC/MS) methods, with emphasis on amines.

TABLE 2

| Patient Diagnosis | Target VOCs | VOC Source |
|---|---|---|
| Uremia; Preti, 1992; Simenhoff, 1977; Davies, 1997 | dimethylamine, trimethylamine | breath, urine |
| Trimethylaminuria; Preti, 1992; Alwaiz, 1989 | trimethylamine | breath, urine, sweat, vaginal discharge |
| Lung Cancer; Preti, 1992 | aniline, o-toluidine | lung air |
| Dysgeusia/Dysosmia; Preti, 1992; Oneill, 1988 | hydrogen sulfide, methyl mercaptan, pyridine, aniline, diphenylamine, dodecanol | lung air |
| Cystinuria; Manolis A., 1983, Clin. Chem. 29:5. | cadaverine, piperidine, putrescine, pyrrolidine | breath |
| Halitosis; Kozlovsky, 1994; Preti, 1992 | hydrogen sulfide, methyl mercaptan, cadaverine, putrescine, indole, skatole | mouth air |
| Bacterial Vaginosis; Chandiok, 1997, J. Clinical Path., 50:790. | amines | vaginal cavity and discharge |

The invention is described with reference to resistive sensors. Although the invention is described with reference to chemical resistive sensors other types of sensors are applicable to the invention including, for example, heated metal oxide thin film resistors, polymer sorption layers on the surfaces of acoustic wave resonators, arrays of electrochemical detectors, conductive polymers or composites that consist of regions of conductors and regions of insulating organic materials and quartz crystal microbalance arrays.

The sensors and sensor arrays comprise a plurality of differently responding chemical sensors. In one embodiment, the array has at least one sensor comprising at least a first and second conductive lead electrically coupled to and separated by a chemically sensitive resistor. The leads may be any convenient conductive material, usually a metal, and may be interdigitized to maximize signal-to-noise strength.

In a conductive sensor array (other types of sensor may be used), the array is composed of a material comprising regions of an organic electrical conductor with regions of a compositionally dissimilar material that is an electrical conductor. The conductive sensor forms a resistor comprising a plurality of alternating regions of differing compositions and therefore differing conductivity transverse to the electrical path between the conductive leads. Generally, at least one of the sensors is fabricated by blending a conductive material with a conductive organic material. For example, in a colloid, suspension or dispersion of particulate conductive material in a region of conductive organic material, the regions separating the particles provide changes in conductance relative to the conductance of the particles themselves. The gaps of different conductance arising from the organic conductive material range in path length from about 10 to 1,000 angstroms, usually on the order of 100 angstroms. The path length and resistance of a given gap is not constant but rather is believed to change as the material absorbs, adsorbs or imbibes an analyte. Accordingly the dynamic aggregate resistance provided by these gaps in a given resistor is a function of analyte permeation of the conductive organic regions of the material. In some embodiments, the conductive material may also contribute to the dynamic aggregate resistance as a function of analyte permeation (e.g., when the conductive material is a conductive organic polymer such as polypyrrole and is blended with another organic conducting material to form the composite).

A wide variety of conductive materials and dissimilar conductive organic materials can be used. In one embodiment, one such region is comprised of an inorganic (Au, Ag) or organic (carbon black) conductive material, while the other region is comprised of a compositionally dissimilar organic conducting polymer (polyaniline, polypyrrole, polythiophene, polyEDOT, and other conducting organic polymers such as those identified in the Handbook of Conducting Polymers (Handbook of Conducting Polymers, second ed., Marcel Dekker, New York 1997, vols. 1 & 2)). Other combinations of conductor/organic conductor/composite materials are also useful.

In one implementation, an electrically conductive organic material that is dopable or undopable by protons can be used as the organic material in a composite where the compositionally different conductor is carbon black.

Polyaniline is a desirable member in the class of conducting polymers in that the half oxidized form, the emeraldine base (y=0.5), is rendered electrically conductive upon incorporation of a strong acid. The conductive form of polyaniline, commonly referred to as the emeraldine salt (ES), has been reported to deprotonate to the emeraldine base and become insulating in alkaline environments.

Conductive materials for use in sensor fabrication can include, for example: organic conductors, such as conducting polymers (e.g., poly(anilines), poly(thiophenes), poly(pyrroles), poly(aceylenes), etc.), carbonaceous material (e.g., carbon blacks, graphite, coke, C60, etc.), charge transfer complexes (tetramethylparaphenylenediamine-chloranile, alkali metal tetracyanoquinodimethane complexes, tetrathiofulvalene halide complexes, etc.), and the like; inorganic conductors, such as metals/metal alloys (e.g., Ag, Au, Cu, Pt, AuCu alloy, etc.), highly doped semiconductors (e.g., Si, GaAs, InP, $MoS_2$, $TiO_2$, etc.), conductive metal oxides (e.g., $In_2O_3$, $SnO_2$, $Na_2Pt_3O_4$, etc.), superconductors (e.g., $YBa_2Cu_3O_7$, $Ti_2Ba_2Ca_2Cu_3O_{10}$, etc.), and the like; and mixed inorganic/organic conductors, such as tetracyanoplatinate complexes, iridium halocarbonyl complexes, stacked macrocyclic complexes, and the like. Blends, such as of those listed, may also be used. Typically conductors include, for example, those having a positive temperature coefficient of resistance. The sensors are comprised of a plurality of alternating regions of a conductor with regions of a compositionally dissimilar conducting organic material. Without being bound to any particular theory, it is believed that the electrical pathway that an electrical charge traverses between the two contacting electrodes traverses both the regions of the conductor and the regions of the organic material. In these embodiments, the conducting region can be anything that can carry electrons from atom to atom, including, but not limited to, a material, a particle, a metal, a polymer, a substrate, an ion, an alloy, an organic material, (e.g., carbon, graphite, etc.) an inorganic material, a biomaterial, a solid, a liquid, a gas or regions thereof In certain other embodiments, the conductive material is a conductive particle, such as a colloidal nanoparticle. As used herein the term "nanoparticle" refers to a conductive cluster, such as a metal cluster, having a diameter on the nanometer scale. Such nanoparticles are optionally stabilized with organic ligands. Examples of colloidal nanoparticles for use in accordance with the present invention are described in the literature. In this embodiment, the electrically conductive organic region can optionally be a ligand that is attached to a central core making up the nanoparticle. These ligands i.e., caps, can be polyhomo- or polyheterofunctionalized, thereby being suitable for detecting a variety of chemical analytes. The nanoparticles, i.e., clusters, are stabilized by the attached ligands. In certain embodiments, the conducting component of the resistors are nanoparticles comprising a central core conducting element and an attached ligand optionally in a polymer matrix. With reference to Table 2, various conducting materials are suitable for the central core. In certain preferred embodiments, the nanoparticles have a metal core. Typical metal cores include, but are not limited to, Au, Ag, Pt, Pd, Cu, Ni, AuCu and mixtures thereof. These metallic nanoparticles can be synthesized using a variety of methods. In a one method of synthesis, a modification of the protocol developed by Brust et al. can be used. (see, Brust, M.; Walker, M.; Bethell, D.; Schiffrin, D. J.; Whyman, R. J. Chem. Soc., Chem. Commun., 1994, 801–802.) As explained more fully below, by varying the concentration of the synthetic reagents, the particle size can be manipulated and controlled.

The conductive organic material can be either an organic semiconductor or organic conductor. "Semi-conductors" as used herein, include materials whose electrical conductivity increases as the temperature increases, whereas conductors are materials whose electrical conductivity decreases as the temperature increases. By this fundamental definition, organic materials that are useful in some embodiments of the sensors of the present invention are either semiconductors or conductors. Such materials are collectively referred to herein as electrically conducting organic materials because they produce a readily-measured resistance between two conducting leads separated by about 10 micron or more using readily-purchased multimeters having resistance measurement limits of 100 Mohm or less, and thus allow the passage of electrical current through them when used as elements in an electronic circuit at room temperature. Semiconductors and conductors can be differentiated from insulators by their different room temperature electrical conductivity values. Insulators show very low room temperature conductivity values, typically less than about $10^{-8}$ ohm$^{-1}$ cm$^{-1}$. Poly(styrene), poly(ethylene), and other polymers provide examples of insulating organic materials. Metals have very high room temperature conductivities, typically greater than about 10 ohm$^{-1}$ cm$^{-1}$. Semi-conductors have conductivities greater than those of insulators, and are distinguished from metals by their different temperature dependence of conductivity, as described above. The organic materials that are useful in an embodiment of the sensors of the invention are either electrical semiconductors or conductors, and have room temperature electrical conductivities of greater than about $10^{-6}$ ohm$^{-1}$ cm$^{-1}$, typically having a conductivity of greater than about $10^{-3}$ ohm$^{-1}$ cm$^{-1}$.

Accordingly, the sensors of the invention can include sensors comprising regions of an electrical conductor and regions of a compositionally different organic material that is an electrical conductor or semiconductor. As used above, electrical conductors include, for example, Au, Ag, Pt and carbon black, other conductive materials having similar resistivity profiles are easily identified in the art (see, for example the latest edition of: The CRC Handbook of Chemistry and Physics, CRC Press, the disclosure of which is incorporated herein by reference). Furthermore, insulators can also be incorporated into the composite to further manipulate the analyte response properties of the composites. The insulating region (i.e., non-conductive region) can be anything that can impede electron flow from atom to atom, including, but not limited to, a material, a polymer, a plasticizer, an organic material, an organic polymer, a filler, a ligand, an inorganic material, a biomaterial, a solid, a liquid, a gas and regions thereof. Insulating organic materials that can be used for such purposes can include, for example: main-chain carbon polymers, such as poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitrites), poly(vinyl esters), poly(styrenes), poly(aryines), and the like; main-chain acyclic heteroatom polymers, such as poly (oxides), poly(caronates), poly(esters), poly(anhydrides), poly(urethanes), poly(sulfonate), poly(siloxanes), poly(sulfides), poly(thioesters), poly(sulfones), poly(sulfonamindes), poly(amides), poly(ureas), poly(phosphazens), poly(silanes), poly(silazanes), and the like; and main-chain heterocyclic polymers, such as poly(furantetracarboxylic acid diimides), poly(benzoxazoles), poly(oxadiazoles), poly (benzothiazinophenothiazines), poly(benzothiazoles), poly (pyrazinoquinoxalines), poly(pyromenitimides), poly(quinoxalines), poly(benzimidazoles), poly(oxidoles), poly (oxoisinodolines), poly(diaxoisoindoines), poly(triazines), poly(pyridzaines), poly(pioeraziness), poly(pyridines), poly (pioeridiens), poly(triazoles), poly(pyrazoles), poly(pyrrolidines), poly(carboranes), poly(oxabicyclononanes), poly (diabenzofurans), poly(phthalides), poly(acetals), poly (anhydrides), carbohydrates, and the like.

Nonconductive organic polymer materials; blends and copolymers; plasticized polymers; and other variations including those using the polymers listed here, may also be used. Combinations, concentrations, blend stoichiometries, percolation thresholds, etc. are readily determined empirically by fabricating and screening prototype resistors (chemiresistors) as described below.

The chemiresistors can be fabricated by many techniques such as, but not limited to, solution casting, suspension casting, and mechanical mixing. In general, solution cast routes are advantageous because they provide homogeneous structures and ease of processing. With solution cast routes, sensor elements may be easily fabricated by spin, spray or dip coating. Suspension casting still provides the possibility of spin, spray or dip coating but more heterogeneous structures than with solution casting are expected. With mechanical mixing, there are no solubility restrictions since it involves only the physical mixing of the resistor components, but device fabrication is more difficult since spin, spray and dip coating are no longer possible.

For systems where both the conducting, compositionally dissimilar organic conducting and non-conducting material or their reaction precursors are soluble in a common solvent, the chemiresistors can be fabricated by solution casting. The oxidation of pyrrole by phosphomolybdic acid represents such a system. In this reaction, the phosphomolybdic acid and pyrrole are dissolved in tetrahydrofuran (THF) and polymerization occurs upon solvent evaporation. This allows for THF soluble compositionally different conductive, semiconductive, and non-conductive materials to be dissolved into this reaction region thereby allowing the composite to be formed in a single step upon solvent evaporation.

A variety of permutations on this scheme are possible for other conducting polymers. Some of these are listed below. Certain conducting organic polymers, such as substituted poly-(cyclooctatetraenes), are soluble in their undoped, non-conducting state in solvents such as THF or acetonitrile. Consequently, the blends between the undoped polymer and other organic materials can be formed from solution casting. After which, the doping procedure (exposure to $I_2$ vapor, for instance) can be performed on the blend to render the substituted poly(cyclooctatetraene) conductive. Again, the choice of compositionally different organic materials is limited to those that are soluble in the solvents that the undoped conducting polymer is soluble in and to those stable to the doping reaction.

Certain conducting organic polymers can also be synthesized via a soluble precursor polymer. In these cases, blends between the precursor polymer and the compositionally different material of the composite can first be formed followed by chemical reaction to convert the precursor polymer into the desired conducting polymer. For instance poly(p-phenylene vinylene) can be synthesized through a soluble sulfonium precursor. Blends between this sulfonium precursor and a non-conductive or conductive polymer can be formed by solution casting. After which, the blend can be subjected to thermal treatment under vacuum to convert the sulfonium precursor to the desired poly(p-phenylene vinylene).

In suspension casting, one or more of the components of the sensor is suspended and the others dissolved in a common solvent. Suspension casting is a rather general technique applicable to a wide range of species, such as carbon blacks or colloidal metals, which can be suspended in solvents by vigorous mixing or sonication. In one application of suspension casting, the conductive organic or conductive polymer is dissolved in an appropriate solvent (such as THF, acetonitrile, water, etc.). Carbon black is then suspended in this solution and the resulting region is used to dip coat or spray coat electrodes.

Mechanical mixing is suitable for all of the conductive/conductive organic/non-conductive combinations possible. In this technique, the materials are physically mixed in a ball-mill or other mixing device. For instance, carbon black/conducting organic polymer composites are readily made by ball-milling. When the semiconductive or conductive organic material can be melted or significantly softened without decomposition, mechanical mixing at elevated temperature can improve the mixing process. Alternatively, composite fabrication can sometimes be improved by several sequential heat and mix steps.

Once fabricated, the individual sensors can be optimized for a particular application by varying their chemical make up and morphologies. The chemical nature of the sensors determines to which analytes they will respond and their ability to distinguish different analytes. The relative ratio of conductive to compositionally different organic conductive or semiconductive organic material, along with the composition of any other insulating organic or inorganic components, can determine the magnitude of the response since the resistance of the elements becomes more sensitive to sorbed molecules as the percolation threshold is approached and as the molecules interact chemically with the components of the composite that adsorb or absorb the analyte. The film morphology is also important in determining response characteristics. For instance, uniform thin films respond more quickly to analytes than do uniform thick ones. However, it may be advantageous to include sensors of varying thickness to determine various diffusion coefficients or other physical characteristics of the analyte being analyzed. Hence, with an empirical catalogue of information on chemically diverse sensors made with varying ratios of semiconductive, conducting, and insulating components and by differing fabrication routes, sensors can be chosen that are appropriate for the analytes expected in a particular application, their concentrations, and the desired response times. Further optimization can then be performed in an iterative fashion as feedback on the performance of an array under particular conditions becomes available.

The resistor may itself form a substrate for attaching the lead or the resistor. For example, the structural rigidity of the resistors may be enhanced through a variety of techniques: chemical or radiation cross-linking of polymer components (dicumyl peroxide radical cross-linking, UV-radiation cross-linking of poly(olefins), sulfur cross-linking of rubbers, e-beam cross-linking of Nylon, etc.), the incorporation of polymers or other materials into the resistors to enhance physical properties (for instance, the incorporation of a high molecular weight, high melting temperature ($T_m$)polymers), the incorporation of the resistor elements into supporting matrices such as clays or polymer networks (forming the resistor blends within poly-(methylmethacrylate) networks or within the lamellae of montmorillonite, for instance), etc. In another embodiment, the resistor is deposited as a surface layer on a solid matrix which provides means for supporting the leads. As described above, these supporting matrices can be porous or permeable to certain analytes across which a pressure difference is created to effectuate analyte contact with the sensor.

Sensor arrays particularly well suited to scaled up production are fabricated using integrated circuit (IC) design technologies. For example, the chemiresistors can easily be integrated onto the front end of a simple amplifier interfaced to an A/D converter to efficiently feed the data stream directly into a neural network software or hardware analysis section. Micro-fabrication techniques can integrate the chemiresistors directly onto a micro-chip which contains the circuitry for analog signal conditioning/processing and then data analysis. This provides for the production of millions of incrementally different sensor elements in a single manufacturing step using ink-jet technology. Controlled compositional gradients in the chemiresistor elements of a sensor array can be induced in a method analogous to how a color ink-jet printer deposits and mixes multiple colors. However, in this case rather than multiple colors, a plurality of different organic materials and conducting components suspended or dissolved in solution which can be deposited are used. A sensor array of a million distinct elements only requires a 1 cm×1 cm sized chip employing lithography at the 10 micrometer feature level, which is within the capacity of conventional commercial processing and deposition methods. This technology permits the production of sensitive, small-sized, stand-alone chemical sensors.

In one embodiment, the sensor arrays have a predetermined inter-sensor variation in the structure or composition of the conductive or semiconductive or insulating organic materials as well as in the conductive components and any insulating or plasticizing components of the composites. The variation may be quantitative and/or qualitative. For example, the concentration of the conductive or semiconductive or insulating organic material in the composite can be varied across sensors. Alternatively, a variety of different organic materials may be used in different sensors. The anions that accompany conducting or semiconducting organic polymers such as polyaniline in some doping states can be compositionally varied to add diversity to the array, as can the polymer composition itself, either structurally (through use of a different family of materials) or through modification of the backbone and/or side chains of the basic polymer structure. This ability to fabricate many chemically different materials allows ready incorporation of a wide range of chemical diversity into the sensor elements, and also allows facile control over the electrical properties of the sensor elements through control over the composition of an individual sensor element in the array. Insulating organic materials can also be used and blended into the array in order to further increase the diversity in one embodiment of the invention. When insulators are added, commercial, off-the-shelf, organic polymers can provide the basic sensor components that respond differently to different analytes, based on the differences in polarity, molecular size, and other properties of the analyte in order to achieve the chemical diversity amongst array elements in the electronic nose sensors. Such insulators would include main-chain carbon polymers, main chain acyclic heteroatom polymers, main-chain heterocyclic polymers, and other insulating organic materials. Otherwise, these properties can be obtained by modification in the composition of the electrically conductive or electrically semiconductive organic component of the sensor composition by use of capping agents on a colloidal metal part of the conductive phase, by use of different plasticizers added to otherwise compositionally identical sensor elements to manipulate their analyte sorption and response properties, by variation in the temperature or measurement frequency of the sensors in an array of sensors that are otherwise compositionally identical, or a combination thereof and with sensors that are compositionally different as well. The sensors in an array can readily be made by combinatorial methods in which a limited number of feedstocks is combined to produce a large number of chemically distinct sensor elements.

One method of enhancing the diversity of polymer based conductor/conductor or conductor/semiconductor or conductor/insulator chemiresistors is through the use of polymer blends or copolymers (Doleman, et al. (1998) Anal. Chem. 70, 2560–2654). Immiscible polymer blends may also be of interest because carbon black or other conductors can be observed to preferentially segregate into one of the blend components. Such a distribution of carbon black conduction pathways may result in valuable effects upon analyte sorption, such as the observance of a double percolation threshold. Binary polymer blend sensors can be prepared from a variety of polymers at incrementally different blend stoichiometries. Instead of manually fabricating twenty blends of varying composition, a spray gun with dual controlled-flow feedstocks could be used to deposit a graded-composition polymer film across a series of electrodes. Such automated procedures allow extension of the sensor compositions beyond simple binary blends, thereby providing the opportunity to fabricate chemiresistors with sorption properties incrementally varied over a wide range. In the fabrication of many-component blends, a combinatorial approach aided by microjet fabrication technology is one approach that will be known to those skilled in the art. For instance, a continuous jet fed by five separate feedstocks can fabricate numerous polymer blends in a combinatorial fashion on substrates with appropriately patterned sets of electrodes. Multiple nozzle drop-on-demand systems (multiple nozzle continuous jet systems are not as prevalent because of their greater complexity) may also be used. In this approach, each nozzle would be fed with a different polymer, each dissolved in a common solvent. In this manner, a large number of combinations of 10–20 polymers can be readily fabricated.

The resistors can include nanoparticles comprising a central core conducting element and an attached ligand, with these nanoparticles dispersed in a semiconducting or conducting organic matrix. As described above, in certain embodiments, the nanoparticles have a metal core. In one method of synthesizing such a core, a modification of the protocol developed by Brust et al. (the teachings of which are incorporated herein by reference), can be used. Using alkanethiolate gold clusters as an illustrative example, and not in any way to be construed as limiting, the starting molar ratio of $HAuCl_4$ to alkanethiol is selected to construct particles of the desired diameter. The organic phase reduction of $HAuCl_4$ by an alkanethiol and sodium borohydride leads to stable, modestly polydisperse, alkanethiolate-protected gold clusters having a core dimension of about 1 nm to about 100 nm. The nanoparticles range in size from about 1 nm to about 50 nm, but may also range in size from about 5 nm to about 20 nm.

In this reaction, a molar ratio of $HAuCl_4$ to alkanethiol of greater than 1:1 leads to smaller particle sizes, whereas a molar ratio of $HAuCl_4$ to alkanethiol less than 1:1 yield clusters which are larger in size. Thus, by varying the ratio of $HAuCl_4$ to alkanethiol, it is possible to generate various sizes and dimensions of nanoparticles suitable for a variety of analytes. Although not intending to be bound by any particular theory, it is believed that during the chemical reaction, as neutral gold particles begin to nucleate and grow, the size of the central core is retarded by the ligand monolayer in a controlled fashion. Using this reaction, it is then possible to generate nanoparticles of exacting sizes and dimensions.

In certain other embodiments, sensors are prepared as composites of "naked" nanoparticles and a semiconducting or conducting organic material is added. As used herein, the term "naked nanoparticles" means that the core has no covalently attached ligands or caps. A wide variety of semiconducting or conducting organic materials can be used in this embodiment. Preferred semiconducting or conducting materials are organic polymers. Suitable organic polymers include, but are not limited to, polyaniline, polypyrrole, polyacetylene, polythiophene, polyEDOT and derivatives thereof. Varying the semiconducting or conducting material types, concentration, size, etc., provides the diversity necessary for an array of sensors. In one embodiment, the conductor to semiconducting or conducting organic material ratio is about 50% to about 90% (wt/wt).

The general method for using the disclosed sensors, arrays and electronic noses, for detecting the presence of an analyte in a fluid, where the fluid is a liquid or a gas, involves sensing the presence of an analyte in a fluid with a chemical sensor. In a preferred implementation, a preferred detector array produces a unique signature for every different analyte to which it is expected to be exposed. Such systems can be constructed to include detectors that probe important, but possibly subtle, molecular parameters such as chirality. The term "chiral" is used herein to refer to an optically active or enantiomerically pure compound, or to a compound containing one or more asymmetric centers in a well-defined optically active configuration. A chiral compound is not superimposable upon its mirror image. Harnessing enantiomer resolution gives rise to myriad applications. For instance, because the active sites of enzymes are chiral, only the correct enantiomer is recognized as a substrate. Thus, pharmaceuticals having near enantiomeric purity are often many more times active than their racemic mixtures. However, many pharmaceutical formulations marketed today are racemic mixtures of the desired compound and its "mirror image." One optical form (or enantiomer) of a racemic mixture may be medicinally useful, while the other optical form may be inert or even harmful, as has been reported to be the case for thalidomide. Various methods exist which generate the correct enantiomer, including chiral synthesis, enzymatic resolution or some other means of obtaining the optically active compound. Due to the wide range of industrial applications, there is a growing interest in finding ways to resolve racemic mixtures into optically active isomers, or to synthesize enantiomerically pure compounds directly and rapidly monitor the efficiency of such processes. Chiral sensor elements could be part of a larger detector array that included non-chiral elements, thus broadening the discrimination ability of such arrays towards chiral analytes. Some of the elements can possess chiral feedstocks and/or chiral organic electrically conducting elements and/or chiral capping agents on conductive particles in order to detect chiral analytes through their distinct response pattern on an array of sensors. Suitable chiral resolving agents include, but are not limited to, chiral molecules, such as chiral polymers; natural products, such as, tartaric, malic and mandelic acids; alkaloids, such as brucine, strychnine, morphine and quinine; lanthanide shift reagents; chelating agents; biomolecules, such as proteins, cellulose and enzymes; and chiral crown ethers together with cyclodextrins. (see, E. Gassmann et al., "Electrokinetic Separation of Chiral Compounds," Science, vol. 230, pp. 813–814 (1985); and R. Kuhn et al., "Chiral Separation by Capillary Electrophoresis," Chromatographia, vol. 34, pp. 505–512 (1992)). Additional chiral resolving agents suitable for use in the present invention will be known by those of skill in the art. In this fashion, the sensors and sensor arrays can assist in assessing which form of chirality, and of what enantiomeric excess, is present in an analyte in a fluid. Due to the presence of chiral moieties, many biomolecules, such as amino acids, are amenable to detection using the sensor arrays of the invention.

Plasticizers can also be used to obtain improved mechanical, structural, and sorption properties of the sensing films. Suitable plasticizers for use in the present invention include, but are not limited to, phthalates and their esters, adipate and sebacate esters, polyols such as polyethylene glycol and their derivatives, tricresyl phosphate, castor oil, camphor etc. Those of skill in the art will be aware of other plasticizers suitable for use in the present invention.

The plasticizer can also be added to an organic polymer forming an interpenetrating network (IPN) comprising a first organic polymer and a second organic polymer formed from an organic monomer polymerized in the presence of the first organic polymer. This technique works particularly well when dealing with polymers that are immiscible in one another, where the polymers are made from monomers that are volatile. Under these conditions, the preformed polymer is used to dictate the properties (e.g., viscosity) of the polymer-monomer region. Thus, the polymer holds the monomer in solution. Examples of such a system are (1) polyvinyl acetate with monomer methylmethacrylate to form an IPN of pVA and pMMA, (2) pVA with monomer styrene to form an IPN of pVA and polystyrene, and (3) pVA with acrylonitrile to form an IPN of pVA and polyacrylonitrile. Each of the example compositions would be modified by the addition of an appropriate plasticizer. More than one monomer can be used where it is desired to create an IPN having one or more copolymers.

In another embodiment, the sensor for detecting the presence of a chemical analyte in a fluid comprises a chemically sensitive resistor electrically connected to an electrical measuring apparatus where the resistor is in thermal communication with a temperature control apparatus. As described above, the chemically sensitive resistor(s) may comprise regions of a conductive organic polymer and regions of a conductive material which is compositionally different than the conductive organic material. The chemically sensitive resistor provides an electrical path through which electrical current may flow and a resistance (R) at a temperature (T) when contacted with a fluid comprising a chemical analyte.

In operation, chemically sensitive resistor(s) of the sensor for detecting the presence of a chemical analyte in a fluid provide an electrical resistance ($R_m$) when contacted with a fluid comprising a chemical analyte at a particular temperature ($T_m$). The electrical resistance observed may vary as the temperature varies, thereby allowing one to define a unique profile of electrical resistances at various different temperatures for any chemical analyte of interest. For example, a chemically sensitive resistor, when contacted with a fluid comprising a chemical analyte of interest, may provide an electrical resistance $R_m$ at temperature $T_m$ where m is an integer greater than 1, and may provide a different electrical resistance $R_n$ at a different temperature $T_n$. The difference between $R_m$ and $R_n$ is readily detectable by an electrical measuring apparatus.

As such, the chemically sensitive resistor(s) of the sensor are in thermal communication with a temperature control apparatus, thereby allowing one to vary the temperature at which electrical resistances are measured. If the sensor comprises an array of two or more chemically sensitive resistors each being in thermal communication with a temperature control apparatus, one may vary the temperature across the entire array (i.e., generate a temperature gradient across the array), thereby allowing electrical resistances to be measured simultaneously at various different temperatures and for various different resistor compositions. For example, in an array of chemically sensitive resistors, one may vary the composition of the resistors in the horizontal direction across the array, such that resistor composition in the vertical direction across the array remains constant. One may then create a temperature gradient in the vertical direction across the array, thereby allowing the simultaneous analysis of chemical analytes at different resistor compositions and different temperatures.

Methods for placing chemically sensitive resistors in thermal communication with a temperature control apparatus are readily apparent to those skilled in the art and include, for example, attaching a heating or cooling element to the sensor and passing electrical current through said heating or cooling element. The temperature range across which electrical resistance may be measured will be a function of the resistor composition, for example the melting temperature of the resistor components, the thermal stability of the analyte of interest or any other component of the system, and the like. For the most part, the temperature range across which electrical resistance will be measured will be about 10° C. to 80° C., preferably from about 22° C. to about 70° C. and more preferably from about 20° C. to 65° C.

In yet another embodiment, rather than subjecting the sensor to a direct electrical current and measuring the true electrical resistance through the chemically sensitive resistor(s), the sensor can be subjected to an alternating electrical current at different frequencies to measure impedance. Impedance is the apparent resistance in an alternating electrical current as compared to the true electrical resistance in a direct current. As such, the present invention is also directed to a sensor for detecting the presence of a chemical analyte in a fluid, said sensor comprising a chemically sensitive resistor electrically connected to an electrical measuring apparatus, wherein said resistor provides (a) an electrical path through said region of nonconductive organic polymer and said conductive material, and (b) an electrical impedance $Z_m$ at frequency m when contacted with a fluid comprising said chemical analyte, where m is an integer greater than 1 and m does not equal 0. For measuring impedance as a function of frequency, the frequencies employed will generally range from about 1 Hz to 5 GHz, usually from about 1 MHZ to 1 GHz, more usually from about 1 MHZ to 10 MHZ and preferably from about 1 MHZ to 5 MHZ. Chemical analytes of interest will exhibit unique impedance characteristics at varying alternating current frequencies, thereby allowing one to detect the presence of any chemical analyte of interest in a fluid by measuring $Z_m$ at alternating frequency m.

For performing impedance measurements, one may employ virtually any impedance analyzer known in the art. For example, a Schlumberger Model 1260 Impedance/Gain-Phase Analyzer (Schlumberger Technologies, Farmborough, Hampshire, England) with approximately 6 inch RG174 coaxial cables is employed. In such an apparatus, the resistor/sensor is held in an Al chassis box to shield it from external electronic noise.

In still another embodiment of the present invention, one may vary both the frequency m of the electrical current employed and the temperature $T_n$ and measure the electrical impedance $Z_{m,n}$, thereby allowing for the detection of the presence of a chemical analyte of interest. As such, the present invention is also directed to a sensor for detecting the presence of a chemical analyte in a fluid, said sensor comprising a chemically sensitive resistor electrically connected to an electrical measuring apparatus and being in thermal communication with a temperature control apparatus, wherein said resistor provides an electrical impedance $Z_{m,q}$ at frequency m and temperature $T_n$ when contacted with a fluid comprising said chemical analyte, where m and/or n is an integer greater than 1. For measuring impedance as a function of frequency and temperature, the frequencies employed will generally not be higher than 10 MHZ, preferably not higher than 5 MHZ. Chemical analytes of interest will exhibit unique impedance characteristics at varying alternating current frequencies and varying temperatures, thereby allowing one to detect the presence of any chemical analyte of interest in a fluid by measuring $Z_{m,n}$ at frequency m and temperature $T_n$.

In another procedure, one particular sensor composition can be used in an array and the response properties can be varied by maintaining each sensor at a different temperature from at least one of the other sensors, or by performing the electrical impedance measurement at a different frequency for each sensor, or a combination thereof.

Electronic noses (such as system 100, above) for detecting an analyte in a fluid can be fabricated by electrically coupling the sensor leads of an array of differently responding sensors to an electrical measuring device (e.g., detector 180). The device measures changes in signal at each sensor of the array, preferably simultaneously and preferably over time. Preferably, the signal is an electrical resistance, although it could also be an impedance or other physical property of the material in response to the presence of the analyte in the fluid. Frequently, the device includes signal processing means and is used in conjunction with a computer and data structure for comparing a given response profile to a structure-response profile database for qualitative and quantitative analysis. Typically, the array includes usually at least ten, often at least 100, and perhaps at least 1000 different sensors though with mass deposition fabrication techniques described herein or otherwise known in the art, arrays of on the order of at least one million sensors are readily produced.

In one mode of operation with an array of sensors, each resistor provides a first electrical resistance between its conductive leads when the resistor is contacted with a first fluid comprising a first chemical analyte, and a second electrical resistance between its conductive leads when the resistor is contacted with a second fluid comprising a second, different, chemical analyte. The fluids may be liquid or gaseous in nature. The first and second fluids may reflect samples from two different environments, a change in the concentration of an analyte in a fluid sampled at two time points, a sample and a negative control, etc. The sensor array necessarily comprises sensors which respond differently to a change in an analyte concentration or identity, i.e., the difference between the first and second electrical resistance of one sensor is different from the difference between the first second electrical resistance of another sensor.

In one embodiment, the temporal response of each sensor (resistance as a function of time) is recorded. The temporal response of each sensor may be normalized to a maximum percent increase and percent decrease in signal which produces a response pattern associated with the exposure of the analyte. By iterative profiling of known analytes, a structure-function database correlating analytes and response profiles is generated. Unknown analytes may then be characterized or identified using response pattern comparison and recognition algorithms. Accordingly, analyte detection systems comprising sensor arrays, an electrical measuring device for detecting resistance across each chemiresistor, a computer, a data structure of sensor array response profiles, and a comparison algorithm are provided. In another embodiment, the electrical measuring device is an integrated circuit comprising neural network-based hardware and a digital-analog converter (DAC) multiplexed to each sensor, or a plurality of DACs, each connected to different sensor(s).

The desired signals if monitored as dc electrical resistances for the various sensor elements in an array can be read merely by imposing a constant current source through the resistors and then monitoring the voltage across each resistor through use of a commercial multiplexable 20 bit analog-to-digital converter. Such signals are readily stored in a computer that contains a resident algorithm for data analysis and archiving. Signals can also be preprocessed either in digital or analog form; the latter might adopt a resistive grid configuration, for example, to achieve local gain control. In addition, long time adaptation electronics can be added or the data can be processed digitally after it is collected from the sensors themselves. This processing could be on the same chip as the sensors but also could reside on a physically separate chip or computer.

Data analysis can be performed using standard chemometric methods such as principal component analysis and SIMCA, which are available in commercial software packages that run on a PC or which are easily transferred into a computer running a resident algorithm or onto a signal analysis chip either integrated onto, or working in conjunction with, the sensor measurement electronics. The Fisher linear discriminant is one preferred algorithm for analysis of the data, as described below. In addition, more sophisticated algorithms and supervised or unsupervised neural network based learning/training methods can be applied as well (Duda, R. O.; Hart, P. E. Pattern Classification and Scene Analysis; John Wiley & Sons: New York, 1973, pp 482).

The signals can also be useful in forming a digitally transmittable representation of an analyte in a fluid. Such signals could be transmitted over the Internet in encrypted or in publicly available form and analyzed by a central processing unit at a remote site, and/or archived for compilation of a data set that could be mined to determine, for example, changes with respect to historical mean "normal" values of the breathing air in confined spaces, of human breath profiles, and of a variety of other long term monitoring situations where detection of analytes in fluids is an important value-added component of the data.

Arrays of 20 to 30 different sensors may be sufficient for many analyte classification tasks but larger array sizes can be implemented as well. Temperature and humidity can be controlled but because a preferred mode is to record changes relative to the ambient baseline condition, and because the patterns for a particular type and concentration of odorant are generally independent of such baseline conditions, it is not critical to actively control these variables in some implementations of the technology. Where desired, such control can be achieved either in open-loop or closed-loop configurations.

The sensors and sensor arrays disclosed herein can be used with or without preconcentration of the analyte depending on the power levels and other system constraints demanded by the user. Regardless of the sampling mode, the characteristic patterns (both from amplitude and temporal features, depending on the most robust classification algorithm for the purpose) associated with certain disease states and other volatile analyte signatures can be identified using the sensors disclosed herein. These patterns are then stored in a library, and matched against the signatures emanating from the sample to determine the likelihood of a particular odor falling into the category of concern (disease or non-disease, toxic or nontoxic chemical, good or bad polymer samples, fresh or old fish, fresh or contaminated air, etc.).

Analyte sampling will occur differently in the various application scenarios. For some applications, direct headspace samples can be collected using either single breath and urine samples in the case of sampling a patient's breath for the purpose of disease or health state differentiation and classification. In addition, extended breath samples, passed over a Tenax, Carbopack, Poropak, Carbosieve, or other sorbent preconcentrator material, can be obtained when needed to obtain robust intensity signals. Suitable commercially available adsorbent materials include but are not limited to, Tenax TA, Tenax GR, Carbotrap, Carbopack B and C, Carbotrap C, Carboxen, Carbosieve SIII, Porapak, Spherocarb, and combinations thereof. Preferred adsorbent combinations include, but are not limited to, Tenax GR and Carbopack B; Carbopack B and Carbosieve SIII; and Carbopack C and Carbopack B and Carbosieve SIII or Carboxen 1000. Those skilled in the art will know of other suitable absorbent materials.

The analyte can be concentrated from an initial sample volume of about 10 liters and then desorbed into a concentrated volume of about 10 milliliters or less, before being presented to the sensor array. The absorbent material of the fluid concentrator can be, but is not limited to, a nanoporous material, a microporous material, a chemically reactive material, a nonporous material and combinations thereof. In certain instances, the absorbent material can concentrate the analyte by a factor that exceeds a factor of about $10^5$, or by a factor of about $10^2$ to about $10^4$. In another embodiment, removal of background water vapor is conducted in conjunction, such as concomitantly, with the concentration of the analyte. Once the analyte is concentrated, it can be desorbed using a variety of techniques, such as heating, purging, stripping, pressuring or a combination thereof. In some these embodiments, the sample concentrator can be wrapped with a wire through which current can be applied to heat and thus, desorb the concentrated analyte. The analyte is thereafter transferred to the sensor array.

Breath samples can be collected through a straw or suitable tube in a patient's mouth that is connected to the sample chamber (or preconcentrator chamber), with the analyte outlet available for capture to enable subsequent GC/MS or other selected laboratory analytical studies of the sample. In other applications, headspace samples of odorous specimens can be analyzed and/or carrier gases can be used to transmit the analyte of concern to the sensors to produce the desired response. In still other cases, the analyte will be in a liquid phase and the liquid phase will be directly exposed to the sensors; in other cases the analyte will undergo some separation initially and in yet other cases only the headspace of the analyte will be exposed to the sensors.

In some cases, the array will not yield a distinct signature of each individual analyte in a region, unless one specific type of analyte dominates the chemical composition of a sample. Instead, a pattern that is a composite, with certain characteristic temporal features of the sensor responses that aid in formulating a unique relationship between the detected analyte contents and the resulting array response, will be obtained.

In a preferred embodiment of signal processing, the Fisher linear discriminant searches for the projection vector, w, in the detector space which maximizes the pairwise resolution factor, i.e., rf, for each set of analytes, and reports the value of rf along this optimal linear discriminant vector. The rf value is an inherent property of the data set and does not depend on whether principal component space or original detector space is used to analyze the response data. This resolution factor is basically a multi-dimensional analogue to the separation factors used to quantify the resolving power of a column in gas chromatography, and thus the if value serves as a quantitative indication of how distinct two patterns are from each other, considering both the signals and the distribution of responses upon exposure to the analytes that comprise the solvent pair of concern. For example, assuming a Gaussian distribution relative to the mean value of the data points that are obtained from the responses of the array to any given analyte, the probabilities of correctly identifying an analyte as a or b from a single presentation when a and b are separated with resolution factors of 1.0, 2.0 or 3.0 are approximately 76%, 92% and 98% respectively.

The following examples are offered by way of illustration and not by way of limitation.

EXAMPLES

Polymers, including poly (ethylene-co-vinyl acetate) with 25% acetate (PEVA), and poly(caprolactone) (PCL) were purchased from Scientific Polymer Products. Solvents were purchased from Aldrich Chemical Corp or EM Science and were used as received.

Detector Film Fabrication. Carbon black-polymer composite suspensions used to form the detector films were prepared by dissolving 160 mg of polymer in toluene, followed by addition of 40 mg of carbon black (Cabot Black Pearls 2000) (Lonergan, et al., Chem. Mat. 1996, 8, 2298–2312). The mixtures were sonicated for 10 min and were then sprayed in several lateral passes using an airbrush (Iowata HP-BC) held at a distance of 10 to 14 cm from the substrate.

Vapor Flow Apparatus. An automated flow system was used to deliver pulses of a diluted stream of solvent vapor to the detectors (Doleman, et al., Anal. Chem. 1998, 70, 2560–2564). The carrier gas was oil-free air obtained from the house compressed air source (1.10±0.15 parts per thousand (ppth) of water vapor) controlled with a 28 L min$^{-1}$ or a 625 ml min$^{-1}$ mass flow controller (UNIT). To obtain the desired concentration of analyte in the gas phase, a stream of carrier gas controlled by a 625 ml min$^{-1}$ or a 60 ml min$^{-1}$ mass flow controller was passed though one of five bubblers. Saturation of the gas flow through the bubbler of interest was confirmed with a flame ionization detector (Model 300 HFID, California Analytical Instruments, Inc.). The saturated gas stream was then mixed with background air to produce the desired analyte concentration while maintaining the total air flow at the desired value for the linear flow chamber experiments (Example 3, below) and at a constant value of 2 L min$^{-1}$ for the stacked detector assemblies (Example 4).

For detectors in the linear flow chamber, the air flow was connected directly to the channel adjacent to the row of detectors. To produce the low flow rates required by this experiment, the analyte-containing vapor was generated at higher flow rates, and a constant 200 ml min$^{-1}$ was subtracted with a flow-regulated pump, permitting the difference to flow into the detector chamber. This flow was then divided into the two equally sized openings of the two channels in the chamber. The volumetric flow rates quoted below reflect the volumetric flow rate in each separate gap between the detector substrate and the Teflon-lined Al block.

For detectors arranged in the stacked assembly, a constant output of 2 L min$^{-1}$ from the vapor generator was directed at the front end of the sampling device through use of a Teflon tube that was slightly larger in diameter than the opening of the stack device. Vapor flow through the channels in the stack assembly was maintained at a volumetric flow rate of 75 ml min$^{-1}$, i.e., 12.5 ml min$^{-1}$ per channel. The excess flow of 1.925 L min$^{-1}$ flowed away from the stack device without proceeding through the channels or over the face sensors.

All exposed parts of the flow system were constructed from Teflon, stainless steel, or Al. The temperature during data collection was approximately 294 K, and the temperature was passively controlled by immersing the solvent bubblers into large tanks of water. For the linear row of detectors, vapor presentations were 300 s in duration, and analyte exposures were separated in time by at least 75 min to minimize any possible influence of the previous exposure. The analyte was delivered at a constant activity of P/P°=0.10, where P is the partial pressure and P° is the vapor pressure of the analyte. For experiments with stacked detector arrays, the vapor presentations were 240 s in duration, separated in time by 25 min, and were conducted at a fixed analyte activity of P/P°=0.050. Flow experiments were performed separately on each of the three separate stack assemblies. Each stack assembly received 10 exposures to each of four analytes, and the order of these 40 total presentations was randomized with respect to the analyte identity and with respect to replicate exposures to a given analyte. A different randomized analyte presentation order was used for each of the three stack assemblies. A personal computer running programs developed with LabVIEW 5.0 controlled both the flow system and the data acquisition apparatus.

DC Resistance Measurements. DC resistance data were collected using a Keithley 2002 multimeter and a Keithley 7001 multiplexer. Shielded, twisted pair cables were used, and each resistance value was integrated over 2 or 10 power line cycles to reject 60 Hz pickup. Data were processed using a program written in Microsoft Excel Basic. The relative differential resistance change, $\Delta R_{final}/R_b$, was calculated for each detector, where $R_b$ is the baseline resistance averaged over approximately 20 s prior to vapor presentation, and $\Delta R_{final}$ is the differential resistance change relative to $R_b$. The value of $\Delta R_{final}$ was evaluated over a period of approximately 20 s at a fixed time after initiating the vapor presentation. This time varied between the different types of experiments, either from 40 to 60 s, 200 to 220 s or 240 to 260 s after the start of the vapor presentation. For ease of visualization on a common graph of the different absolute responses of the various detector/analyte combinations, the $\Delta R/R_b$ data in some figures have been normalized. In these figures, data were normalized by the mean response value, $(\Delta R/R_b)_j$, of the detector in the physical position j for each set of identical exposures (i.e., for exposures to a common analyte, or for exposures to a common analyte at a common flow rate, as specified). The value for j was chosen as the position of the detector to first physically encounter the analyte.

The rms noise, $N_{rms}$, of a detector was measured as the standard deviation of the data points obtained from the multimeter in the period immediately prior to each vapor presentation, divided by the average resistance value of the multimeter data points produced over that same measurement period. The period used to measure this baseline noise was equal to the time elapsed between determination of the baseline resistance and the determination of the differential resistance change upon analyte exposure. This ensured that the signals were measured in the same bandwidth as the noise. The multimeter was used to determine both the signal and noise values for this calculation because it was desirable to measure the signal and noise of the detectors using the same instrumental apparatus (i.e., the N in S/N is $N_{rms}$). The values of the S/N were calculated independently for each separate presentation of analyte to each detector. For the multimeter measurement of the noise of the films of different sizes described above, the same analysis was used, except the noise was calculated over an interval of only 20 s, and 5 of these values, separated in time by 100 s, were averaged to generate $N_{rms}$. Unlike the values for $S_n$, which is a measure of the noise power, these noise values, $N_{rms}$, were first squared to yield $N^2_{rms}$ prior to plotting them against film volume.

Example 1

Spectral Noise Measurements

For measurements of the noise properties of the detector films, glass microscope slides were coated with a 50 nm thick layer of Au on top of a 15–30 nm thick layer of Cr, in a pattern that produced rectangular gaps between two parallel metal contact regions. The ratio of the rectangular edge length to the gap length was 8:1, and this aspect ratio was held constant as the area of the gap was varied. After film deposition, this procedure resulted in detector films of similar resistance values that had systematically varying film volumes. Carbon black composite films containing either PEVA or PCL, and having areas of 0.080, 0.30, 1.2, 1.3, 5.0, 33.0, and 132 mm², with resistance values ranging from 70 to 160 kΩ, were then deposited onto these substrates. The resulting detector film thicknesses, which were between 180 and 300 nm for the PEVA films and between 60 and 120 nm for the PCL films, were measured with a Sloan Dektak model 3030 profilometer.

Noise of the detector films was determined according to a standard method (Dziedzic, et al., J. Phys. D-Appl. Phys. 1998, 31, 2091–2097; Deen, et al, J. Vac. Sci. Technol. B 1998, 16, 1881–1884). Briefly, the films were placed into a metal box and were biased with a stack of batteries (18 volts total) that was connected in series to a 1 MΩ resistance. The 1 MΩ low-noise resistance was formed from ten 100 kΩ wire-wound resistors (Newark Electronics) that were soldered together in series. The bias voltage across the detector film was ac coupled to an SR560 wide-band low noise voltage preamplifier (Stanford Research Systems), and the output of the preamplifier was sent to an SR785 dynamic signal analyzer (Stanford Research Systems). Using an average of 100 measurements, a power spectral density from 1 Hz to 800 Hz was collected for each film. Data collection occurred over a period of in excess of 100 s for each noise spectral power measurement. These spectra were divided by the square of the bias voltage applied to the chemiresistor, $V_b^2$, to yield the relative power spectral density $S_n$ for each detector film.

A control experiment was performed to evaluate whether film-substrate contacts dominated the observed noise properties of the detectors. Two composite films of approximately the same thickness, film area, and resistance were fabricated, with one film deposited in five 0.38 mm gaps between ten parallel 5.0 mm wide Cr/Au electrical contact pads, and the other film deposited across only one 2.0 mm gap between two parallel 5.0 mm wide Cr/Au contact pads. The additional film/substrate contacts produced no change in the relative noise power of the films, suggesting that the measured noise resulted primarily from the properties of the bulk detector film as opposed to the properties of the film electrode contacts. The properties of commercial, low noise, wire-wound resistors that had resistances similar to those of the carbon black composite films were also measured. The much lower noise values observed for these wire-wound resistors, which are known to exhibit little or no 1/f noise, confirmed that the Johnson noise of the resistors plus any additional amplifier noise of the experimental setup was much lower than the 1/f noise observed for the carbon black composite films. No correction for the amplifier noise was therefore performed in analysis of the noise data of the carbon black composite detector films.

Figure 7:
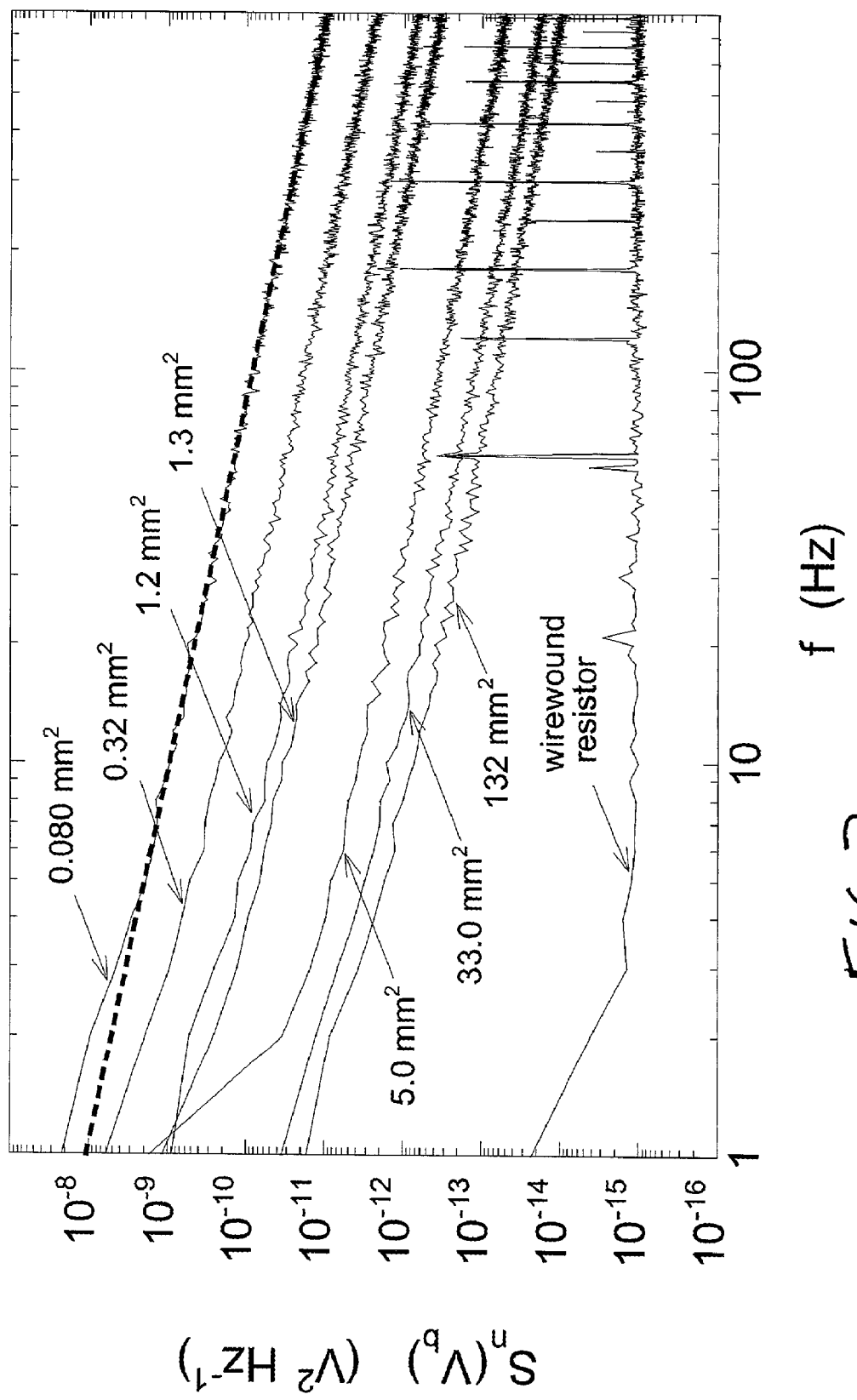
FIG. 7 illustrates a plot of the power spectral density of noise versus frequency for seven polymer-carbon black composite detector films according to the invention.

FIG. 7 displays the noise power spectral density, $S_n(V_b)$, between 1 Hz and 800 Hz for a set of carbon black composite thin film detectors as a function of the area covered by the composite between the electrical contact pads. Power spectral density of the noise, $S_n(V_b)$, versus frequency, f, for seven poly (ethylene-co-vinyl acetate), 25% acetate (PEVA)-carbon black composite detector films of varying area. The dimensions of the rectangularly shaped regions bridged by polymeric composite between the electrical contact pads were (in mm): 0.10×0.80, 0.20×1.60, 0.38×3.05, 0.40×3.20, 0.79×6.3, 2.03×16.3, 4.06×32.5. The PEVA-carbon black composite films were ≈230 nm in thickness as determined by profilometry. The dashed line indicates a fit of one such plot to a function of the form $S_n(V_b)=1\times10^{-8}/f^{1.054}$. Also shown are data for a wire-wound, low noise, 70 kΩ resistor. The electrode contact dimensions in these experiments were scaled such that the resistance (≈100 kΩ) was approximately constant as the film area was varied. Any variation in the noise thus arose from the film area and not from a variation in response of the preamplifier to different absolute input resistance values. An additional advantage of maintaining a constant aspect ratio for the different volume films is to reduce the variation in the noise that has been observed in some thick-film resistors of different aspect ratios.

The power spectral density of the carbon black-polymer thin film composites was well-fit to a function of the form $S_n(V_b) \propto 1/f^\gamma$ with an exponent of $\gamma=1.1$. Some deviation from the 1/f behavior was observed at very low frequencies (<5 Hz), but this deviation may have resulted from the mechanical contacts used to make connections to the Au/Cr/glass substrates. The noise power spectral density of the wire-wound resistor was much lower than the 1/f noise of any of the detector films at the frequencies investigated in this study.

Figure 8A:
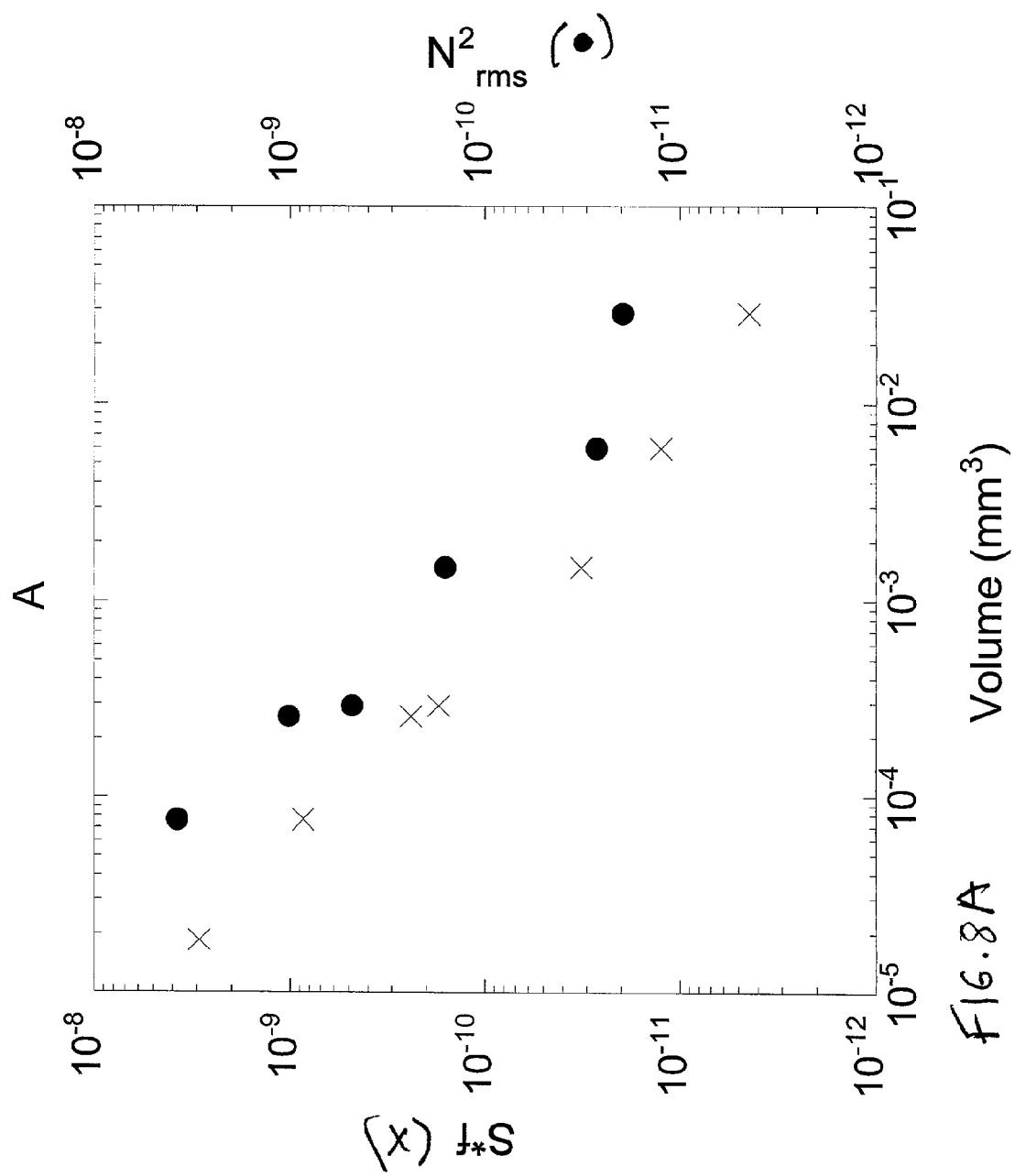
FIGS. 8A and 8B illustrate plots of spectral density of noise times frequency and the square of noise values as a function of volume for two polymer-carbon black composite detector films.
Figure 8B:
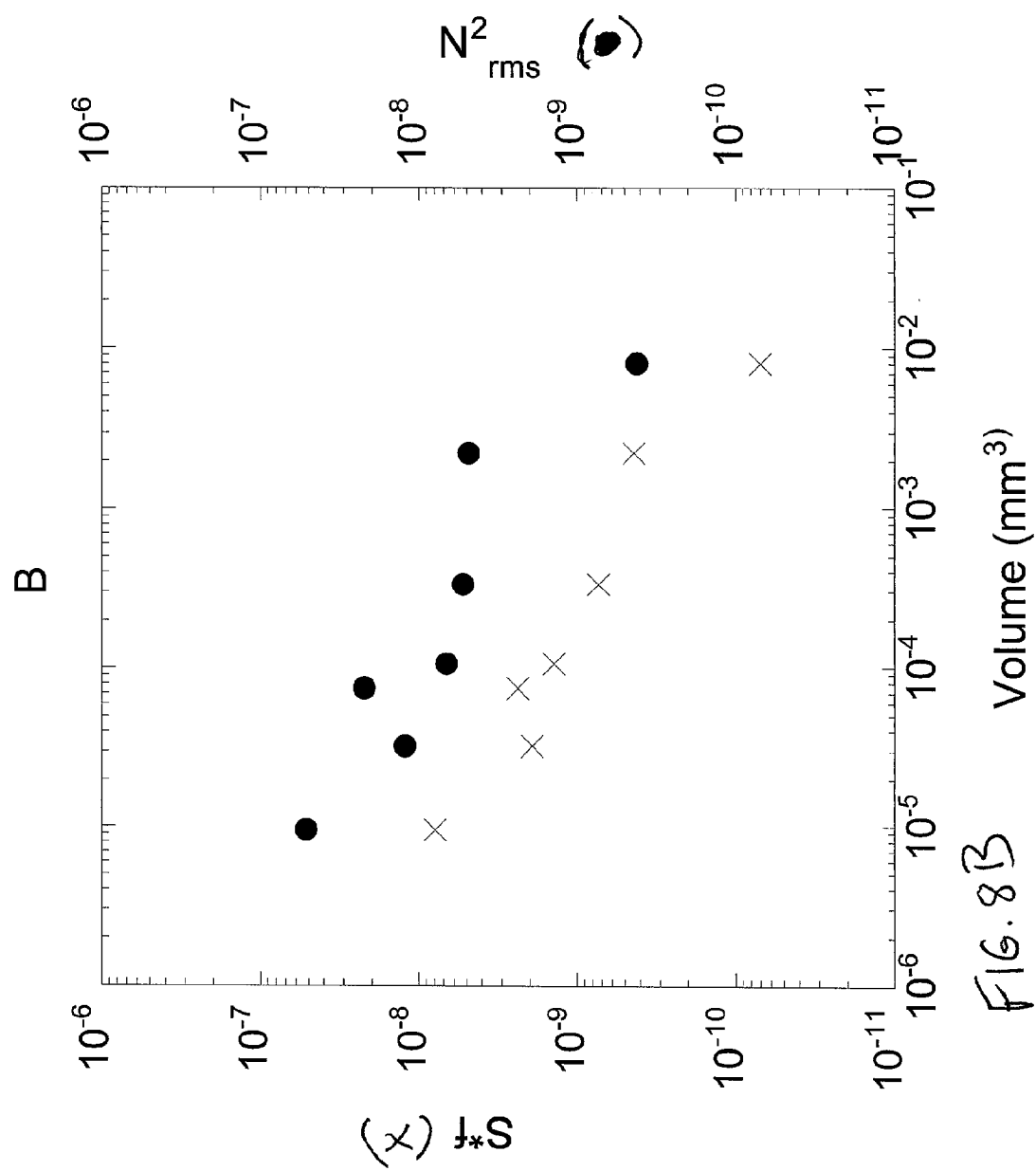

FIGS. 8A and 8B illustrates the value of the $S_n*f$ product (crosses) for carbon black composite detectors fabricated from PEVA and PCL, respectively, as a function of the volume of the detector film. The PEVA-carbon black composite films were ≈230 nm in thickness and the PCL-carbon black composites were ≈80 nm in thickness as determined by profilometry. For these comparisons, the data were taken as the value of $S_n$ at 10 Hz to avoid the lower frequency contact noise. These values are directly comparable because they were taken at the same frequency, but the $S_n*f$ product was displayed because it is essentially independent of frequency for the 1/f region above about 5 Hz in frequency. Also shown are the square of the noise values, $N^2_{rms}$, (filled circles) derived from analysis of the standard deviation of the baseline resistance values verses time as determined on these same films using the multimeter. The detector films used in these experiments were all approximately the same thickness, but the film volume data were calculated using the actual thickness values determined from profilometry measurements of the thickness of each detector film.

The $N^2_{rms}$ and $S_n*f$ values decreased approximately linearly with the film volume, V, with a plot of $S_n*f$ versus V for PEVA-containing carbon black composites having a slope of −0.95 ($R^2=0.989$) and a plot of $N^2_{rms}$ versus V having a slope of −0.91 ($R^2=0.964$). For the PCL-containing carbon black composite films, the slope of $S_n*f$ versus V was −0.60 ($R^2=0.933$) whereas the slope of $N^2_{rms}$ versus V was −0.58 ($R^2=0.833$). It is difficult to perform a quantitative comparison between the $S_n*f$ and $N^2_{rms}$ values, due to the impedance mismatch between the input amplifier of the multimeter and the resistive load of the detector, the variable bandwidth of the multimeter during various resistance readings, and other well-known electronic circuit considerations. However, the inverse dependence of the $N^2_{rms}$ value on the volume of the detector film is clearly seen in both sets of measurements. Deviations from a strictly linear dependence of the relative noise power on V with a slope of −1 have been observed previously for polymer film resistors, and have been explained by factors arising from the film-electrode contacts, inhomogeneities in film composition, and/or variability in film thickness over the measured detector area. The deviations that observed here may also have resulted from properties related to the relatively thin nature of the films used.

Example 2

Determination of Polymer/Gas Partition Coefficients

Quartz crystal microbalance (QCM) measurements were performed on pure films of both PEVA and PCL at 294 K using 10 MHz resonant frequency quartz crystals and a measurement apparatus as described in Severin, et al., Anal. Chem. 2000, 72, 2008–2015. Twenty vapor presentations, each 120 s in duration and separated in time by 15 min, were performed at each of 4 concentrations (P/P°=0.010, 0.030, 0.050, 0.10) of n-hexane and of methanol. The order of vapor presentation was randomized with respect to analyte identity, analyte concentration, and repetition of conditions. The frequency shifts of the polymer-coated QCM crystals arising from deposition of the polymer film, $\Delta f_{polymer}$, were recorded as the difference in the resonant frequency of the crystal before and after deposition of the polymer film. The frequency change upon exposure toe analyte vapor, $\Delta f_{analyte}$, was calculated as the difference in the resonant frequency of the film-coated crystal during exposure to the specific analyte vapor relative to the baseline resonant frequency of the film-coated crystal in background air. The baseline frequency was taken as the mean frequency value obtained for the film-coated crystal during a 30 s period immediately prior to exposure to the analyte, and the frequency during exposure to analyte vapor was taken to be the mean frequency value observed between 80 s and 110 s after the vapor exposure had been initiated.

Figure 9A:
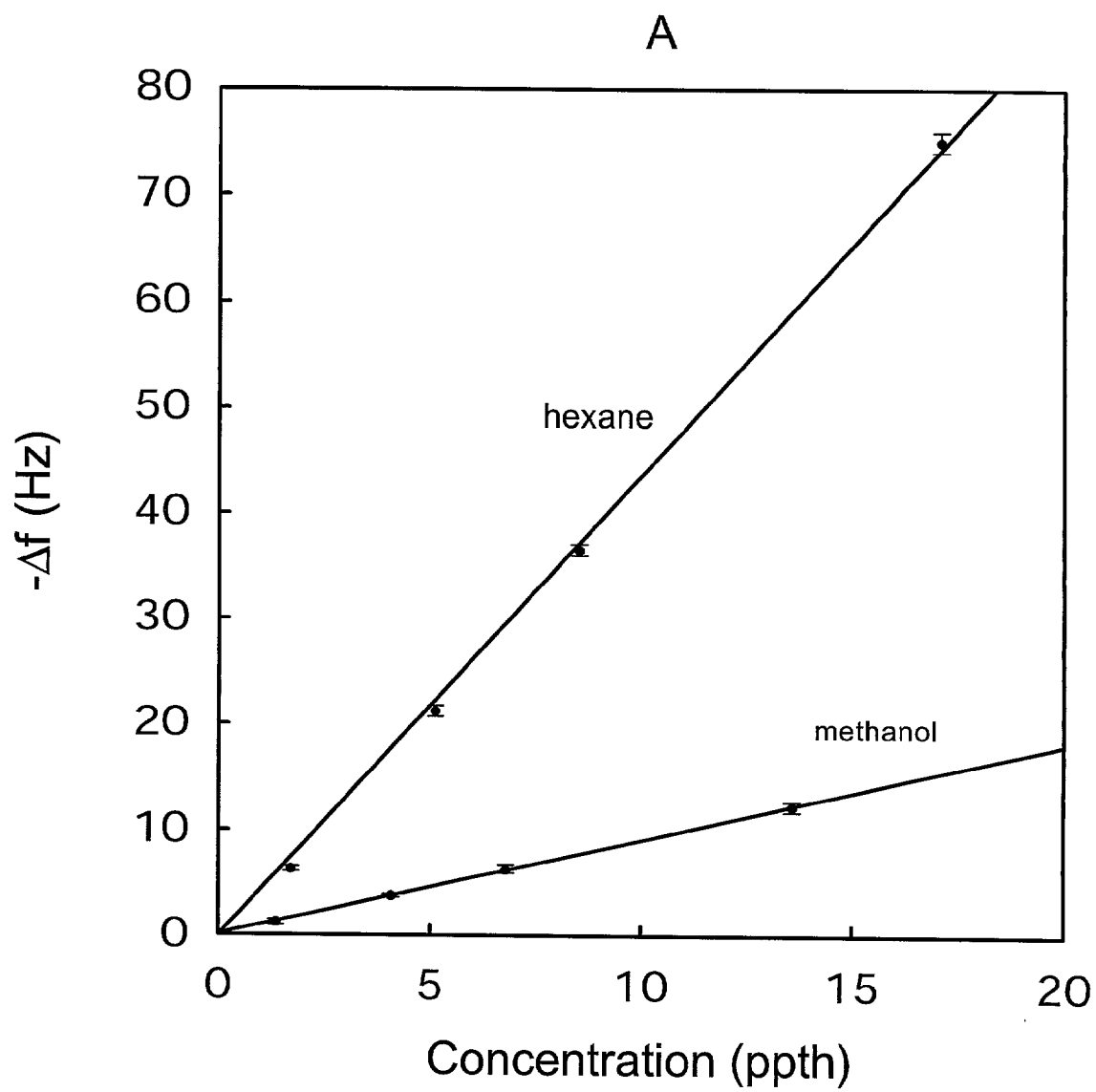
FIGS. 9A and 9B illustrate a plot of differential frequency changes of quartz crystal microbalances coated with two polymer films during exposure to hexane and methanol.
Figure 9B:
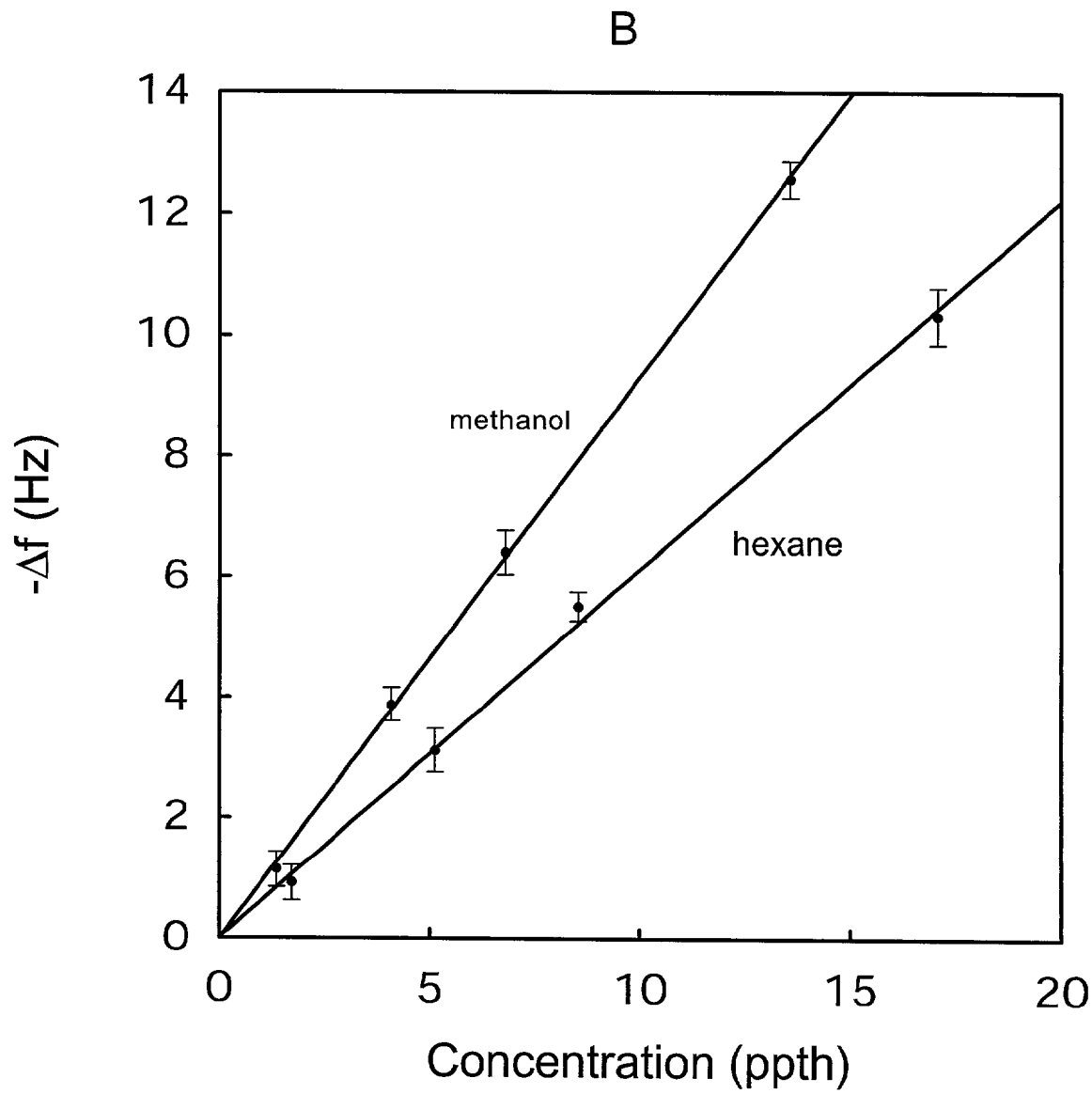

For a given volume of sampled analyte, the detector volume that will produce optimum signal/noise performance for a specific polymer/analyte combination can be calculated from Equation 12 if the polymer/gas partition coefficient is known. Accordingly, data for the partition coefficients of hexane and methanol into PCL and PEVA were determined using QCM measurements. FIGS. 9A and 9B illustrate differential frequency changes, $-\Delta\Delta f_{analyte}$, of quartz crystal microbalances coated with PEVA (FIG. 9A) and PCL (FIG. 9B) polymer films during exposure to hexane at P/P°=0.010, 0.030, 0.050, and 0.10 (1.7, 5.1, 8.5, 17 parts per thousand, ppth) and methanol at P/P$_o$=0.010, 0.030, 0.050, and 0.10 (1.3, 4.1, 6.8, 14 ppth), where P is the partial pressure of analyte and P$_o$ is the vapor pressure of the analyte at 294 K. Each data point represents an average of 20 $\Delta R/R_b$ responses, and the error bars indicate plus and minus one standard deviation around the mean. The frequency shifts corresponded to decreases in frequency upon exposure to analyte. Lines were fitted through these points with a forced zero intercept. The slopes of these lines were a) hexane: 4.36 ($R^2$=0.9988); methanol: 0.910 ($R^2$=0.9995); b) hexane: 0.612 ($R^2$=0.9977); methanol: 0.930 ($R^2$=0.9995). The frequency shifts due to coating the crystal with the polymer were −6835 Hz for PEVA and −4355 Hz for PCL.

The frequency shifts of the polymer-coated QCM crystals arising from deposition of the polymer film, $\Delta f_{polymer}$ and from sorption of the analyte vapor, $\Delta f_{analyte}$, were in total much less than 2% of the resonant frequency of the uncoated crystal. Under such conditions, it has been reported that mechanical losses are minimal and that the frequency shifts are predominantly due to changes in mass uptake (Lu, C., in Applications of Piezoelectric Quartz Crystal Microbalances; Lu, C. C., Ed., Elsevier, N.Y., 1984, Vol., 7, pp. 19–61), which can be calculated from the Sauerbrey equation (Lu, C., in Applications of Piezoelectric Quartz Crystal Microbalances; Lu, C. C., Ed., Elsevier, N.Y., 1984, Vol., 7, pp. 19–61; Buttry, D. A., in Electroanalytical Chemistry; A Series of Advances; Bard, A. J., Ed., Marcel Dekker, N.Y., 1991, Vol. 17, pp 1–85). Polymer/gas partition coefficients were therefore calculated by fitting a line with a forced zero intercept through the $\Delta f_{analyte}$ versus concentration data for each polymer/analyte combination. The slopes of these lines were −4.36 ($R^2$=0.9988) and −0.910 ($R^2$=0.9995) for hexane and methanol, respectively, sorbing into PEVA, and were −0.612 ($R^2$=0.9977) and −0.930 ($R^2$=0.9995) for hexane and methanol, respectively, sorbing into PCL. The slopes of the resulting lines were converted into partition coefficients using:

$$K=(10^6 \rho R T m)/(M_w \Delta f_{polymer} P_{atm}) \tag{13}$$

where R the ideal gas constant (L atm mol$^{-1}$ K$^{-1}$), $\rho$ is the density (g ml$^{-1}$) of the polymer, T is the temperature (K), m is the slope of $\Delta f_{analyte}$ versus concentration (Hz/parts per thousand in air), M$_w$ is the molecular weight (g mol$^{-1}$) of the analyte, $\Delta f_{polymer}$ (Hz) is the frequency shift corresponding to deposition of the polymer, and P$_{atm}$ is the atmospheric pressure (atm). The partition coefficients for each analyte/polymer combination are shown in FIG. 10.

Partition coefficients for the lower vapor pressure analytes, dodecane and hexadecane, were difficult to measure because these very low vapor pressure analytes adsorbed to the walls of the chamber and required long times as well as high analyte volumes to reach true equilibrium conditions. Instead, the values for these analytes were estimated by multiplying the measured polymer/gas partition coefficients for hexane by the ratio of the vapor pressures of dodecane and hexadecane relative to that of hexane (see Doleman, et al., Proc. Natl. Acad. Sci. U.S.A. 1998, 95, 5442–5447). This is a good approximation provided that the activity coefficients do not vary significantly for sorption of these three alkanes into the polymers of interest. As shown in FIG. 10, the polymer/gas partition coefficients varied from measured values of $10^2$ for hexane and methanol to values of over $10^7$ estimated for the lowest vapor pressure analyte, hexadecane.

The wide difference in vapor pressures between the analytes of concern is expected to have a significant influence on the physical array design for optimization of the signal/noise ratio as given by Equation 9. In a chamber of headspace thickness of $1.0 \times 10^{-2}$ cm, with a detector film thickness of $1.0 \times 10^{-4}$ cm, the optimum detector area for a 1.0 cm$^3$ volume of an analyte sample for which the analyte polymer/gas partition coefficient is $1.0 \times 10^2$ is 1.0 cm$^2$. In contrast, for the same sampled volume, headspace thickness, and detector film thickness, a detector area of only $1.0 \times 10^{-5}$ cm$^2$ produces maximum S/N performance for an analyte having a polymer/gas partition coefficient of $1.0 \times 10^7$. The implications of this wide variation in polymer/gas partition coefficient for optimizing the signal/noise performance of sorption-based vapor detectors are explored in detail below.

Example 3

Vapor Response of Linear Arrays of Chemically Equivalent, Spatially Nonequivalent Detectors To investigate the spatiotemporal and geometric aspects of the chemiresistive vapor detectors, a linear array of detectors having a defined headspace and analyte flow configuration was constructed similar to the design illustrated in FIGS. 1A, 1B and 1C. A series of parallel Cr/Au contacts was formed on each side of 75 mm×25 mm glass slides. These contact electrodes were 1.8 mm long and were separated by a gap of 0.4 mm. Each pair of electrodes, which defined the contacts for an individual detector, was spaced 5 mm apart, permitting formation of 15 individual detectors on each side of the glass slide. The area surrounding the electrodes was coated with a thin layer of Teflon.

Both sides of the substrate were masked, with the exception of a 5 mm by 75 mm rectangular region on each side of the substrate that was centered on the row of electrical contacts used to form the detectors. Through this mask, carbon black-PEVA composites were sprayed onto one side of the glass microscope slide and carbon black-PCL composites were sprayed onto the other side of the glass slide. After spraying, the carbon black-polymer films covered the entire length of these substrates (Scheme II). Two such substrates were prepared. On the first substrate, the resulting detectors had resistance values that ranged from 60 to 160 k$\Omega$ on the side sprayed with a PCL-carbon black composite and from 140 to 180 k$\Omega$ on the side sprayed with a PEVA-carbon black composite. The ranges on the second substrate were 70 to 110 k$\Omega$ on the side sprayed with the PCL-carbon black composite and 170 to 260 k$\Omega$ on the side sprayed with a PEVA-carbon black composite.

A low volume vapor sample chamber was custom fabricated for the vapor response experiments. The detector substrate was placed between two pieces of Al, each of which had a recess 3.5 mm wide and 400 μm in depth machined along its length. Prior to assembly, a thin piece of Teflon tape was smoothed over the surface of the Al pieces and into the channel, effectively lining the top and the sides of the channel with an ≈60 μm thick layer of Teflon. This Teflon prevented contact between the analyte and the Al and also formed an airtight gasket between each Al piece and the substrate. Assembly of the Al pieces and the substrate created one shallow channel above the substrate and one shallow channel below the substrate, with each channel being 340 μm deep (400 μm channel depth minus 60 μm thickness of Teflon insulation) and 3.4 mm wide (3.5 mm machined width minus 2×0.06 mm thickness of Teflon insulation). Each channel spanned the entire length of the row of 15 detectors on its corresponding side of the substrate. The 3.4 mm width of the channel bounded the gas flow into a region that was less than the width of the detector film that had been sprayed onto the substrate. Hence, for the entire length of the channel, the detector film completely coated the substrate in the region adjacent to the channel.

The responses of arrays of carbon black-polymer composite vapor detectors were investigated as a function of position relative to the location of analyte flow injected into the detection chamber. The pattern of the contacts beneath the film of carbon black/polymer composite in the linear sensor array produced an array of chemiresistive detectors that were arranged in a linear geometry, parallel to the analyte flow path, and which were spaced at 5 mm intervals downstream from the location of flow injection. The headspace volume was defined by the 3.4 mm width, 340 μm depth, and 75 mm total length of this channel over the detector film. The area of the carbon black-polymer composite film spanned the entire length of the substrate and was sufficiently wide to ensure that the entire region of the substrate in contact with this vapor channel was coated with the detector film. Hence, in many respects this experimental apparatus is analogous to probing the spatiotemporal distribution of analyte in the sorbent phase after injection of a sample onto a gas chromatography column or to ascertaining spectroscopically the position of analyte in a thin layer chromatography experiment as a function of time.

Figure 11:
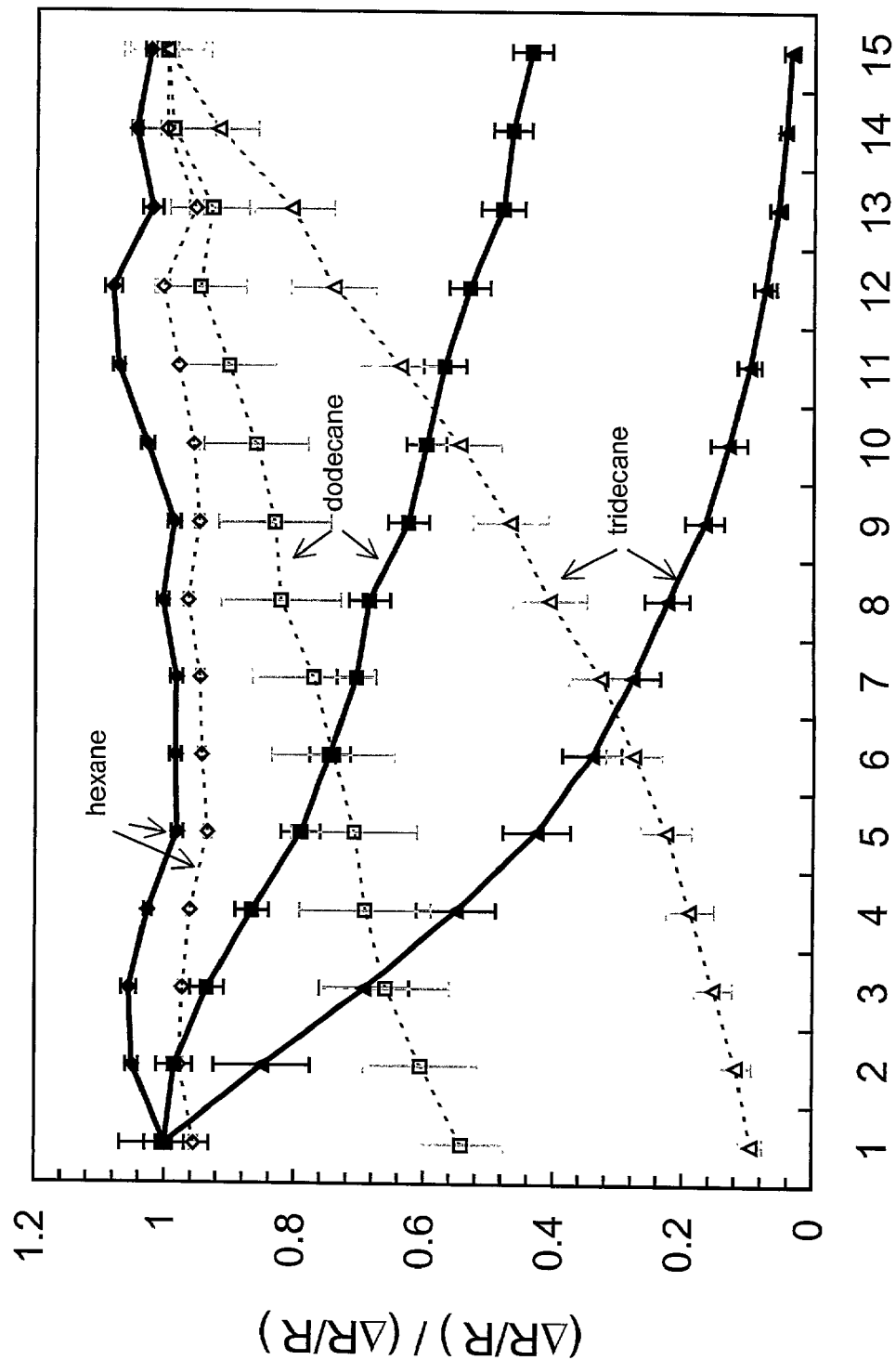
FIG. 11 illustrates a plot of normalized relative differential resistance responses of polymer-carbon black composite detectors exposed to a high vapor pressure analyte (hexane), a moderately low vapor pressure analyte (dodecane) and a low vapor pressure analyte (tridecane) at a constant activity and volumetric flow rate.

FIG. 11 displays data collected for the array exposed in this configuration at a fixed, low carrier gas flow rate of three analytes of differing vapor pressure (hexane, dodecane, and tridecane, vapor pressure of $3.9\times10^{-2}$ torr at 294 K, each at a constant activity of P/P$^o$=0.10 and at a volumetric flow rate of 6 ml min$^{-1}$), to a series of PEVA-carbon black composites. The data are the relative differential resistance values measured in a 20 s period after 240 s of continuous exposure to the various analytes of interest. The analyte exposures used to produce these data were randomized with respect to analyte identity and with respect to the 5 replicate exposures of each analyte at the concentration of interest. For ease of visualization on a common graph of the different absolute responses of the various detector/analyte combinations, the data in this figure have been normalized relative to the mean response of the first detector that physically encountered the analyte. The solid lines indicate responses when the analyte flowed in the direction from the leftmost detector (corresponding to the detector with the lowest numbered position) to rightmost detector. These data (and associated standard deviations) were normalized to the mean response value of the detector in position 1 in the array (j=1) for the 5 exposures to the analyte of interest. The normalization constants (values by which the data were multiplied for display on the plot) are: 10.8, 16.7, and 32.1, for hexane, dodecane, and tridecane, respectively. The dashed lines indicate responses recorded when the same row of detectors was exposed to vapor flowing in the opposite direction through the detector chamber; consequently, these data (and associated standard deviations) were normalized to the mean response value of the detector in position 15 in the array (j=15) to the 5 exposures of the analyte of interest. Normalization constants for these data are: 10.4, 15.3, and 30.2, for hexane, dodecane, and tridecane, respectively.

For high vapor pressure analytes, the detectors all produced nominally identical responses to the analyte after this exposure period. For example, the standard deviation of the mean response to hexane at P/P$^o$=0.10 for the 15 nominally identical detectors was less than 5% of the mean $\Delta R/R_b$ response value for this detector/analyte combination. This degree of reproducibility is consistent with prior reports that have evaluated the reproducibility of the response of carbon black/polymer composite detectors (Lonergan, et al., Chem. Mat. 1996, 8, 2298–2312).

In contrast, for exposures to low vapor pressure analytes such as tridecane, the $\Delta R/R_b$ values observed from the detectors to first encounter the vapor stream were much higher than $\Delta R/R_b$ values observed for detectors located at positions remote from the injection location. The position-related variation in $\Delta R/R_b$ in response to the low vapor pressure analytes was clearly much greater than the standard deviation of the $\Delta R/R_b$ value observed for replicate exposures to any of the analytes investigated. The trend was systematic in that the detectors closest to the analyte injection position displayed the highest $\Delta R/R_b$ values, the response decreased monotonically with position from the location of analyte injection, and the magnitude of the effect increased as the vapor pressure of the analyte decreased. Furthermore, for the low vapor pressure analytes the change in mean response versus detector position far exceeded the standard deviation of the mean responses observed for these same detectors when exposed, in the identical apparatus, to analytes having high vapor pressures.

To conclusively prove that the effect was associated with the geometry of the flow system relative to the position of the detectors in the chamber, and not with any physicochemical inequivalence in the detectors themselves, the position of analyte injection was changed such that the flow proceeded in the opposite direction through the chamber, with analyte first encountering detector number 15 and finally encountering detector number 1 in FIG. 1A. The same analytes were used and the order of presentation was again randomized with respect to solvent identity and with respect to the five replicate exposures to each analyte; however, the exposure order was the same as that used when the flow proceeded from low to high detector number. As shown in FIG. 11, the detectors again provided essentially equivalent responses when exposed to high vapor pressure analytes at a volumetric flow rate of 6 ml min$^{-1}$. For low vapor pressure analytes, the highest $\Delta R/R_b$ values were again observed from the detectors that first physically encountered the vapor stream.

Figure 12A:
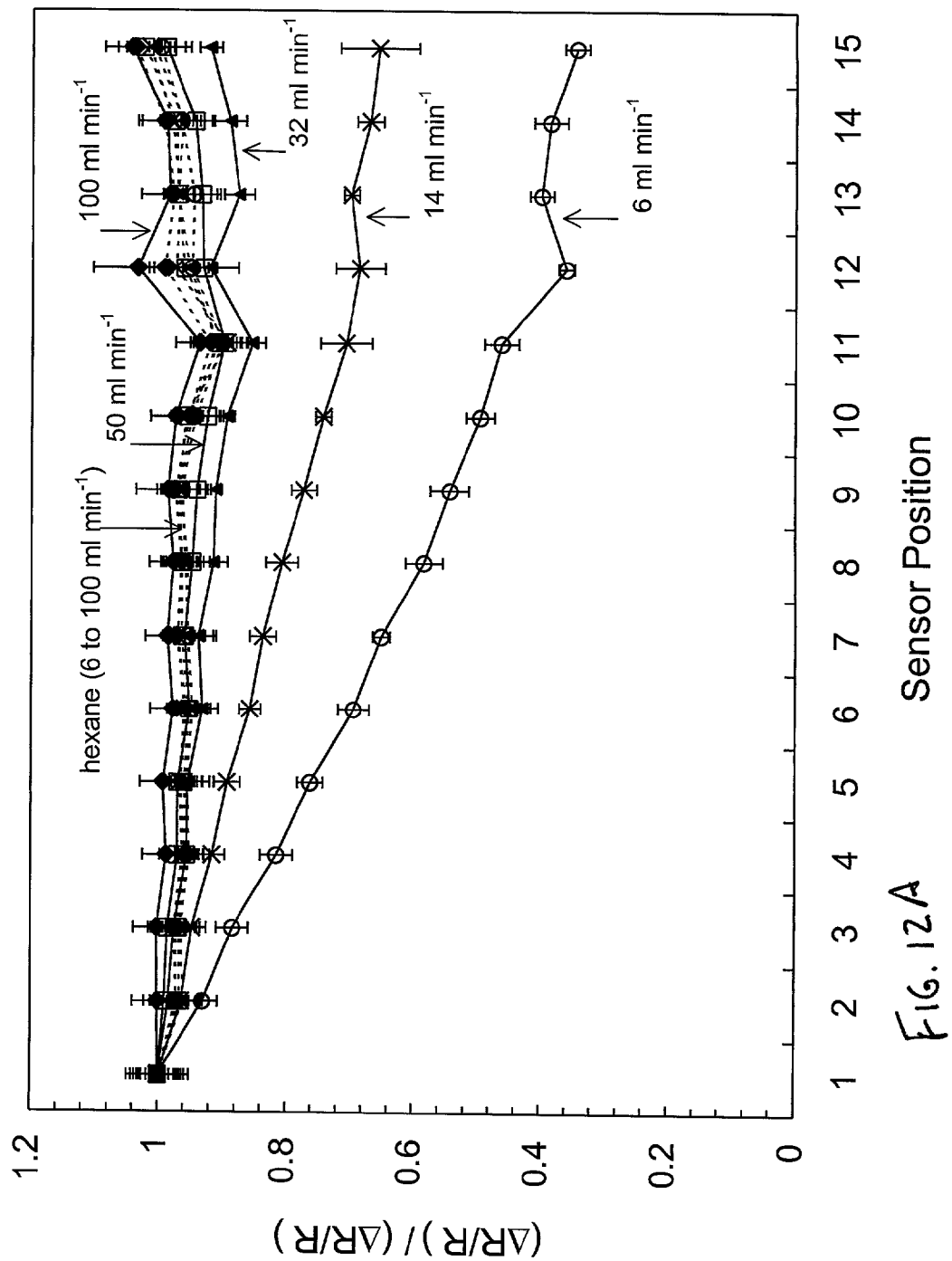
FIGS. 12A and 12B illustrate plots of normalized relative differential resistance responses for two different polymer-carbon black composite detectors to hexane and dodecane at a constant activity in air.
Figure 12B:
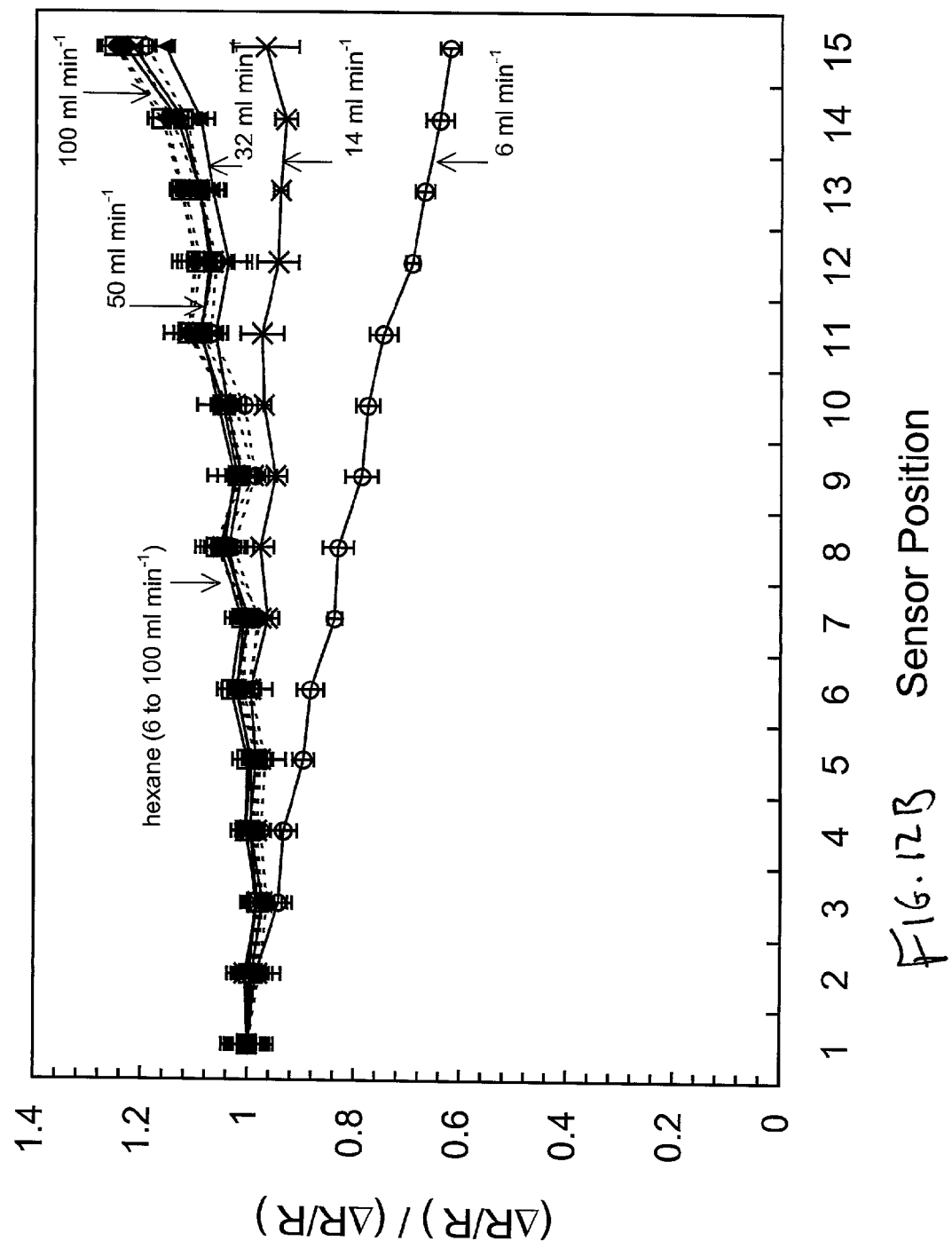

FIGS. 12A and 12B display similar data, collected on a different substrate, as a function of analyte flow velocity. Data presented are for two analytes, one having a high vapor pressure (hexane) and the other having a low vapor pressure (dodecane), both exposed to either PEVA-carbon black (FIG. 12A) or to PCL-carbon black (FIG. 12B) composite detector films. For each flow rate, hexane and dodecane were alternately presented to the detectors. This procedure was repeated for each of 5 flow rates, proceeding sequentially from the lowest volumetric flow rate to the highest volumetric flow rate. This 10 exposure protocol was then repeated in its entirety 4 times, producing 50 total exposures of analyte to the detectors.

For high vapor pressure analytes (i.e., analytes with relatively small polymer/gas partition coefficients), all of the detectors exhibited essentially the same $\Delta R/R_b$ response values in the 20 s period after 240 s of analyte exposure at all tested flow rates, regardless of the position of the detector relative to the point of analyte injection. This is expected because the analyte sorption process determines the steady-state value of $\Delta R/R_b$, and because all of the detectors experienced essentially identical concentrations of analyte under such conditions.

Low vapor pressure analytes (i.e. analytes with large polymer/gas partition coefficients), however, produced different behavior. At high flow rates, all detectors produced essentially identical $\Delta R/R_b$ signals in the 20 s period after 240 s of analyte exposure, further confirming that the concentration of the analyte in proximity to each detector was similar and that the detectors themselves were very similar in response properties. However, at lower flow rates, lower $\Delta R/R_b$ values were observed in the 20 s period after 240 s of analyte exposure for the detectors to last encounter the vapor stream. To confirm that this effect was due to the physical location of the detector relative to the position of analyte flow injection, the direction of analyte flow in the chamber was again reversed and data were recollected for the entire sequence of analyte exposures. The lowest $\Delta R/R_b$ responses were again observed for detectors that were located farthest from the position of analyte injection.

The concentration of the low vapor pressure analyte stream is depleted by sorption into the first region of polymer composite film that it encounters, and the analyte concentration in the boundary layer that is exposed to the film is decreased further as the gas flow progresses along the length of the polymer composite. For analytes of low vapor pressure, all detectors produced essentially identical responses at high flow rates, whereas at sufficiently low flow rates different responses were observed for detectors located in different positions relative to the position of analyte injection into the chamber. In this transitional region of behavior, analysis of the relative signal strengths of the detectors in the array can provide information on the partition coefficient of the analyte into the polymer film of interest. FIG. 11 shows this effect for hexane, dodecane, and tridecane.

Figure 13:
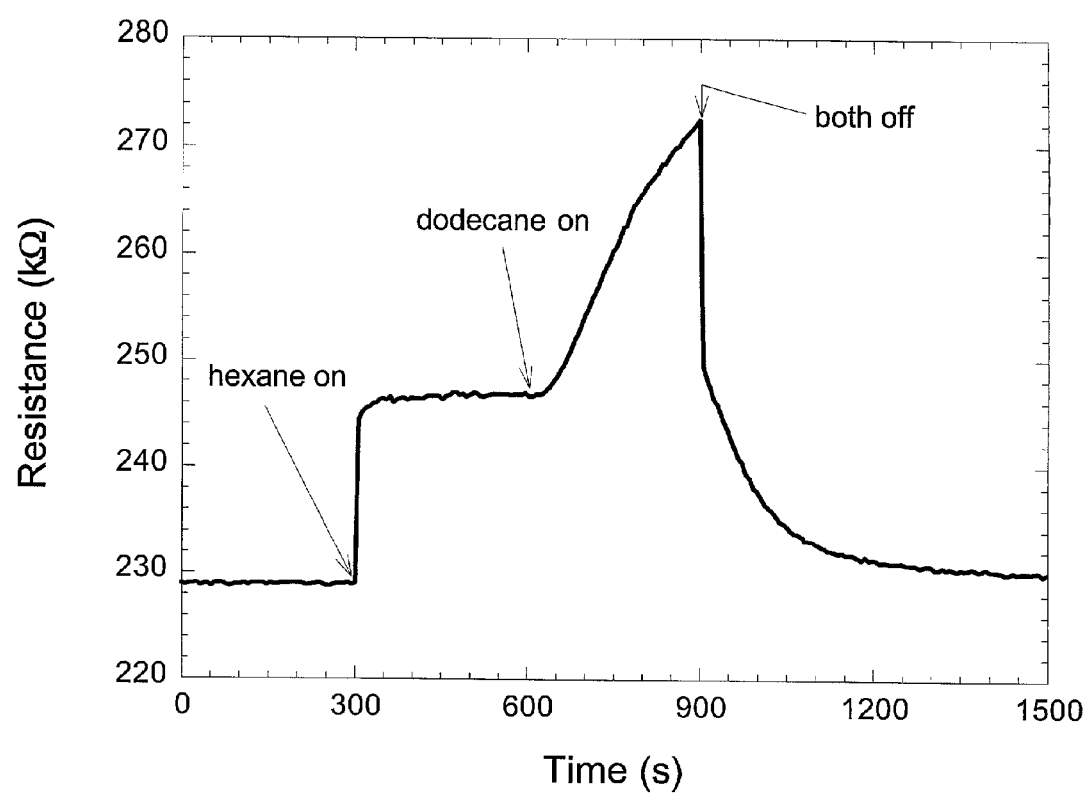
FIG. 13 illustrates a plot of resistance response as a function of time for a polymer-carbon black composite detector exposed to both hexane and a mixture of hexane and dodecane.

The effect of sorption of low vapor pressure analytes into the composite vapor detector films is also evident in the temporal response of the detectors. FIG. 13 shows resistance versus time data for exposure of a PEVA-carbon black composite to hexane (at P/P$^o$=0.10) followed immediately by exposure to a mixture of hexane and dodecane (each at P/P$^o$=0.10). These data were obtained at a relatively low carrier flow velocity (6 ml min$^{-1}$) on a PEVA-carbon black detector located at position 7 in FIG. 1A. Under these conditions, the different analytes can be distinguished based on their characteristic temporal responses on this detector that arise from the interactions with the analyte flow in the detector chamber.

Example 4

Vapor Response of Stacked Arrays of Chemically Equivalent, Spatially Nonequivalent Detectors The results obtained in Example 3 indicate that the noise decreases approximately as the square root of the detector area. Thus, for sufficient headspace volumes and quantities of sampled analyte so that the concentration of analyte sorbed into the polymer film remains constant as the detector area increases (as given by $K=C_p/C_v^{eq}$), an increased detector area will produce no change in the magnitude of the steady-state signal, a reduced value of the noise, and hence an increase in S/N ratio. However, for finite duration pulses of low vapor pressure compounds injected at low flow rates onto polymer films that have large polymer/gas partition coefficients, analyte sorption will only effectively occur onto the subset of detectors that are encountered initially by the analyte flow. In this situation, increasing the detector area decreases the S/N ratio and additionally masks the spatiotemporal dependence of analyte sorption that can be used to discriminate between analytes of differing polymer/gas partition coefficients (FIGS. 11–13). In this section, we describe the results of experiments designed to exploit both aspects of these properties of detector/analyte/flow interactions.

To investigate this trade-off between detector S/N and detector area, stacked sensor arrays were constructed according to FIGS. 5A and 5B, using rectangular 20 mm by 23 mm substrates that were fabricated by a commercial vendor (Power Circuits, Santa Ana, Calif.) using standard printed circuit board technology. Each of these substrates had electrical contacts deposited in a pattern that created a total of six detectors. Three detectors were located on the face of the substrate and three on the edge of the substrate. The three leading edge detectors were formed on the 840 μm thick edge of the substrate between parallel contacts that were located on each face of the circuit board. These detectors were located in positions 1e, 2e and 3e in FIG. 5B. The 20 mm by 23 mm faces of the circuit board supported the three larger detectors, each of which had dimensions of 2.0 mm by 15 mm (positions 1f, 2f, and 3f in FIG. 5B). The electrodes that formed face detectors in the same location on the top and bottom of each substrate were wired together in parallel (i.e. the leads to detector if on the top face were connected in parallel to the leads that addressed detector If on the bottom face of the substrate). On each substrate this arrangement therefore produced three face detectors, each having a total film area of 60 mm² (2×2.0 mm×15 mm).

Six total substrates of this type were prepared. Three of these substrates were prepared by spraying PEVA-carbon black films onto the edge and face detectors of the substrates, and three by spraying PCL-carbon black films onto the edge and face detectors of the substrates. To prevent current leakage between adjacent detectors, the films of the all individual detectors were isolated from each other by masking during spraying to produce a narrow (1 mm wide) gap in the detector film between adjacent detectors. Each of the six substrates was sprayed from an independently prepared suspension of carbon black and polymer, but both faces and the leading edge of a given substrate were sprayed from the same suspension. The two faces of a substrate were coated with a film of approximately the same resistance, to create films of similar thickness on each side of a given substrate.

One substrate sprayed with a PEVA-carbon black composite and one sprayed with a PCL-carbon black composite were then assembled into a stack that also contained 760 μm thick Al plates and 105 μm thick Teflon spacers. This assembly created a set of small channels, each of dimensions 0.105 mm×12 mm×23 mm, that permitted vapor to be drawn over each set of face detectors. The Teflon spacers served as the side walls for each channel. The assembled stack was 4.59 mm high (2×0.840 mm+3×0.760 mm+6×0.105 mm). Three separate stack assemblies of this type were built.

The stack assemblies were fitted into an Al chamber that had an open front and a tube connector on the back (away from the leading edge detectors). This tube connector was piped to a vacuum pump through a combination airflow meter and regulator (Cole Parmer). Each of the three stack assemblies used in this experiment contained six total channels formed collectively between the two substrates, the three Al plates, and the two walls of the chamber. Hence the volumetric flow of sampled gas through each individual channel was ⅙ of the volumetric flow of sample gas through the entire stack assembly.

These stacked detector arrays were exposed to various analytes of interest. In this configuration, with a detector film deposited on the edge of the substrate, and two other detector films of nominally identical composition deposited onto the two faces of the substrate, the face detector serves in essence as one large collection of detectors arranged linearly as in Example 3, thereby inherently averaging the responses, and providing reduced noise, for analytes with small polymer/gas partition coefficients. In contrast, the edge detector has a small area so that it can provide enhanced S/N performance for analytes with large polymer/gas partition coefficients. Two such substrates were then stacked such that the leading edge of each detector first encountered the analyte flow, with a component of the flow subsequently being directed along the faces of the substrate. One substrate had one polymer type forming its detectors and the other substrate had a separate, different carbon black/polymer composite material forming all of its detectors. The gaps between the substrates and the adjacent Al plates were sufficiently thin to insure that the flow would proceed in the desired direction. The entire experimental procedure and data collection were fully repeated 3 independent times, each time with 2 independently prepared substrates that were assembled into the stacked configuration of FIGS. 5A and 5B.

The $\Delta R/R_b$ responses, $N_{rms}$ values, and S/N values (FIG. 10) for each stack assembly are averages over the three detectors of the same geometry (face or edge) on a single substrate for 10 exposures to a given analyte. In FIG. 10, the results of the experiments on the three independently prepared stack devices are displayed separately. The average responses to high vapor pressure analytes (hexane and methanol) on the face detectors were between 75 and 100% of the magnitude of the responses on the edge detectors, while the lowest vapor pressure analyte, hexadecane, produced responses on the face detector that were all less than 15% of the values observed on the edge detectors (FIG. 10). This difference was much greater than the standard deviation of the responses of either all of the face detectors or all of the edge detectors on given substrate to an exposure to the analyte of interest.

The detector films on the leading edge of the substrate had 1/24 the area of the films on the face of the detectors, and therefore exhibited higher noise levels than the detectors on the face of the substrate. Noise values, $N_{rms}$, in the dc resistance readings measured using the multimeter were on average eight times higher for the PCL edge detectors than for the PCL face detectors, and were on average four times higher for the PEVA edge detectors than the PEVA face detectors (FIG. 10). The high vapor pressure analytes produced similar $\Delta R/R_b$ values on both detector types when exposed to methanol or hexane, hence the face detectors exhibited S/N ratios that reflected the decrease in noise produced by large volume detector films. For 200 s exposures to hexane, S/N values were ≈6 times higher for PCL face detectors and were ≈4 times higher for PEVA face detectors than for the corresponding edge detectors. In contrast, for 200 s exposures to hexadecane, the analyte with the lowest vapor pressure, the S/N values were about twice as high on the leading edge detectors as on the face detectors. Thus, the different geometric form factors and interactions with the analyte flow streamlines produced different performance characteristics from a S/N viewpoint for these different types of detectors.

Figure 14A:
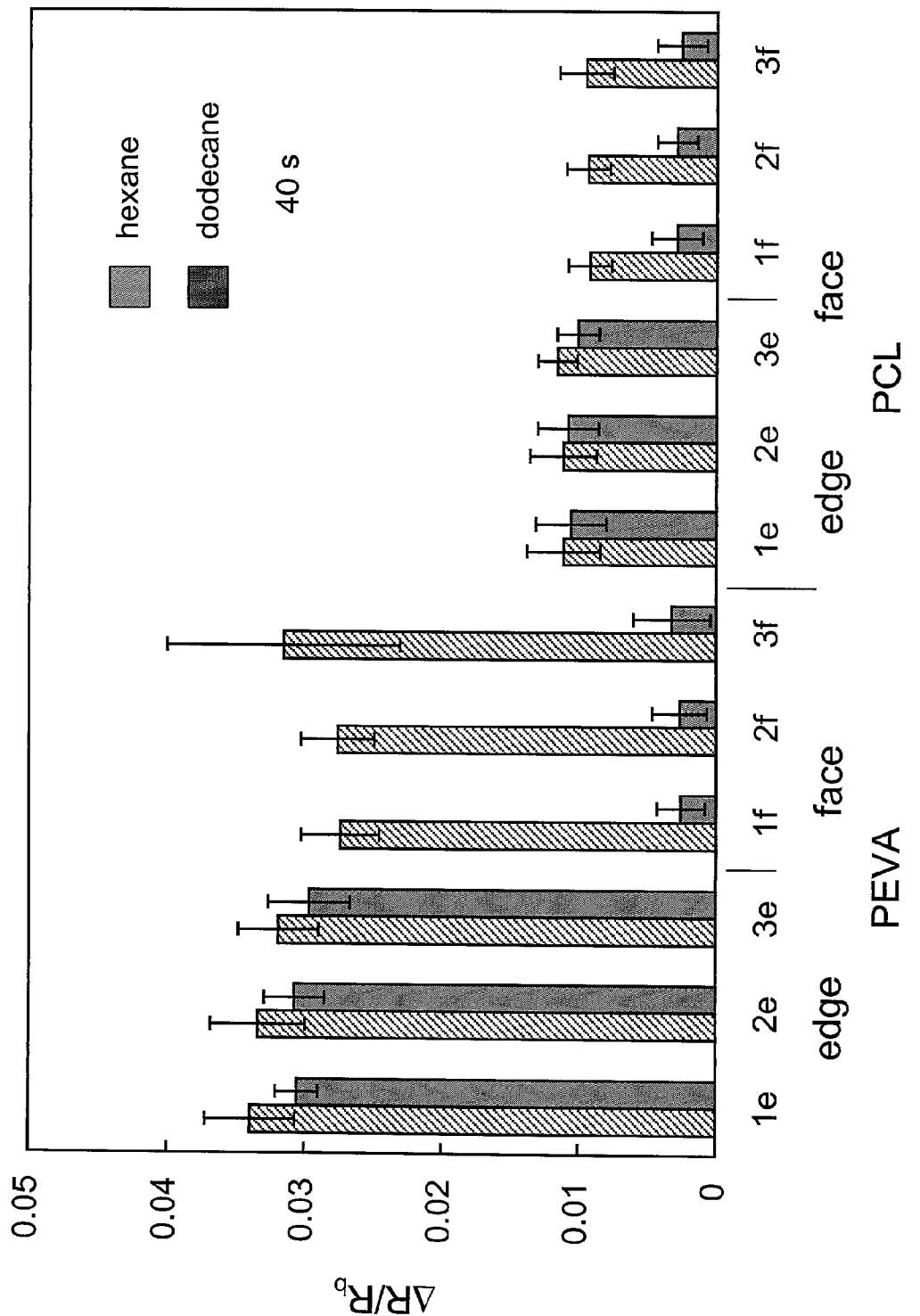
FIGS. 14A and 14B illustrate the relative differential resistance responses to hexane and dodecane after 40 seconds and 200 seconds of polymer-carbon black composite detectors located on the edge and face portions of a stacked sensor array as shown in FIG. 5A.
Figure 14B:
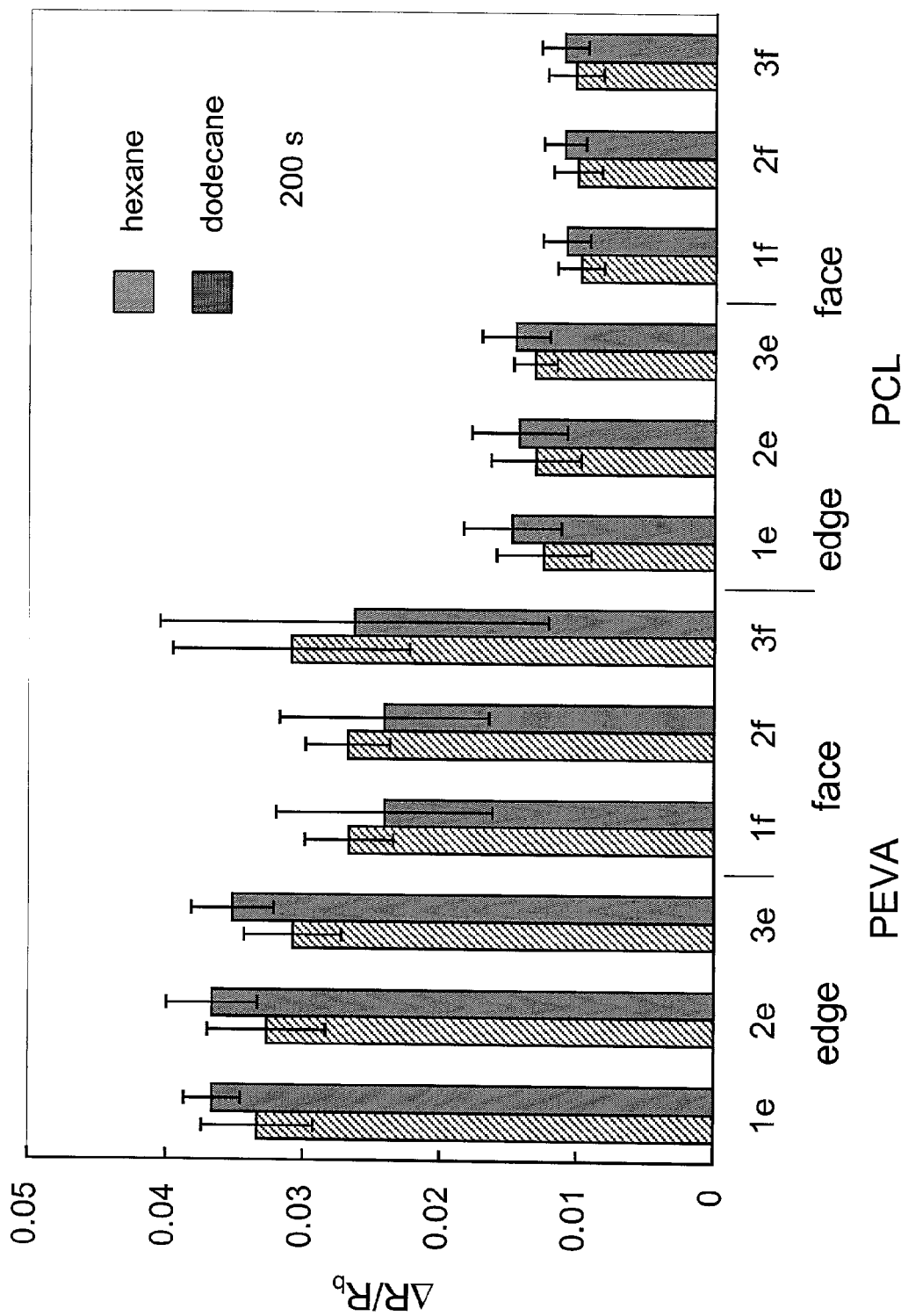

The temporal evolution of the detector response properties can also be used to differentiate between analytes. As shown in FIGS. 14A and 14B, the responses of the face and edge detectors to hexane were similar after 40 s of vapor presentation, and remained similar after 200 s. These hexane responses are similar in magnitude to the signals for dodecane after 200 s (FIG. 14B), and the two analytes could not easily be distinguished based on these data alone. However, the responses for these two analytes are clearly separable at 40 S (FIG. 14A), when the hexane has fully equilibrated with the given polymer film area but the dodecane is still being depleted from the analyte sample due to its very high polymer/gas partition coefficient. The separation of these analytes as a function of time therefore demonstrates an increase in the resolving power attainable through the use of such spatiotemporal response information in conjunction with a spatially ordered array of vapor detectors.

Example 5

Response at Constant Flow Rate of a Detector Array in the Presence of Volatile Organic Compounds and Water To further investigate the effects of interfering analytes on the detection of a target analyte, additional stacked sensor arrays were prepared. Nine detector composite types were used, each fabricated from a different insulating polymeric phase. The materials used to form these insulating phases for the detectors of the corresponding number are shown in Table 3.

TABLE 3

Figure 15:
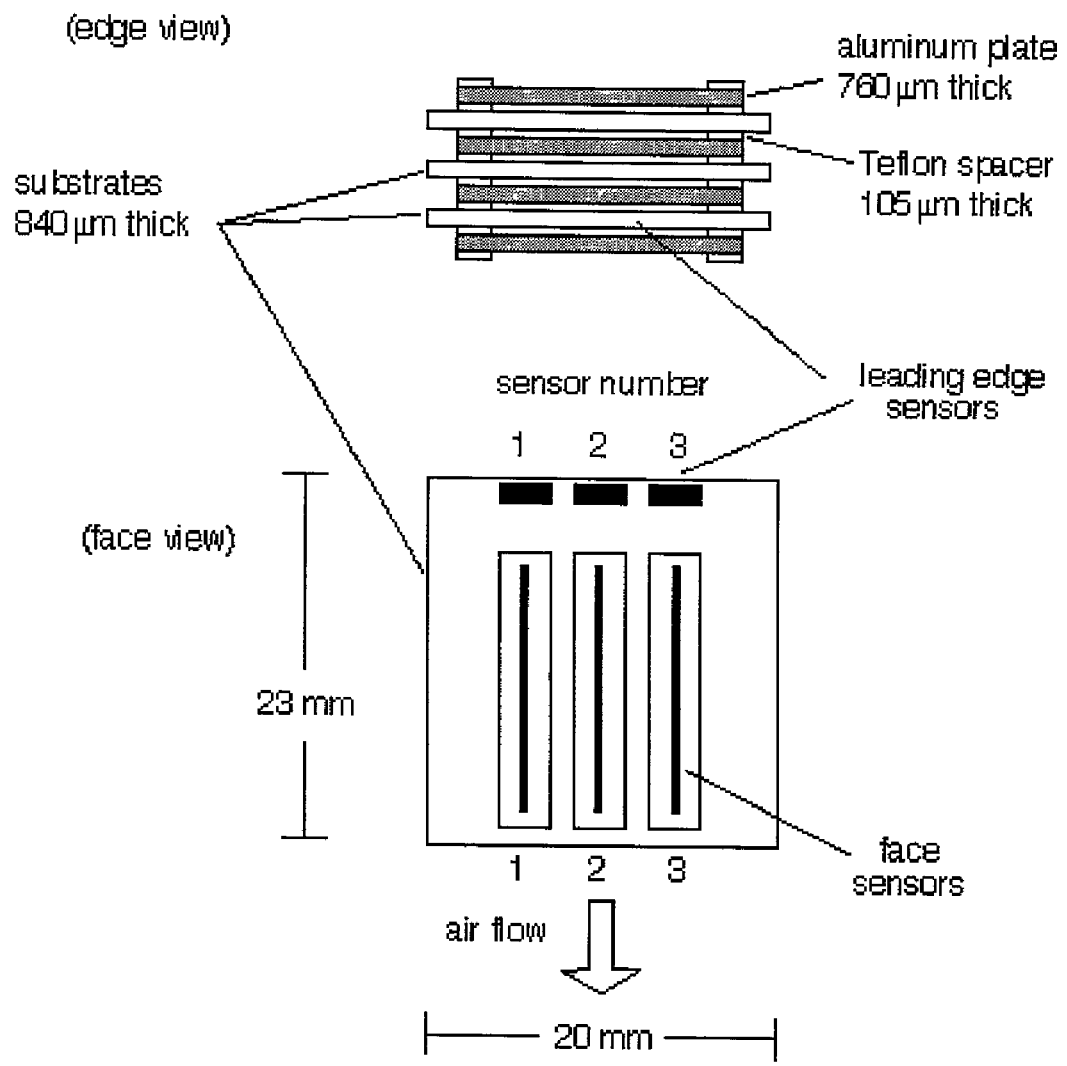
FIG. 15 illustrates one implementation of the stacked sensor array of FIG. 5A, involving 18 different detectors constructed from nine different sensor materials.

Detector Material:

1. PEVA (25% VA)
2. Polyethylene oxide
3. Polycaprolactone
4. Poly(vinyl stearate)
5. Polyvinylacetate + diethylene glycol dibenzoate 50% (wt/wt)
6. PMMA + diethylene glycol dibenzoate 50% (wt/wt)
7. PEVA (45% VA)
8. Styrene/isoprene
9. polymethyloctadecyl siloxane The composites used in this experiment were sprayed onto three circuit board substrates as illustrated in FIG. 15. Each substrate had electrical contacts deposited in a pattern that created a total of six detectors. Three detectors were located on each face (top and bottom) of the substrate and three detectors (of the same detector material) were located on the edge of the substrate. The three leading edge detectors were formed on the 840 μm thick edge of the substrate between parallel contacts that were located on each face of the circuit board. These detectors were located in positions 1, 2 and 3 of FIG. 15. The 20 mm by 23 mm faces of the circuit board supported the three larger detectors, each of which had dimensions of 2.0 mm by 15 mm. The electrodes that formed face detectors in the same location on the top and bottom of each substrate were wired together in parallel (i.e. the leads to face detector 1 on the top face were connected in parallel to the leads that addressed face detector 1 on the bottom face of the substrate). On each substrate this arrangement therefore produced three face detectors, each having a total film area of 60 mm$^2$ (2×2.0 mm×15 mm). Three of these substrates were stacked so that their leading edges were normal to the flow, and the flow through the gaps was controlled with a pump at 100 ml min$^{-1}$; consequently, the total flow of the diluted vapor stream between each chip was much lower than that directed at the edge detectors.

Saturated DNT vapor at 21° C. was obtained from a glass tube approximately one meter in length that held ≈180 g of loosely packed, granulated DNT. The air flow through this tube was 200 ml min$^{-1}$, with the background gas being oil-free laboratory air (1.10±0.15 parts per thousand (ppth) of water vapor). An additional gas stream passed through a bubbler that contained either acetone or water. Two in-line union-T's were used to mix the DNT vapor stream, the stream that contained either of the "interfering" vapors, and a background laboratory air gas stream. Flows were controlled with Teflon solenoid valves and mass flow controllers, in a computer-controlled system as described in Severin, et al., Anal. Chem. 2000, 72, 658–668. A short Teflon tube was connected to the output of the union to direct the gas toward the bank of detectors. The total flow rate of the gas directed at the detectors was held constant at 2 L min$^{-1}$ during all parts of the experiment. The DNT concentration after dilution was 10% of its vapor pressure. At this dilution, the upper limit of the DNT concentration is 14 parts per billion (ppb) because the vapor pressure of DNT at room temperature is approximately 140 ppb. When present in the vapor stream, the concentration of the acetone was 12.9 parts per thousand (ppth). Although the background air stream always contained some water vapor, the concentration was roughly doubled to ≈2.3 ppth during exposures that contained water as an "interfering" vapor. During exposures of the detector array, the vapor stream contained either pure DNT, water, or acetone; mixtures of DNT and water vapor; or mixtures of DNT and acetone vapor. Analyte exposures were 10 min in duration, and were separated in time by a 40 min exposure to the background air stream.

Figure 16:
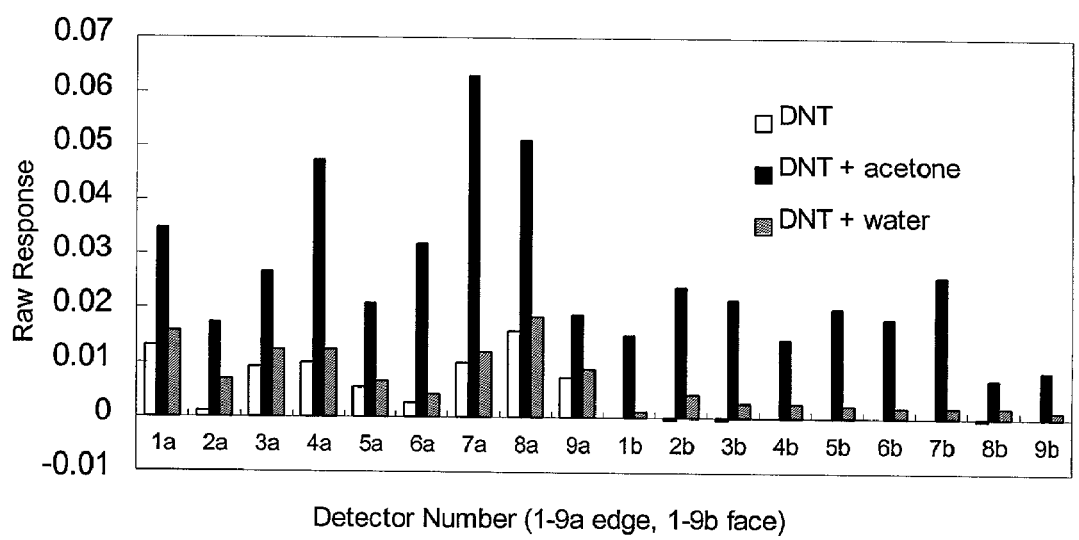
FIG. 16 illustrates the average differential resistance response computed as the baseline normalized differential resistance change of the detectors in the stacked sensor array of FIG. 15 after exposure to dinitrotoluene in the presence of two potentially interfering compounds.

The average ΔR/R response (computed as the baseline normalized differential resistance change of the detectors for 10 presentations of each vapor or mixture after 10 minute exposures to ppb levels of DNT in the presence of ppth levels of two potentially interfering compounds) of the array of 18 detectors to DNT and to mixtures of DNT that contained high concentrations of either acetone or water vapor is shown in FIG. 16. For pure analytes, vapors with small polymer/gas partition coefficients (generally analytes with high vapor pressures) produced similar magnitude signals on the leading edge and the corresponding face detector having the same composite material. In contrast, virtually all of the DNT (having a low vapor pressure and therefore a high polymer/gas partition coefficient in general) was trapped on the leading edge detectors and produced essentially no response on the face detectors. For mixtures that contained both DNT and high vapor pressure analytes, subtraction of the face detector response from the edge detector response yielded the response of only the low vapor pressure (high polymer/gas partition coefficient) component of the vapor mixture. Because the responses of carbon black-polymer composite films are linear with respect to concentration and additive with respect to components of binary mixtures (Severin, et al., Anal. Chem. 2000, 72, 658–668), subtraction techniques of this type can be applied without prior knowledge of the concentration or response pattern of the interfering vapor or knowledge of the effectiveness of the mass transport of the DNT vapor to the detector film.

Figure 17:
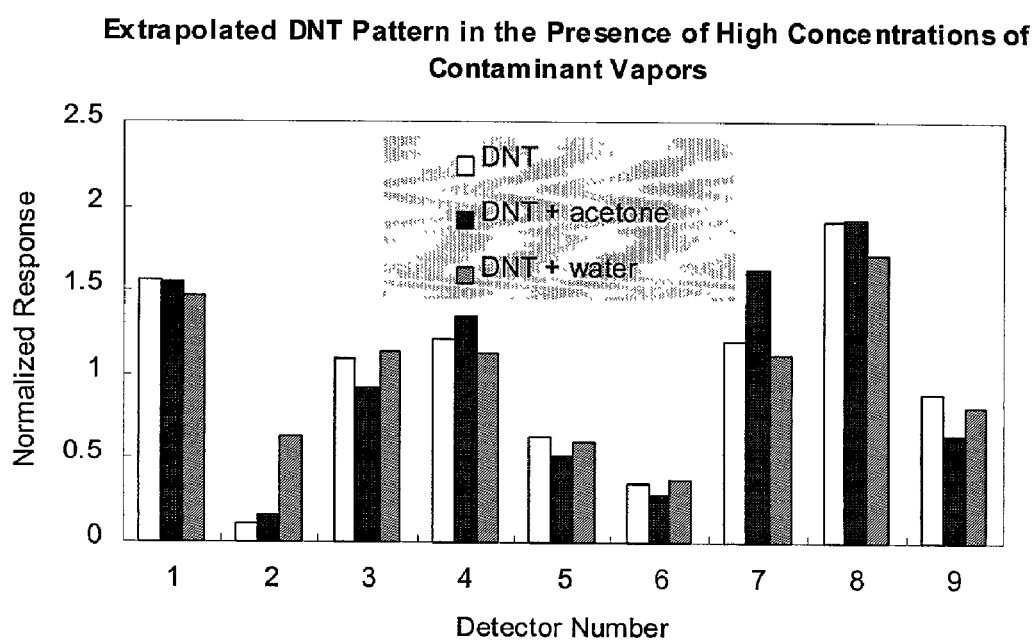
FIG. 17 illustrates the normalized array fingerprint patterns of pure dinitrotoluene and DNT in the presence of large concentrations of acetone or water for the sensor array of FIG. 15.

The responses to the high vapor pressure analyte on the large face detectors were first corrected by the slight variation in the relative sensitivity to both types of individual detectors (face and edge) and then subtracted to yield the response pattern of the pure DNT. This variation in sensitivity is expected to be independent of the concentration of the interfering analyte, permitting this correction to made against unknown concentrations of any contaminant analyte exhibiting small polymer/gas partition coefficients. The normalized array fingerprint patterns of pure DNT, and DNT in the presence of large concentrations of acetone or water are shown in FIG. 17. As FIG. 17 shows, the extrapolated response pattern of the detectors is similar to that of pure DNT even though the DNT was in the presence of much higher concentrations of acetone or water. Although the pre-equilibrium (time dependent) response pattern of the detectors to DNT or to any other analyte with a very high partition coefficient is expected to depend more closely on the film thickness of the individual detectors than on the specific interactions between the analyte and polymers of the individual detectors, the response pattern of the detectors to DNT is expected to be characteristic and is therefore useful in elucidating the existence of such a compound in the presence of high concentrations of interfering low partition coefficient compounds. Because responses of carbon black-polymer composite are additive in nature, subtraction techniques of this type could potentially remove an unlimited number of unknown interfering VOC's and water present simultaneously from the array pattern of DNT, provided that the relative sensitivity to these analytes on face and edge detectors is similar, as expected, for a given polymer composite. This hardware-based preprocessing capability circumvents many of the limitations of software-based pattern matching algorithms based on the face detector response alone, which would require prior knowledge of the array response to the specific interfering analyte and would encounter difficulties with the occurrence of high numbers of vapors simultaneously present in the vapor surrounding the DNT target.

While the invention has been described in detail with reference to certain embodiments thereof, it will be understood that modifications and variations are within the spirit and scope of that which is described and claimed.

What is claimed is:

1. A flow-through fluid analysis system for detecting an analyte in a fluid flow, comprising:
    a sensor array having a first face and a second face, the sensor array including one or more first sensors located on the first face and one or more fluid channels extending from the first face to the second face, at least one of the first sensors being located at a first position in the sensor array in contact with the first face of the sensor array, the one or more first sensors being configured to generate a response upon exposure of the sensor array to at least one analyte in a fluid flow;
    means for introducing a fluid flow containing an analyte to the sensor array, such that upon introduction of a fluid flow to the sensor array, including one or more first sensors located on the first face and one or more fluid channels extending from the first face to the second face, a pressure differential is created and maintained between the first and second faces of the sensor array; and
    a processor configured to receive the response generated by the one or more first sensors and to process the response to detect at least one analyte in a fluid flow.

2. The system of claim 1, wherein:
    the sensor array includes a substrate having a first surface and a second surface; and the fluid channels extend from the first surface to the second surface.

3. The system of claim 2, wherein:
    the fluid channels include a plurality of pores in a microporous substrate material.

4. The system of claim 2, wherein:
    the fluid channels include a plurality of holes introduced into an impermeable substrate material.

5. The system of claim 4, wherein:
    the fluid flow system includes a predetermined sampling volume,
    the sensor array is located within the sampling volume, and
    the first sensor has a sensor volume, the sensor volume being substantially optimized to cause the first sensor to generate a response having a maximum signal to noise ratio for at least one target analyte.

6. The system of claim 5, wherein:
    the sensor volume is substantially optimized as a function of a partition coefficient K of at least one target analyte.

7. The system of claim 6, wherein:
    the predetermined sampling volume includes a headspace proximate to the first sensor, the headspace having a headspace volume $V_l$; and the sensor volume $V_p$ is substantially optimized based on the function $V_p = V_{l/k}$.

8. The system of claim 1, wherein:
    the one or more first sensors include a vapor sensor for detecting an analyte in a gas.

9. The system of claim 8, wherein:
    the one or more first sensors include a plurality of vapor sensors for detecting an analyte in a gas.

10. The system of claim 1, wherein:
    the one or more first sensors include a liquid sensor for detecting an analyte in a liquid.

11. The system of claim 10, wherein:
    the one or more first sensors include a plurality of liquid sensors for detecting an analyte in a liquid.

12. The system of claim 1, wherein:
    the sensor array includes at least one second sensor located at a second position in the sensor array, the second position being different from the first position relative to the fluid flow, the first and second sensors each generating a response upon exposure of the sensor array to at least one analyte in a fluid flow, such that the responses generated upon exposure of the sensor array to at least one analyte in a fluid flow include a spatio-temporal difference between the responses for the first and second sensors.

13. The system of claim 12, wherein:
    the processor is configured to resolve a plurality of analytes in a fluid flow upon exposure of the sensor array to a fluid flow containing the plurality of analytes.

14. The system of claim 1, wherein:
    the sensor array includes a plurality of second sensors, each of the first sensor and a plurality of the second sensors being located at a different position in the sensor array relative to the fluid flow, the first and second sensors each generating a response upon exposure of the sensor array to at least one analyte in a fluid flow, such that the responses generated upon exposure of the sensor array to at least one analyte in a fluid flow include a spatio-temporal difference between the responses for the first and second sensors.

15. The system of claim 1, wherein:
    the sensor array includes a first substrate forming a plate having a length, a width, and a depth, such that the length and the width in combination define a pair of substrate faces and the width and the depth in combination define a pair of substrate edges, the first substrate being oriented in the sampling volume such that the substrate faces extend in a direction parallel to a direction of the fluid flow and the substrate edges are situated normal to the fluid flow; and
    the one or more first sensor are located on one of the pair of substrate edges.

16. The system of claim 15, wherein:
    the sensor array includes one or more second sensors located on one of the pair of substrate faces.

17. The system of claim 14, wherein:
    the processor is configured to resolve a plurality of analytes in a fluid flow upon exposure of the sensor array to a fluid flow containing the plurality of analytes.

18. The system of claim 15, wherein:
    the sensor array includes a plurality of second sensors located at different positions along one of the pair of substrate faces, such that the responses generated upon exposure of the sensor array to at least one analyte in a fluid flow include a spatio-temporal difference between responses generated by each of the first and the plurality of the second sensors.

19. The system of claim 16, wherein:
    the sensor array includes a plurality of substrates, each substrate forming a plate having a length, a width, and a depth, such that for each of the substrates the length and the width in combination define a pair of substrate faces and the width and the depth in combination define a pair of substrate edges, the substrates being oriented in the sampling volume such that the substrate faces extend in a direction parallel to a direction of the fluid flow and the substrate edges are situated normal to the fluid flow; and for each of the plurality of substrates, the sensor array includes one or more first sensors located on one of the pair of substrate edges and one or more second sensors located on at least one of the pair of substrate faces.

20. The system of claim 16, wherein:
at least one of the first sensor or the second sensors has a sensor volume, the sensor volume being substantially optimized to achieve a maximum signal to noise ratio for at least one target analyte.

21. The system of claim 20, wherein:
the sensor volume is substantially optimized as a function of a partition coefficient K of at least one target analyte.

22. The system of claim 21, wherein:
the predetermined sampling volume includes a headspace proximate to the first sensor, the headspace having a headspace volume $V_i$; and the sensor volume $V_p$ is substantially optimized based on the function $V_P = V_{1/K}$.

23. The system of claim 15, wherein:
the one or more first sensors include a vapor sensor for detecting an analyte in a gas.

24. The system of claim 23, wherein:
the one or more first sensors include a plurality of vapor sensors for detecting an analyte in a gas.

25. The system of claim 15, wherein:
the one or more first sensors include a liquid sensor for detecting an analyte in a liquid.

26. The system of claim 25, wherein:
the one or more first sensors include a plurality of liquid sensors for detecting an analyte in a liquid.

27. A method of detecting an analyte in a fluid flow, comprising:
providing a sensor array having a first face and a second face, the sensor array including one or more first sensors located on the first face and one or more fluid channels extending from the first face to the second face, at least one of the first sensors being located at a first position in the sensor array in contact with the first face of the sensor array, the one or more first sensors being configured to generate a response upon exposure of the sensor array to at least one analyte in a fluid flow;
exposing the sensor array to a fluid flow including an analyte under conditions sufficient to create and maintain a pressure differential between the first and second faces of the sensor array;
measuring a response for the one or more first sensors; and
detecting the presence of the analyte in the fluid based on the measured response.

28. The method of claim 27, wherein:
the sensor array includes a substrate having a first surface and a second surface; and
the fluid channels extend from the first surface to the second surface.

29. The method of claim 28, wherein:
the fluid channels include a plurality of pores in a microporous substrate material.

30. The method of claim 28, wherein:
the fluid channels include a plurality of holes introduced into an impermeable substrate material.

31. The method of claim 30, wherein:
the first sensor has a sensor volume, the sensor volume being substantially optimized to cause the first sensor to generate a response having a maximum signal to noise ratio for at least one target analyte.

32. The method of claim 31, wherein:
the sensor volume is substantially optimized as a function of a partition coefficient K of at least one target analyte.

33. The method of claim 32, wherein:
the predetermined sampling volume includes a headspace proximate to the first sensor, the headspace having a headspace volume $V_i$; and the sensor volume $V_p$, is substantially optimized based on the function $V_p = V_{1/K}$.

34. The method of claim 27, wherein:
the one or more first sensors include a vapor sensor for detecting an analyte in a gas.

35. The method of claim 34, wherein:
the one or more first sensors include a plurality of vapor sensors for detecting an analyte in a gas.

36. The method of claim 27, wherein:
the one or more first sensors include a liquid sensor for detecting an analyte in a liquid.

37. The method of claim 36, wherein:
the one or more first sensors include a plurality of liquid sensors for detecting an analyte in a liquid.

38. The method of claim 27, wherein:
the sensor array includes at least one second sensor located at a second position in the sensor array, the second position being different from the first position relative to the fluid flow, the first and second sensors each generating a response upon exposure of the sensor array to at least one analyte in a fluid flow, such that the responses generated upon exposure of the sensor array to at least one analyte in a fluid flow include a spatio-temporal difference between the responses for the first and second sensors.

39. The method of claim 38, wherein:
detecting the presence of the analyte in the fluid includes resolving a plurality of analytes in the fluid based on the measured response.

40. The method of claim 27, wherein:
the sensor array includes a plurality of second sensors, each of the first sensor and a plurality of the second sensors being located at a different position in the sensor array relative to the fluid flow, the first and second sensors each generating a response upon exposure of the sensor array to at least one analyte in a fluid flow, such that the responses generated upon exposure of the sensor array to at least one analyte in a fluid flow include a spatio-temporal difference between the responses for the first and second sensors.

41. The method of claim 27, wherein:
the sensor array includes a first substrate forming a plate having a length, a width, and a depth, such that the length and the width in combination define a pair of substrate faces and the width and the depth in combination define a pair of substrate edges, the first substrate being oriented in the sampling volume such that the substrate faces extend in a direction parallel to a direction of the fluid flow and the substrate edges are situated normal to the fluid flow; and
the one or more first sensor are located on one of the pair of substrate edges.

42. The method of claim 41, wherein:
the sensor array includes one or more second sensors located on one of the pair of substrate faces.

43. The method of claim 40, wherein:
detecting the presence of the analyte in the fluid includes resolving a plurality of analytes in the fluid based on the measured response.

44. The method of claim 41, wherein:
the sensor array includes a plurality of second sensors located at different positions along one of the pair of substrate faces, such that the responses generated upon exposure of the sensor array to at least one analyte in a fluid flow include a spatio-temporal difference between responses generated by each of the first and the plurality of the second sensors.

45. The method of claim 42, wherein:

the sensor array includes a plurality of substrates, each substrate forming a plate having a length, a width, and a depth, such that for each of the substrates the length and the width in combination define a pair of substrate faces and the width and the depth in combination define a pair of substrate edges, the substrates being oriented in the sampling volume such that the substrate faces extend in a direction parallel to a direction of the fluid flow and the substrate edges are situated normal to the fluid flow; and for each of the plurality of substrates, the sensor array includes one or more first sensors located on one of the pair of substrate edges and one or more second sensors located on at least one of the pair of substrate faces.

46. The method of claim 42, wherein:

at least one of the first sensor or the second sensors has a sensor volume, the sensor volume being optimized to achieve a maximum signal to noise ratio for at least one target analyte.

47. The method of claim 46, wherein:

the sensor volume is optimized as a function of a partition coefficient K of at least one target analyte.

48. The method of claim 47, wherein:

the predetermined sampling volume includes a headspace proximate to the first sensor, the headspace having a headspace volume $V_i$; and the sensor volume $V_p$, is optimized based on the function $V_P=V_{1/K}$.

49. The method of claim 41, wherein:

the one or more first sensors include a vapor sensor for detecting an analyte in a gas.

50. The method of claim 49, wherein:

the one or more first sensors include a plurality of vapor sensors for detecting an analyte in a gas.

51. The method of claim 41, wherein:

the one or more first sensors include a liquid sensor for detecting an analyte in a liquid.

52. The method of claim 51, wherein:

the one or more first sensors include a plurality of liquid sensors for detecting an analyte in a liquid.

53. A sensor array for detecting an analyte in a fluid flow, the sensor array having a first face and a second face, the sensor array comprising:

one or more substrates, each substrate forming a plate having a length, a width, and a depth, such that the length and the width in combination define a pair of substrate faces and the width and the depth in combination define a first substrate edge and a second substrate edge, the first substrate edge for each of the substrates being aligned with the first face of the array;

a plurality of chemically sensitive resistor sensors configured to generate a response upon exposure of the sensor array to at least one analyte in a fluid flow, the sensors including one or more first sensors, each of the first sensors being located along one of the first substrate edges, the sensors also including one or more second sensors, each of the second sensors being located along one of the substrate faces; and one or more fluid channels extending along one or more of the substrate faces from the first face of the array to the second face of the array.

54. The sensor array of claim 53, wherein:

the plurality of sensors includes a plurality of second sensors located at different positions along at least one of the pair of substrate faces, such that the responses generated upon exposure of the sensor array to at least one analyte in a fluid flow include a spatio-temporal difference between responses generated by each of the first and the plurality of the second sensors.

55. The sensor array of claim 53, wherein:

the sensors include a vapor sensor for detecting an analyte in a gas.

56. The sensor array of claim 55, wherein:

the sensors include a plurality of vapor sensors for detecting an analyte in a gas.

57. The sensor array of claim 53, wherein:

the sensors include a liquid sensor for detecting an analyte in a liquid.

58. The sensor array of claim 57, wherein:

the sensors include a plurality of liquid sensors for detecting an analyte in a liquid.

59. A device, comprising:

a fluid inlet;

a fluid outlet;

a fluid flow channel disposed between the fluid inlet and the fluid outlet;

a sensor array comprising
 a first face;
 a second face;
 one or more fluid pores extending from the first face to the second face;
 one or more sensors, at least one of the sensors being located at a first position in the sensor array in contact with the first face of the sensor array, the one or more first sensors being configured to generate a response upon exposure of the sensor array to at least one analyte in a fluid flow, the sensor array configured in the fluid flow channel to generate a pressure drop from the first face to the second face, whereby fluid flows through the one or more fluid pores; and a processor configured to receive the response generated by the one or more sensors and to process the response to detect at least one analyte in a fluid flow.

60. The device of claim 59, wherein:

the sensor array comprises a microporous material.

61. The device of claim 59, wherein:

the one or more sensors comprise one or more vapor sensors for detecting an analyte in a gas.

62. The device of claim 59, wherein:

the one or more sensors comprise one or more liquid sensors for detecting an analyte in a liquid.

* * * * *